(12) United States Patent
Hunter et al.

(10) Patent No.: US 9,683,026 B2
(45) Date of Patent: Jun. 20, 2017

(54) WSX-1/P28 AS A TARGET FOR ANTI-INFLAMMATORY RESPONSES

(75) Inventors: Christopher A. Hunter, Swarthmore, PA (US); Jason Scott Stumhofer, Plymouth Meeting, PA (US)

(73) Assignee: THE TRUSTEES OF THE UNIVERSITY OF PENNSLYVANIA, Philadelphia, PA (US)

( * ) Notice: Subject to any disclaimer, the term of this patent is extended or adjusted under 35 U.S.C. 154(b) by 778 days.

(21) Appl. No.: 11/880,121

(22) Filed: Jul. 18, 2007

(65) Prior Publication Data

US 2008/0038223 A1    Feb. 14, 2008

Related U.S. Application Data

(60) Provisional application No. 60/832,213, filed on Jul. 19, 2006, provisional application No. 60/837,450, filed on Aug. 11, 2006.

(51) Int. Cl.
*A61K 38/00* (2006.01)
*C07K 14/54* (2006.01)
*C07K 14/715* (2006.01)
*A61K 38/18* (2006.01)
*A61K 35/15* (2015.01)
*A61K 35/17* (2015.01)
*G01N 33/68* (2006.01)

(52) U.S. Cl.
CPC ............... *C07K 14/54* (2013.01); *A61K 35/15* (2013.01); *A61K 35/17* (2013.01); *A61K 38/1841* (2013.01); *C07K 14/7155* (2013.01); *G01N 33/6863* (2013.01); *A61K 38/00* (2013.01); *C07K 2319/00* (2013.01)

(58) Field of Classification Search
CPC ...... A61K 38/20; A61K 39/395; C07K 16/00; C07K 14/54; G01N 33/53
See application file for complete search history.

(56) References Cited

U.S. PATENT DOCUMENTS 5,118,791 A * 6/1992 Burnier et al. ............... 530/326
5,686,575 A   11/1997 Prince et al.
(Continued)

FOREIGN PATENT DOCUMENTS

WO    WO 97/25425         7/1997
WO    WO 9725425 A1 *    7/1997
(Continued)

OTHER PUBLICATIONS

UniProt Q8NEV9, IL-27A (p. 28), last accessed Mar. 12, 2014 (original date of sequence Oct. 1, 2002).*
(Continued)

*Primary Examiner* — Cherie M Stanfield
(74) *Attorney, Agent, or Firm* — Saul Ewing LLP; Kathryn Doyle

(57) ABSTRACT

Compositions and methods relating to WSX-1 and p28 (IL-30) are provided. In particular, methods of treating inflammatory conditions in mammalian subjects using various WSX-1, p28, EBI3, and gp130 polypeptides and complexes or moieties that bind to or modulate activity of such complexes are described. Isolated or recombinant complexes including soluble WSX-1 or gp130 polypeptides, isolated or recombinant WSX-1 fusion proteins, and isolated or recombinant p28 fusion proteins are also described.

6 Claims, 22 Drawing Sheets

(56) References Cited

U.S. PATENT DOCUMENTS

| | | | |
|---|---|---|---|
| 7,074,397 B1* | 7/2006 | Matthews | 424/85.1 |
| 7,148,330 B2* | 12/2006 | Timans et al. | 530/387.9 |
| 2002/0164609 A1* | 11/2002 | Timans et al. | 435/6 |
| 2004/0185049 A1 | 9/2004 | Hunter | |
| 2004/0234522 A1* | 11/2004 | DeSauvage et al. | 424/144.1 |
| 2012/0004130 A1 | 1/2012 | Mattoon et al. | |
| 2015/0079024 A1* | 3/2015 | Hunter | A61K 38/20 |
| | | | 424/85.2 |

FOREIGN PATENT DOCUMENTS

| | | |
|---|---|---|
| WO | WO 99/02552 A2 | 1/1999 |
| WO | WO 01/29070 A2 | 4/2001 |
| WO | WO 0129070 A2 * | 4/2001 |
| WO | WO 2004/069173 A2 | 8/2004 |
| WO | WO 2005/079848 A2 | 9/2005 |
| WO | WO 2005/079848 A3 | 9/2005 |

OTHER PUBLICATIONS

UniProt Q6UWB1 (IL-27RA) (also known as WSX-1/TCCR) (original date of sequence May 2, 1998) (last accessed May 30, 2015).*

Pflanz et al., (J Immunol. 2004;172:2225-2231).*

Rosas et al., (J Path. Jan. 1, 2006;168(1):158-169).*

Maeda et al., (J Immunol. Nov. 15, 1995;155(10):4926-32, abstract only).*

Afkarian et al. (2002) "T-bet is a STAT I-induced regulator of IL-I2R expression in naïve CD4+T cells." *Nature Immunology*, 3(6): 549-557.

Aggarwal et al. (2003) "Interleukin-23 promotes a distinct CD4 T cell activation state characterized by the production of interleukin-17," *J Biol Chem* 278(3):1910-1914.

Agnello et al.(2003) "Cytokines and Transcription Factors That Regulate T Helper Cell Differentiation: New Players and New Insights." *Journal of Clinical Immunology*, 23(3): 147-161.

Alexander et al. (1999) "SOCS1 is a Critical Inhibitor of Interferon γ Signaling and Prevents the Potentially Fatal Neonatal Actions of this Cytokine." *Cell*, 98: 597-608.

Altare et al. (1998) "Impairment of Mycobacterial Immunity in Human Interleukin-12 Receptor Deficiency." *Science*, 280: 1432-1435.

Amadi-Obi et al. (2007) "T(H)17 cells contribute to uveitis and scleritis and are expanded by IL-2 and inhibited by IL-27/STAT1," *Nat Med* 13(6):711-718.

Anti-human TCCR/WSX-1 antibody—R&D Systems—spec and use sheet (product description), 1 page, May 29, 2007.

Artis et al. (1999) "Tumor Necrosis Factor αIs a Critical Component of Interleukin 13-mediated Protective T Helper Cell Type 2 Responses during Helminth Infection." *Journal of Experimental Medicine*, 190(7): 953-962.

Artis et al. (2002) "Differential Requirement for NF-κB Family Members in Control of Helminth Infection and Intestinal Inflammation." *The Journal of Immunology*, p. 4482-4487.

Artis et al. (2004) "Cutting edge: early IL-4 production governs the requirement for IL-27-WSX-1 signaling in the development of protective Th1 cytokine responses following Leishmania major infection,". *J Immunol* 172(8):4672-4675.

Artis et al. (2004) "The IL-27 receptor (WSX-1) is an inhibitor of innate and adaptive elements of type 2 immunity," *J Immunol*, 173:5626-5634.

Awasthi et al.. (2007) "A dominant function for interleukin 27 in generating interleukin 10-producing anti-inflammatory T cells," *Nat Immunol*, 8(12):1380-1389.

Bancroft (1998) "A Critical Role for IL-13 in Resistance to Intestinal Nematode Infection." *The Journal of Immunology*, 160(7):3453-3461.

Batten et al. (2006) "Interleukin 27 limits autoimmune encephalomyelitis by suppressing the development of interleukin 17-producing T cells," *Nat Immunol* 7(9):929-936.

Bettelli et al. (2006) "Reciprocal developmental pathways for the generation of pathogenic effector T(H)17 and regulatory T cells," *Nature*, 441(7090):235-238.

Boyman et al. (2006) "Selective Stimulation of T Cell Subsets with Antibody-Cytokine Immune Complexes" *Science*, 311:1924-1927.

Brombacher et al.(2003) "Novel IL-12 family members shed light on the orchestration of TH1 responses." *TRENDS in Immunology*, 24(4): 207-212.

Cai et al. (2000) "Identification of STAT4-Dependent and Independent Mechanism of Resistance to Toxoplasma gonddi." *The Journal of Immunology*, 2619-2627.

Chen et al. (2000) "Development of Th1-type immune responses requires the type I cytokine receptor TCCR," *Nature*, 407:916-920.

Chu et al. (2000) "Failure to Suppress the Expansion of the Activated CD4 T Cell Population in Interferon γ-deficient Mice Leads to Exacerbation of Experimental Autoimmune Encephalomyelitis." *Journal of Experimental Medicine*, 192(1): 123-128.

Cousens et al. (1997) "Interferon-α/β inhibition of interleukin 12 and interferon-□ production in vitro and endogenously during viral infection." *Proceedings of the National Academy of Sciences*, USA, 94: 634-639.

Dalton et al. (2000) "Interferon γ Eliminates Responding CD4 T Cells during Mycobacterial Infection by Inducing Apoptosis of Activated CD4 T Cells." *Journal of Experimental Medicine*, 192(1): 117-122.

De Jong et al. (1998) "Severe Mycobacterial and *Salmonella* Infections in Interleukin-12 Receptor-Deficient Patients." *Science*, 280: 1435-1438.

Denkers and Gazzinelli (1998) "Regulation and Function of T-Cell-Mediated Immunity during Toxoplasma gondii Infection." *Clinical Microbiology Reviews*, 11(4): 569-588.

Diehl et al. (2000) "Inhibition of Th1 Differentiation by IL-6 is Mediated by SOCS1." *Immunity*, 13: 805-815.

Doyle et al. (2001) "Induction of Cytotoxic T Lymphocyte Antigen 4 (CTLA-4) Restricts Clonal Expansion of Helper T Cells." *Journal of Experimental Medicine*, 194(7): 893-902.

Egen et al.. (2002) "CTLA-4: new insights into its biological function and use in tumor immunotherapy," *Nat Immunol*, 3(7):611-618.

Else et al. (1994) "Cytokine-mediated Regulation of Chronic Intestinal Helminth Infection." *The Journal of Experimental Medicine*, 179: 347-351.

Ely et al. (1999) "Augmentation of the CD8+ T Cell Response by IFN-γ in IL-12-Deficient Mice During Toxoplasma gondii Infection." *The Journal of Immunology*, 5449-5454.

Fitzgerald et al. (2007) "Suppressive effect of IL-27 on encephalitogenic Th17 cells and the effector phase of experimental autoimmune encephalomyelitis," *J Immunol.*, 179(5):3268-3275.

Fujimoto et al. (2002) "A regulatory role for suppressor of cytokine signaling-1 in $T_h$ polarization in vivo." *International Immunology*, 14(11): 1343-1350.

Gazzinelli et al. (1993) "Interleukin 12 is required for the T0lymphocyte-independent induction of interferon γ by an intracellular parasite and induces resistance in T-cell-deficient hosts." *Proceedings of the National Academy of Sciences, USA*, 90: 6115-6119.

Gazzinelli et al. (1994) "Parasite-Induced IL-12 Stimulates Early IFN-□ Sythesis and Resistance During Acute Infection with Toxoplasma gondii." *The Journal of Immunology*, p. 2533-2543.

Gazzinelli et al. (1996) "In the absence of endogenous IL-10, mice acutely infected with Toxoplasma gondii succumb to a lethal immune response dependent on CD4+ T cells and accompanied by overproduction of IL-12, IFN-gamma and TNF-alpha" *J Immunol.*, 157:798-805.

Hamano et al. (2003) "WSX-1 is required for resistance to Trypanosoma cruzi infection by regulation of proinflammatory cytokine production," *Immunity*, 19:657-667.

Harrington et al. (2005) "Interleukin 17-producing CD4+ effector T cells develop via a lineage distinct from the T helper type 1 and 2 lineages," *Nat Immunol*, 6(11):1123-1132.

(56) References Cited

OTHER PUBLICATIONS

Heinrich et al. (1998) "Interlukin-6-type cytokine signaling through the gp130/Jak/STAT pathway," *Biochem. J,.* 334(Pt 2):297-314.

Helmby et al. (2001) "Interleukin (IL)-18 Promotes the Development of Chronic Gastrointestinal Helminth Infection by Downregulating IL-13." *Journal of Experimental Medicine*, 194(3): 355-364.

Hibbert et al. (2003) "IL-27 and IFN-α Signal via Stat1 and Stat3 and Induce T-Bet and IL-12Rβ2 in Native T Cells." *Journal of Interferon & Cytokine Research*, 23: 513-522.

Ho and Glimcher (2002) "Transcription: tantalizing Times for T Cells." *Cell*, 109: S109-S120.

Holscher et al. (2005) "The IL-27 receptor chain WSX-1 differentially regulates antibacterial immunity and survival during experimental tuberculosis," *J Immunol*, 174(6):3534-3544.

Hunter (2005) "New IL-12-family members: IL-23 and IL-27, cytokines with divergent functions," *Nat Rev Immunol*, 5(7):521-531.

Hunter et al. (1997) "IL-10 is Required to Prevent Immune Hyperactivity During Infection with Trypanosoma cruzi." *The Journal of Immunology*, 3311-3316.

Jostock et al. (2001) "Soluble gp130 is the natural inhibitor of soluble interleukin-6 receptor transsignaling responses," *Eur. J. Biochem.* 268(1):160-167.

Kamiya et al. (2004) "An indispensable role for STAT1 in IL-27-induced T-bet expression but not proliferation of naive CD4+ T cells," *J Immunol*, 173(6):3871-3877.

Kastelein et al. (2007) "Discovery and biology of IL-23 and IL-27: related but functionally distinct regulators of inflammation,"*Annu Rev Immunol*, 25:221-242.

Langrish et al. (2005) "IL-23 drives a pathogenic T cell population that induces autoimmune inflammation," *J Exp Med*, 201(2):233-240.

Lee et al. (2000) "STAT1 Affects Lymphocyte Survival and Proliferation Partially Independent of Its Role Downstream of IFN-γ." *The Journal of Immunology*, 1286-1292.

Li et al. (2005) "IL-27 subunits and its receptor (WSX-1) mRNAs are markedly up-regulated in inflammatory cells in the CNS during experimental autoimmune encephalomyelitis," *J Neurol Sci*, 232(1-2):3-9.

Liesenfield et al. (1996) "Association o CD4+ T Cell-dependent, Interferon-☐-mediated Necrosis of the Small Intestine with Genetic Susceptibility of Mice to Peroral Infection with Toxoplasma gondii." *The Journal of Experimental Medicine*, 184: 597-607.

Lighvani et al. (2001) "T-bet is rapidly induced by interferon-γ in lymphoid and myeloid cells." *Proceedings of the National Academy of Sciences, USA*, 98(26): 15137-15142.

Lin et al. (2006) "The functional expression of a biologically active fragment of soluble gp130 as an ELP fusion protein in transgenic plants: purification via inverse-transition-cycling" *Biochem J.*, 398(3):577-583.

Lucas et al. (2003) "IL-27 regulates IL-12 responsiveness of naive CD4+ T cells through Stat1-dependent and -independent mechanisms," *PNAS*, 100:15047-15052.

Mangan et al. (2006) "Transforming growth factor-beta induces development of the T(H)17 lineage," *Nature*, 441(7090):231-234.

McKenzie et al. (1998) "A district role for interleukin-13 in Th2-cell-mediated immune responses." *Current Biology*, 8: 339-342.

Mullen (2001) "Role of T-Bet in Commitment of $T_H1$ Cells Before IL-12-Dependent Selection." *Science*, 292: 1907-1910.

Murphy et al. (2002) "The Lineage Decisions of Helper T Cells." *Nature Reviews, Immunology*, 2: 933-942.

Naka et al. (2001) "SOCS-1/SSI-1-Deficient NKT Cells Participate in Severe Hepatitis through Dysregulated Cross-Talk Inhibition of IFN-γ and IL-4 Signaling In Vivo." *Immunity*, 14: 535-545.

Nakagawa et al. (2002) "SOCS-1 Participates in Negative Regulation of LPS Responses." *Immunity*, 17: 677-687.

Neufert et al. (2007) "IL-27 controls the development of inducible regulatory T cells and Th17 cells via differential effects on STAT1," *Eur J Immunol*, 37(7):1809-1816.

Neyer et al. (1997) "Role of Interleukin-10 in Regulation of T-Cells-Dependent and T-Cell-Independent Mechanisms of Resistance to Toxoplasma gondii." *Infection and Immunity*, 65(5): 1675-1682.

Nguyen et al. (2000) "Interferon α/β-Mediated inhibition and promotion of interferon ☐: STAT1 resolves a paradox." *Nature Immunology*, 1(1): 70-76.

Nieuwenhuis et al. (2002) "Disruption of T helper 2-immune responses in Epstein-Barr virus-induced gene 3-deficient mice." *Proceedings of the National Academy of Sciences, USA*, 99(26): 16951-16956.

O'Shea et al. (2002) "Cytokine Signaling in 2002: New Surprises in the Jak/Stat Pathway." *Cell*, 109: S121-S131.

Owaki et al. (2006) "IL-27 suppresses CD28-mediated IL-2 production through suppressor of cytokine signaling 3," *J Immunol* ,176(5):2773-2780.

Park et al. (2005) "A distinct lineage of CD4 T cells regulates tissue inflammation by producing interleukin 17," *Nat Immunol*, 6(11):1133-1141.

Pflanz et al. (2002) "IL-27, a heterodimeric cytokine composed of EBI3 and p28 protein, induces proliferation of naive CD4(+) T cells," *Immunity*, 16:779-790.

Pflanz et al. (2004) "WSX-1 and glycoprotein 130 constitute a signal-transducing receptor for IL-27," *J Immunol*, 172(4):2225-2231.

Recombinant human TCCR/WSX-1/Fc chimeras—R&D Systems—spec and use sheet (product description), May 20, 2005.

Recombinant mouse TCCR/WSX-1/Fc chimeras—R&D Systems—spec and use sheet (product description), Nov. 2, 2005.

Recombinant human EBI3—Abnova—spec sheet (product description), Nov. 21, 2007.

Recombinant human p28—Abnova—spec sheet (product description), Nov. 21, 2007.

Robinson and O'Garra (2002) "Further Checkpoints in Th1 Development," *Immunity*, 16: 755-758.

Rosas et al. (2006) "Interleukin-27R (WSX-1/T-Cell Cytokine Receptor) Gene-Deficient Mice Display Enhanced Resistance to Leishmania donovani Infection but Develop Severe Liver Immunopathology," *Am J Pathol.*, 168(1):158-169.

Scharton-Kersten et al. (1996) "In the Absence of Endogenous IFN-☐, Mice Develop Unimpaired IL-12 Responses to Toxoplasma gondii While Failing to Control Acute Infection," *The Journal of Immunology*, 4045-4054.

Scheller et al. (2005) "No inhibition of IL-27 signaling by soluble gp130," *Biochem. Biophys. Res. Comm.*, 326(4):724-728.

Seki et al. (2003) "SOCS-3 regulates onset and maintenance of $T_H2$-mediated allergic responses." *Nature Medicine*, 9(8): 1047-1054.

Sonobe et al. (2005) "Production of IL-27 and other IL-12 family cytokines by microglia and their subpopulations," *Brain Res.*,1040(1-2):202-207.

Sprecher et al. (1998) "Cloning and characterization of a novel class I cytokine receptor," *Biochem Biophys Res Commun.*, 246:82-90.

Stetson et al. (2002) "Rapid Expansion and IL-4 Expression by Leishmania-Specific Native Helper T Cells In Vivo," *Immunity*, 17:191-200.

Stumhofer et al. (2006) "Interleukin 27 negatively regulates the development of interleukin 17-producing T helper cells during chronic inflammation of the central nervous system," *Nat Immunol.*, 7(9):937-945.

Stumhofer et al. (2007) "146 A Central Role for Interleukin 27 and IL-6 Mediated Activation of STAT3 in T Cell Production of IL-10," *Cytokine*, 39(1):40-41.

Stumhofer et al. (2007) "Interleukins 27 and 6 induce STAT3-mediated T cell production of interleukin 10," *Nat Immunol.*, 8(12):1363-1371.

Suzuki et al. (1994) "Antibody against interleukin-6 reduces inflammation and numbers of cysts in brains of mice with toxoplasmic encephalitis," *Infect Immun.*, 62(7):2773-2778.

Szabo et al. (2003) "Molecular Mechanisms Regulating $T_H1$ Immune Responses." *Annual Review of Immunology*, 21: 713-758.

Taga & Kishimoto (1997) "Gp130 and the interleukin-6 family of cytokines,"*Annu Rev Immunol.*, 15:797-819.

(56) References Cited

OTHER PUBLICATIONS

Takeda et al. (2003) "Cutting Edge: Role of IL-27/WSX-1 Signaling for Induction of T-Bet Through Activation of STAT1 During Initial Th1 Commitment." *The Journal of Immunology*, 170: 4886-4890.
Trinchieri et al. (2003) "Interleukin-12 and the Regulation o Innate Resistance and Adaptive Immunity," *Nature Reviews, Immunology*, 3:133-146.
Villarino et al. (2003) "The IL-27R (WSX-1) is required to suppress T cell hyperactivity during infection," *Immunity*, 19(5):645-655.
Villarino & Hunter (2004) Biology of recently discovered cytokines: discerning the pro- and anti-inflammatory properties of interleukin-27. *Arthritis Res Ther* 6(5):225-33.
Villarino et al. (2006) "IL-27 limits IL-2 production during Th1 differentiation," *J. Immunol.*,176(1):237-247.
Villarino et al. (2005) "Positive and negative regulation of the IL-27 receptor during lymphoid cell activation," *J Immunol.*, 174(12):7684-7691.
Villarino et al. (2004) "Understanding the pro- and anti-inflammatory properties of IL-27," *J Immunol.*, 173(2):715-720.
Welte et al. (2003) "STAT3 deletion during hematopoiesis causes Crohn's disease-like pathogenesis and lethality: A critical role of STAT3 in innate immunity," *Proceedings of the National Academy of Sciences, USA*, 100(4):1879-1884.
Wille et al. (2001) "Interleukin-10 does not contribute to the pathogenesis of a virulent strain of Toxoplasma gondii." *Parasite Immunol.*, 23(6):291-296.
Wilson et al. (2005) "A critical role for IL-10 in limiting inflammation during toxoplasmic encephalitis," *J Neuroimmunol.*, 165(1-2) :63-74.
Wirtz et al. (2006) "Protection from lethal septic peritonitis by neutralizing the biological function of interleukin 27" *J. Exp. Med.*, 203(8):1875-1881.
Yamanaka et al. (2004) "Hyperproduction of proinflammatory cytokines by WSX-1-deficient NKT cells in concanavalin A-induced hepatitis," *J Immunol* .,172(6):3590-3596.
Yoo et al. (2002) "Specific Ablation of Stat3β Distorts the Pattern of Stat3-Responsive Gene Expression and Impairs Recovery from Endotoxic Shock." *Cell*, 108:331-344.
Yoshida et al. (2001) "WSX-1 is required for the initiation of Th1 responses and resistance to L. major infection," *Immunity*, 15:569-578.
Abstracts of the AGA Institute (2006) 130(4): pp. A1-A363.
Batten et al, (2006) Interleukin 27 limits autoimmune encephalomyelitis by suppressing the development of interleukin 17-producing T cells. *Nat Immunol* 7:929-936.
Batten et al, (2007) The biology and therapeutic potential of interleukin 27. *J Mol Med*.
Becker et al, (2005) Stepwise regulation of TH1 responses in autoimmunity: IL-12-related cytokines and their receptors. *Inflamm Bowel Dis* 11:755-764.
Brombacher et al, (2003) Novel IL-12 family members shed light on the orchestration of Th1 responses. *Trends Immunol* 24:207-212.
Chen et al, (2000) Development of Th1-type immune responses requires the type I cytokine receptor TCCR. *Nature* 407:916-920.
Dela Cruz et al. (2004) Antibody-cytokine fusion proteins: Innovative weapons in the war against cancer. *Clin. Exp. Med.* 4:57-64.
Devergne et al, (1996) A novel interleukin-12 p40-related protein induced by latent Epstein-Barr virus infection in B lymphocytes. *Journal Virology* 70:1143-1153.
Devergne et al, (1997) Epstein-Barr virus-induced gene 3 and the p35 subunit of interleukin 12 form a novel heterodimeric hematopoietin. *Proceedings National Academy Science USA* 94:12041-12046.
Diveu et al, (2008) Cytokines that regulate autoimmunity. *Curr Opin Immunol* 20:663-668.
Diveu et al, (2009) IL-27 blocks RORc expression to inhibit lineage commitment of Th17 cells. *J Immunol* 182:5748-5756.
Fitzgerald et al, (2007) Suppressive effect of IL-27 on encephalitogenic Th17 cells and the effector phase of experimental autoimmune encephalomyelitis. *J Immunol* 179:3268-3275.
Fitzgerald et al, (2007) Suppression of autoimmune inflammation of the central nervous system by interleukin 10 secreted by interleukin 27-stimulated T cells. *Nat Immunol* 8:1372-1379.
Fitzgerald et al, (2009) Therapeutic potential of IL-27 in multiple sclerosis? *Expert Opin Biol Ther* 9:149-160.
Gabay et al, (2009) The biological and clinical importance of the 'new generation' cytokines in rheumatic diseases. *Arthritis Res Ther* 11:230.
Goriely et al, (2007) The interleukin-12 family: new players in transplantation immunity? *Am J Transplant* 7:278-284.
Guo et al, (2008). The type I IFN induction pathway constrains Th17-mediated autoimmune inflammation in mice. *J Clin Invest* 118:1680-1690.
Hamano et al, (2003) WSX-1 is required for resistance to *Trypanosoma cruzi* infection by regulation of proinflammatory cytokine production. *Immunity* 19:657-667.
Hibbert et al, (2003) IL-27 and IFN-a signal via Stat1 and Stat3 and induce T-Bet and IL-12Rb2 in naive T cells. *Journal Interferon Cytokine Research* 23:513-522.
Hunter et al, (2005) New IL-12-family members: IL-23 and IL-27, cytokines with divergent functions. *Nat Rev Immunol* 5:521-531.
Kastelein et al, (2007) Discovery and biology of IL-23 and IL-27: related but functionally distinct regulators of inflammation. *Annu Rev Immunol* 25:221-242.
Lucas et al, (2003) IL-27 regulates IL-12 responsiveness of naive CD4+ T cells through Stat1-dependent and -independent mechanisms. *Proc Natl Acad Sci U S A* 100:15047-15052.
Miyazaki et al, (2008) Amelioration of delayed-type hypersensitivity responses by IL-27 administration. *Biochem Biophys Res Commun* 373:397-402.
Murphy et al, (2002) The lineage decisions of helper T cells. *Nature Reviews Immunology* 2:933-944.
Niedbala et al, (2008) Interleukin-27 attenuates collagen-induced arthritis. *Ann Rheum Dis*.
Nieuwenhuis et al, (2002) Disruption of T helper 2-immune responses in Epstein-Barr virus-induced gene 3-deficient mice. *Proceedings National Academy Science USA* 99:16951-11956.
Pflanz et al, (2002) IL-27, a heterodimeric cytokine composed of EBI3 and p28 protein, induces proliferation of naive CD4(+) T cells. *Immunity* 16:779-790.
Robinson et al, (2002) Further checkpoints in Th1 development. *Immunity* 16:755-758.
Scheller at al, (2005) No Inhibition of IL-27 signaling by soluble gp130 *Elsevier/BBRC* 326:724-728.
Shimizu et al, (2005) Membranous glomerulonephritis development with Th2-type immune deviations in MRL/lpr mice deficient for IL-27 receptor (WSX-1). *J Immunol* 175:7185-7192.
Sprecher et al, (1998) Cloning and characterization of a novel class I cytokine receptor. *Biochem Biophys Res Commun* 246:82-90.
Takeda et al, (2003) Cutting edge: Role of IL-27/WSX-1 signaling for induction of T-bet through activation of STAT1 during initial Th1 commitment. *Journal Immunology* 170:4886-4890.
Trinchieri et al, (2003) the IL-12 family of heterodimeric cytokines: new players in the regulation of T cell responses. *Immunity* 19:641-644.
Vandenbroeck et al, (2004) Inhibiting cytokines of the interleukin-12 family: recent advances and novel challenges. *J Pharm Pharmacol* 56:145-160.
Villarino et al, (2003) The IL-27R (WSX-1) is required to suppress T cell hyperactivity during infection. *Immunity* 19:645-655.
Villarino et al, (2006) IL-27 limits IL-2 production during Th1 differentiation. *J. Immunol* 176:237-247.
Yoshida et al, (2001) WSX-1 is required for the initiation of Th1 responses and resistance to L. major infection. *Immunity* 15:569-578.
Yoshida et al, (2008) Regulation of immune responses by interleukin-27. *Immunol Rev* 226:234-247.
Yoshida et al, (2009) Interleukin 27: a double-edged sword for offense and defense. *J Leukoc Biol* 86:1295-1303.
U.S. Appl. No. 12/998,799, filed Jun. 2, 2011 by Hunter, et al.
U.S. Appl. No. 10/768,744, filed Feb. 2, 2004 by Hunter, et al.

(56) References Cited

OTHER PUBLICATIONS

Illei et al. (2006) "Tocilizumab (Humanized Anti IL-6 Receptor Monoclonal Antibody) in Patients With systemic Lupis Erythematosus (SLE): Safety, Tolerability and Preliminary Efficacy." *Arthritis & Rheumatism*, 54(12): 4043.

Meda et al. (2011) "The epigenetics of autoimmunity." *Cell Molecular Immunology*, 8(3): 226-236.

Wong et al. (2008) "Hyperproduction of IL-23 and IL-17 in patients with systemic lupis erythematosus: Implications for Th17-mediated inflammation in auto-immunity." *Clinical Immunology*, 127: 385-393.

* cited by examiner

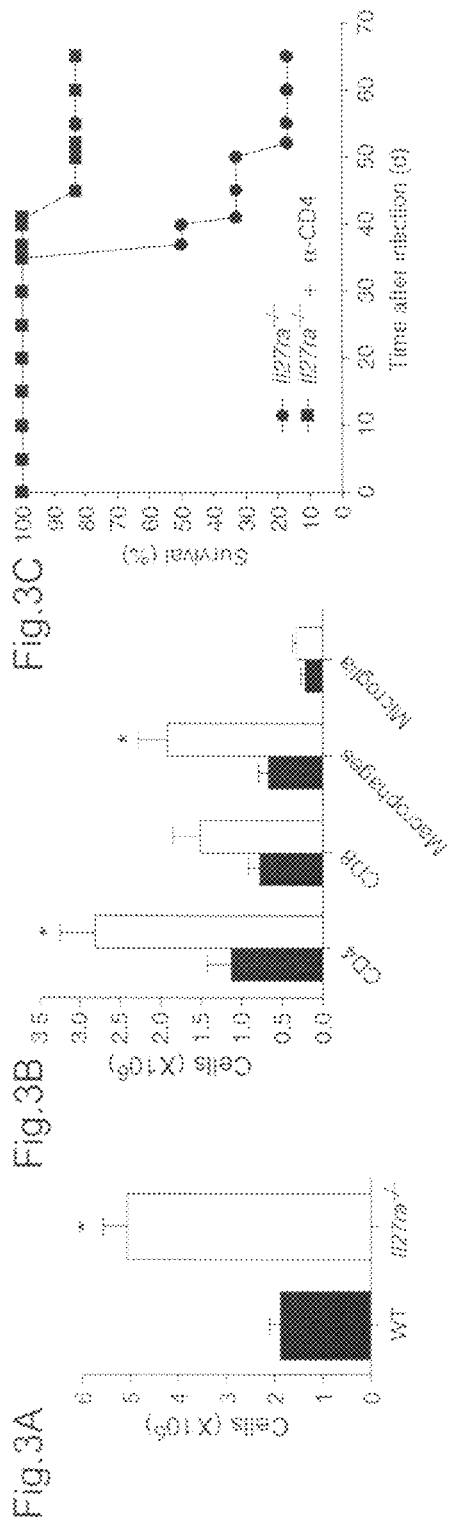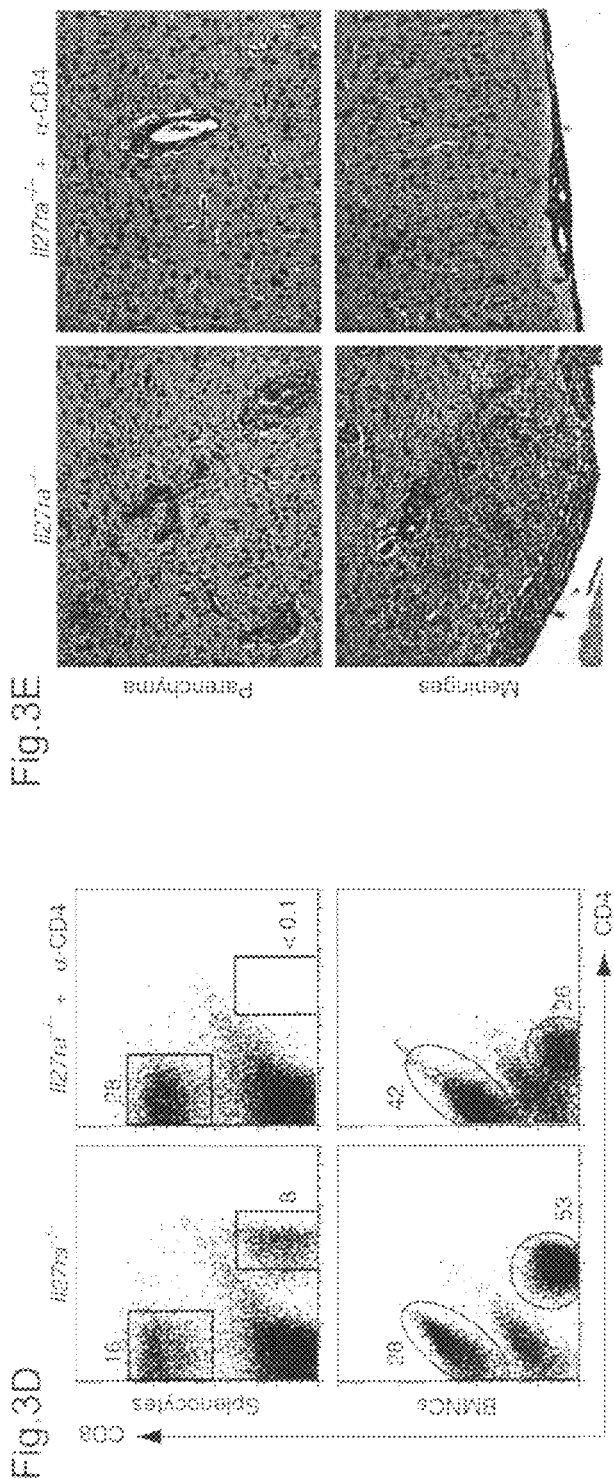

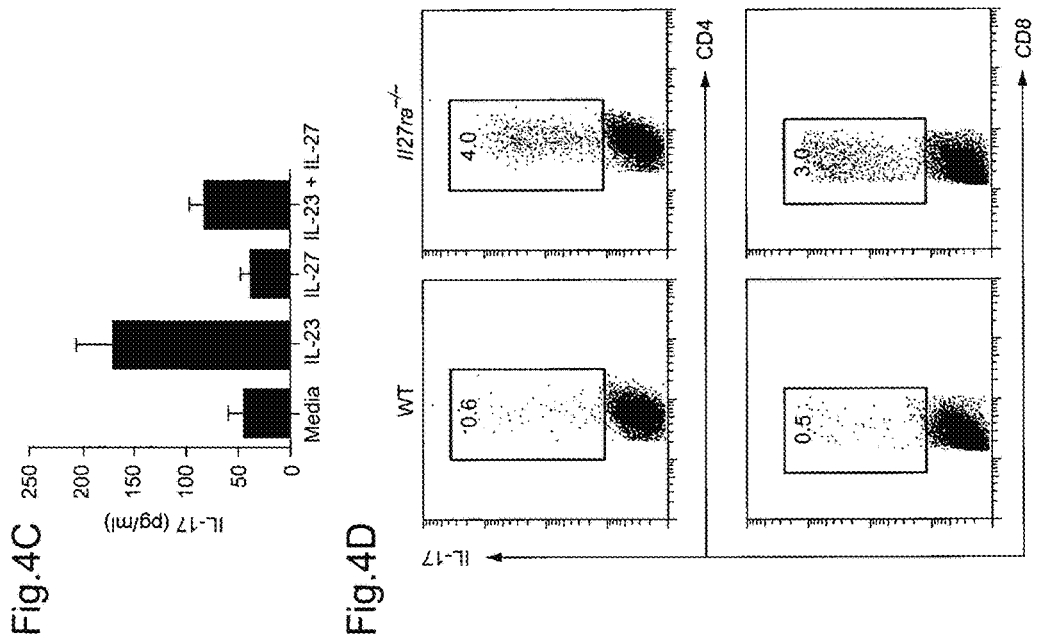
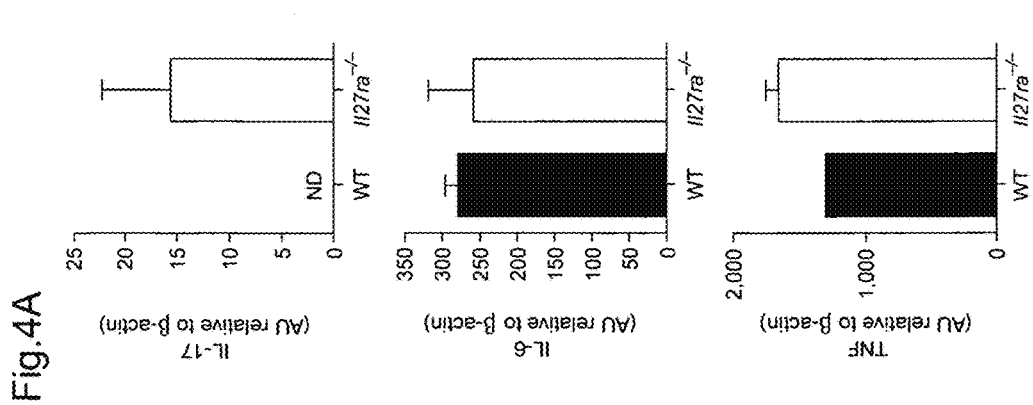
Fig.4A Fig.4B Fig.4C Fig.4D

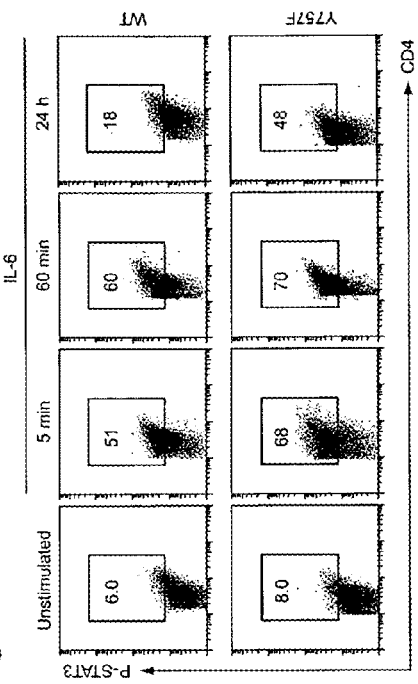
Fig.6A
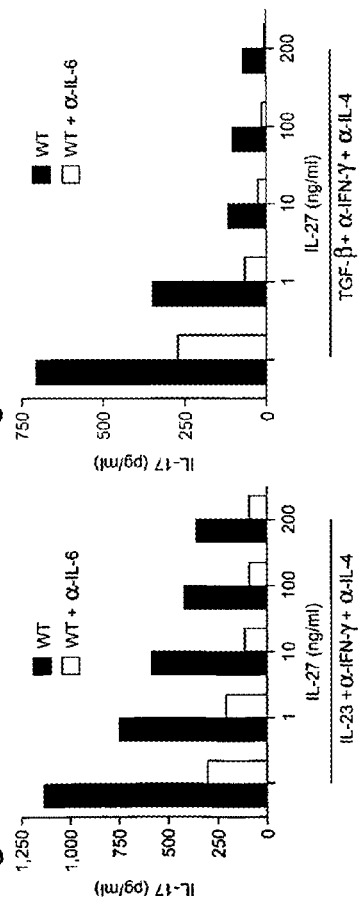
Fig.6B
Fig.6C
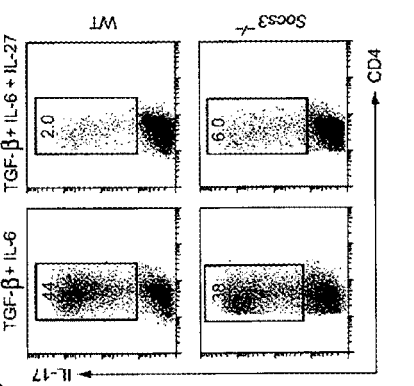
Fig.6E
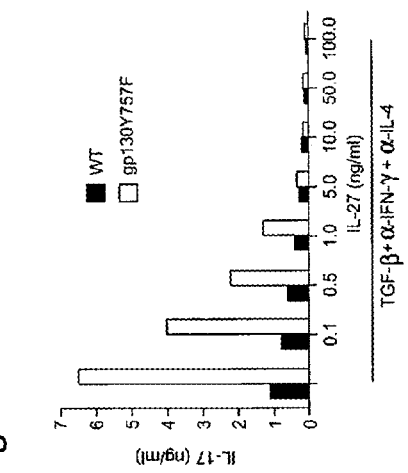
Fig.6F
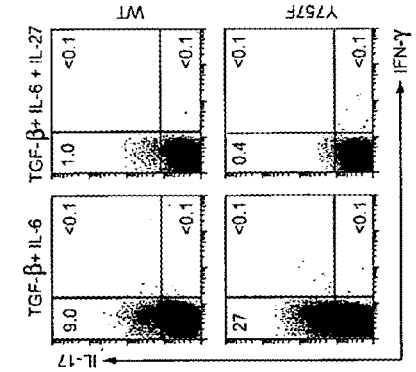
Fig.6D

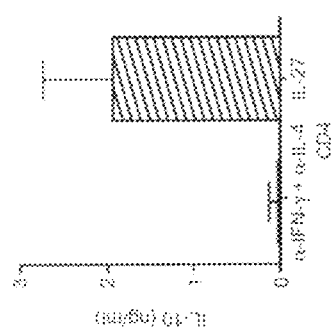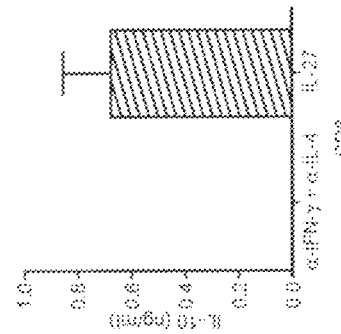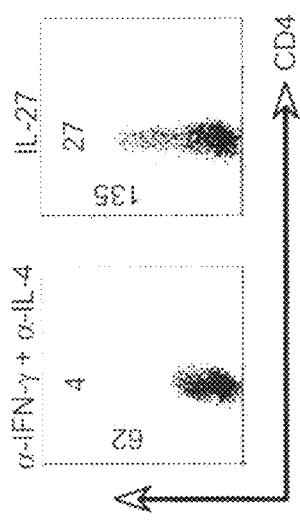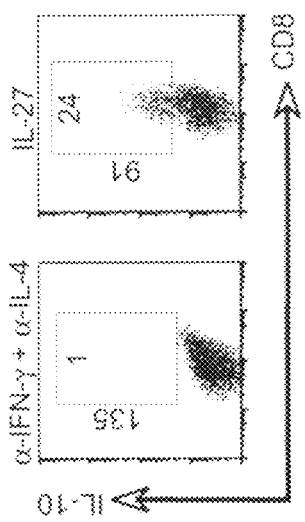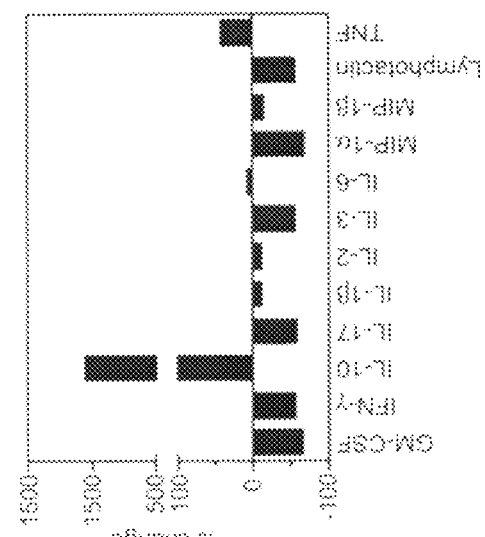

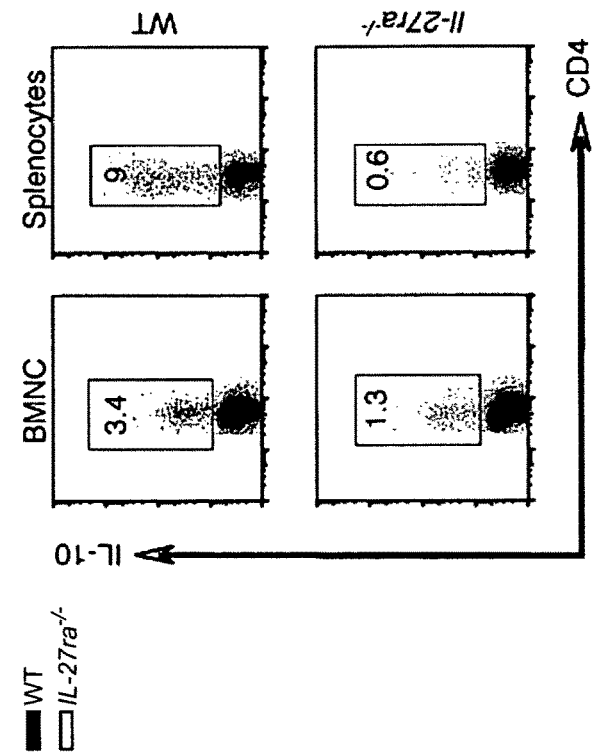
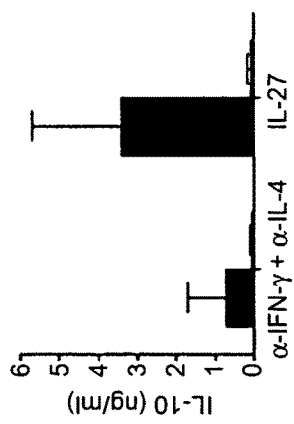
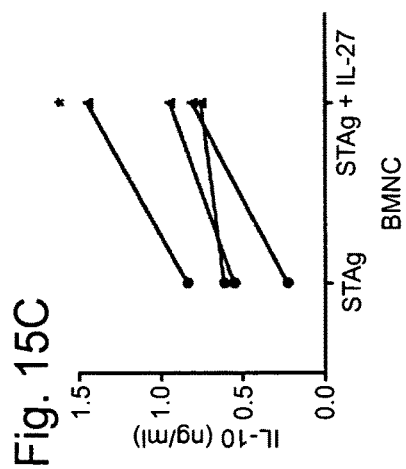
Fig. 15A
Fig. 15B
Fig. 15C

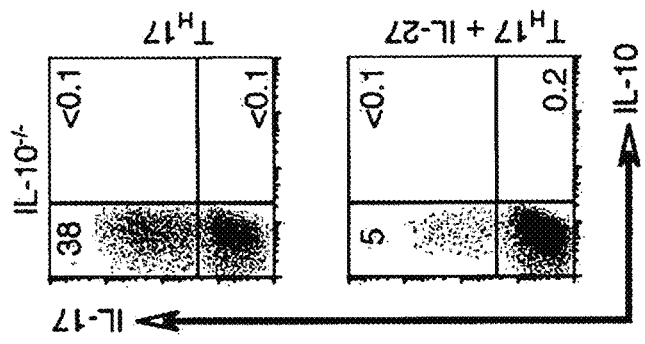
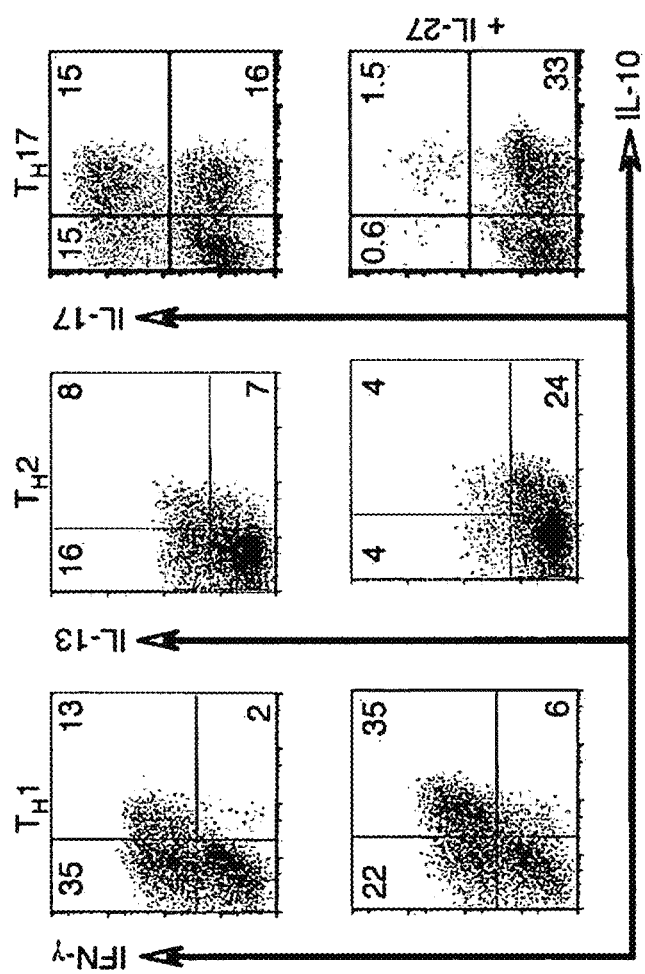
Fig. 17A
Fig. 17B

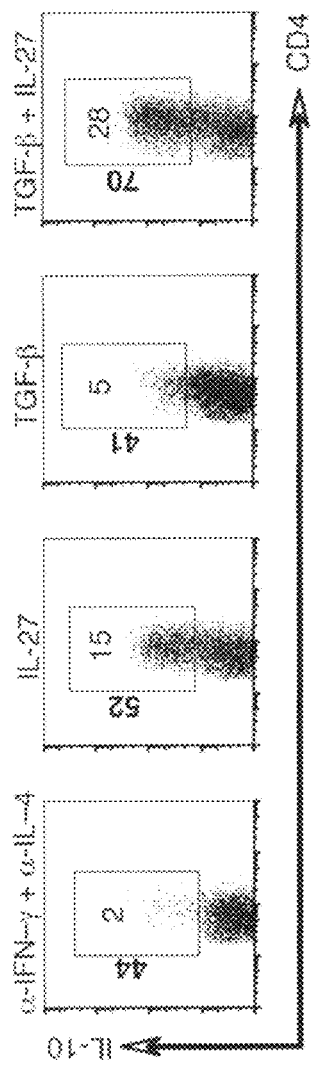
Fig. 18A
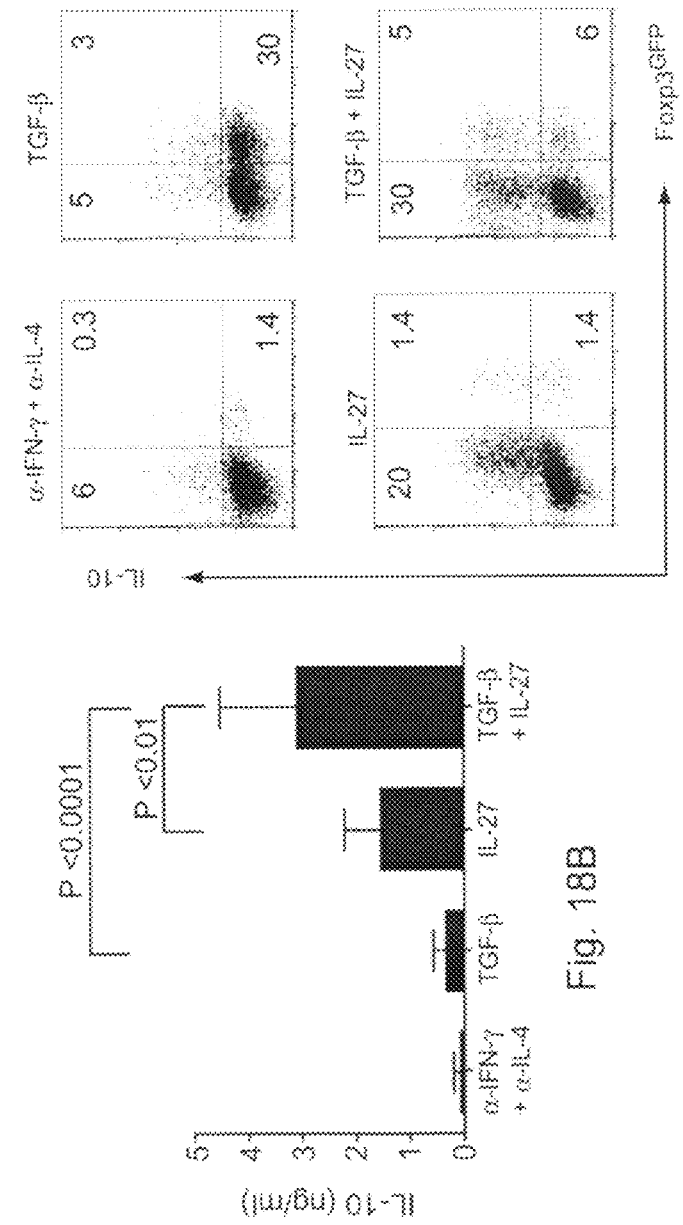
Fig. 18B
Fig. 18C

WSX-1/P28 AS A TARGET FOR ANTI-INFLAMMATORY RESPONSES

CROSS-REFERENCE TO RELATED APPLICATIONS

This application is a non-provisional utility patent application claiming priority to and benefit of the following prior provisional patent applications: U.S. Ser. No. 60/832,213, filed Jul. 19, 2006, entitled "WSX-1/P28 AS A TARGET FOR ANTI-INFLAMMATORY RESPONSES" by Christopher A. Hunter, and U.S. Ser. No. 60/837,450, filed Aug. 11, 2006, entitled "WSX-1/P28 AS A TARGET FOR ANTI-INFLAMMATORY RESPONSES" by Christopher A. Hunter, each of which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant Nos. AI42334, AI41158, and 1-T32-AI-055428 from the National Institutes of Health. The government may have certain rights to this invention.

FIELD OF THE INVENTION

The invention relates to methods of treating inflammatory conditions in mammalian subjects using various WSX-1, p28, EBI3, and gp130 polypeptides and complexes or moieties that bind to or modulate activity of such complexes. The invention also relates to isolated or recombinant complexes including soluble WSX-1 or gp130 polypeptides, isolated or recombinant WSX-1 fusion proteins, and isolated or recombinant p28 fusion proteins.

BACKGROUND OF THE INVENTION

A number of recombinant cytokines are used in a variety of clinical settings. These include interleukin-2 (IL-2), GM-CSF, IL-11, IL-12 and type I interferons (IFNs). These proteins are primarily being used as stimulators of immune cells and to act as growth factors or to enhance anti-cancer or viral responses. Few cytokines have been used to inhibit the immune system; for example, inhibition has been attempted with IL-10, which works indirectly on accessory cell functions necessary for T cell functions and which was being developed specifically with Crohn's disease and Inflammatory Bowel Disease as targets, and TGF. Success with these has been limited.

Antagonists of IL-12 p40 have been tested in clinical trials for patients with Crohn's disease with some success.

Antagonists of IL-15 are in clinical trials for arthritis based on the observation that this cytokine was involved in the development of this disease.

The IL-1 receptor antagonist is a commercially available product that is used to treat patients with rheumatoid arthritis. This is a product that blocks the interaction of the pro-inflammatory cytokine IL-1 with its receptor.

Several companies have developed antibodies/antagonists specific for the cytokine TNF-α which are currently used in the treatment of patients with rheumatoid arthritis. This approach relies on the neutralization of endogenous cytokine to prevent inflammation. A similar approach has been pursued with antibodies specific for IL-1 and IL-6. One safety issue is that these treatments are associated with the development of opportunistic infections including TB and toxoplasmosis.

SUMMARY OF THE INVENTION

WSX-1 is a recently described cytokine receptor which binds to the heterodimeric cytokine IL-27. Our studies have suggested that this cytokine/receptor pair is involved in the negative regulation of T cell mediated inflammatory responses. The identification of a role for WSX-1 in the suppression of T cell hyperactivity has clinical implications for T cell-mediated inflammatory disorders and represents a novel target for immune based therapies. Work from this laboratory has continued to focus on the inhibitory effects of IL-27 in different T cell responses, and we have made several observations that have provided new insights into the biology of this cytokine receptor system and suggested new ways to use this information to develop anti-inflammatory therapies.

It is clear from our studies that WSX-1 has a negative effect on T cell responses. IL-27 can inhibit Th1 and Th2 responses and the ability of these cells to make the T cell growth factor IL-2. In addition, IL-27 inhibits a new T cell subset—T17 (T cells that produce IL-17)—that is thought to be a major pathological T cell subset. A fusion protein, WSX-1Fc, is able to enhance the ability of IL-27 to inhibit T cell production of IL-2 and IFNγ. This implies that a shed version of this receptor may facilitate IL-27 or its individual components to signal T cells. This is in part based on the biology of the closely related cytokine/receptor component for IL-6 activity. This idea is supported by the observation that recombinant p28 (supplied by eBioscience, and also known as IL-30), while not as efficient as IL-27, is able to antagonize the production of IL-2 and IL-17. These data imply to us that p28 alone, modified, or as part of another molecule or complex that includes WSX-1, represents a useful therapeutic approach to modulate cells of the immune system. Similarly, soluble WSX-1 polypeptides and complexes also represent a useful therapeutic approach. Since IL-27 can signal through a receptor complex including both WSX-1 and gp130, soluble gp130 polypeptides and complexes represent yet another useful therapeutic approach.

Accordingly, one general class of embodiments provides a composition comprising an isolated or recombinant soluble WSX-1/p28 polypeptide complex, an isolated or recombinant soluble WSX-1/EBI3 polypeptide complex, an isolated or recombinant soluble WSX-1/IL-27 complex, an isolated or recombinant soluble gp130/p28 polypeptide complex, an isolated or recombinant soluble gp130/EBI3 polypeptide complex, an isolated or recombinant soluble gp130 IL-27 complex, or a variant thereof.

In one aspect, the composition is anti-inflammatory. The composition optionally includes a pharmaceutically acceptable excipient, for example, in embodiments in which the composition is to be administered to a subject. In one embodiment, the composition suppresses development of IL-17 cells from naïve T cells induced by IL-6 and transforming growth factor beta.

The composition can include one or more cell, for example, one or more T cell, B cell, mast cell, neutrophil, macrophage, dendritic cell, or other cell expressing gp130 or WSX-1. The complex can affect a function or activity of the cell. In one embodiment, the composition includes a T-cell, and the composition alters a function or activity of the T-cell. For example, the T-cell can display altered expression of IL-2, IFN-gamma, TNF-alpha, IL-6, IL-4, IL-13, IL-17, IL-25, IL-10, IL-5, or CD25, altered proliferation, or altered survival. The composition optionally includes transforming growth factor beta.

Another general class of embodiments provides a recombinant or isolated WSX-1 fusion protein. The fusion protein includes a WSX-1 polypeptide, which can be, e.g., at the N-terminus of the fusion protein, at the C-terminus of the fusion protein, or internal to the fusion protein. The WSX-1 polypeptide can include the extracellular domain, or a subsequence thereof, of a naturally occurring WSX-1 (e.g., human WSX-1) or a variant thereof.

In one class of embodiments, the fusion protein comprises one or more domains that recognize a cell-specific marker, for example, one or more antibody domains that recognize the marker. Exemplary markers include CD4, CD8, CD11c, CD11b, and NK1.1. In one class of embodiments, the fusion protein comprises one or more polypeptide domains derived from p28 or EBI3.

Yet another general class of embodiments provides a recombinant or isolated p28 fusion protein. The fusion protein includes a p28 polypeptide, which can be, e.g., at the N-terminus of the fusion protein, at the C-terminus of the fusion protein, or internal to the fusion protein. The p28 polypeptide can be derived from a naturally occurring p28 (e.g., human p28) or a variant thereof.

The fusion protein optionally comprises one or more antibody domains. For example, the fusion protein can include one or more antibody domains that recognizes a cell-specific marker, e.g., CD4, CD8, CD11c, CD11b, or NK1.1.

Polynucleotides encoding WSX-1 and p28 fusion proteins are another feature of the invention. For example, one class of embodiments provides a nucleic acid that encodes a recombinant or isolated WSX-1 fusion protein, wherein the fusion protein comprises one or more domains that recognize a cell-specific marker or one or more polypeptide domains derived from p28 or EBI3. The nucleic acid optionally encodes one or more polypeptide domains selected from: an antibody domain, an Fc region, a p28 domain, or an EBI3 domain, as well as encoding a WSX-1 polypeptide. Another class of embodiments provides a nucleic acid that includes a recombinant or isolated p28 fusion protein.

Antibodies that bind to polypeptides and complexes of the invention are also a feature of the invention. Thus, one class of embodiments provides an antibody that specifically binds to a soluble WSX-1 polypeptide, a soluble WSX-1/p28 polypeptide complex, or to a soluble WSX-1/IL-27 polypeptide complex. The antibody optionally potentiates an activity of the polypeptide or polypeptide complex.

One aspect of the invention provides methods of treating an inflammatory condition in a mammalian subject, e.g., a human subject. Exemplary inflammatory conditions to be treated include, but are not limited to, an immune disorder (e.g., an autoimmune disease); an infection; cancer, such as multiple myeloma and myelogenous and other leukemias, as well as tumor metastasis; an allergy; arthritis; asthma; inflammatory bowel disease, such as ulcerative colitis or Crohn's disease; uveitis; psoriasis; lupus; multiple sclerosis; a chronic infectious disease; tuberculosis; ankalyzing spondalitis; transplant rejection; sarcoidosis; hepatitis; inflammation of the central nervous system; Acquired Immune Deficiency Syndrome; acute pancreatitis; Addison's disease; alcohol-induced liver injury including alcoholic cirrhosis; Alzheimer's disease; amyelolateroschlerosis; asthma and other pulmonary diseases; atherosclerosis; autoimmune vasculitis; autoimmune hepatitis-induced hepatic injury; biliary cirrhosis; cachexia/anorexia, including AIDS-induced cachexia; chronic fatigue syndrome; *Clostridium* associated illnesses, including *Clostridium*-associated diarrhea; coronary conditions and indications, including congestive heart failure, coronary restenosis, myocardial infarction, myocardial dysfunction, and coronary artery bypass graft; diabetes, including juvenile onset Type 1, diabetes mellitus, and insulin resistance; endometriosis, endometritis, and related conditions; epididymitis; erythropoietin resistance; fever; fibromyalgia or analgesia; glomerulonephritis; graft versus host disease/transplant rejection; Graves' disease; Guillain-Barre syndrome; Hashimoto's disease; hemolytic anemia; hemorrhagic shock; hyperalgesia; inflammatory conditions of a joint and rheumatic diseases including, osteoarthritis, rheumatoid arthritis, juvenile (rheumatoid) arthritis, seronegative polyarthritis, ankylosing spondylitis, Reiter's syndrome and reactive arthritis, Still's disease, psoriatic arthritis, enteropathic arthritis, polymyositis, dermatomyositis, scleroderma, systemic sclerosis, vasculitis (e.g., Kawasaki's disease), cerebral vasculitis, Lyme disease, staphylococcal-induced arthritis, Sjogren's syndrome, rheumatic fever, polychondritis and polymyalgia rheumatica and giant cell arteritis; inflammatory eye disease, as may be associated with, for example, corneal transplant; inflammatory eye disease, as may be associated with, e.g., corneal transplant; inflammatory bowel disease; ischemia, including cerebral ischemia; Kawasaki's disease; learning impairment; lung diseases; lupus nephritis; multiple sclerosis; myasthenia gravis; myopathies; neuroinflammatory diseases; neurotoxicity; ocular diseases and conditions, including ocular degeneration and uveitis; osteoporosis; pain, including cancer-related pain; Parkinson's disease; pemphigus; periodontal disease; Pityriasis rubra pilaris; pre-term labor; prostatitis and related conditions; psoriasis and related conditions; psoriatic arthritis; pulmonary fibrosis; reperfusion injury; rheumatic fever; rheumatoid arthritis; sarcoidosis; scleroderma; septic shock; side effects from radiation therapy; Sjogren's syndrome; sleep disturbance; spondyloarthropathies; systemic lupus erythematosus; temporal mandibular joint disease; thyroiditis; tissue transplantation or an inflammatory condition resulting from strain, sprain, cartilage damage, trauma, and orthopedic surgery; vasculitis; or an inflammatory condition resulting from strain, sprain, cartilage damage, trauma, orthopedic surgery, infection or other disease processes.

In one class of embodiments, the methods include administering to the subject an isolated or recombinant moiety selected from the group consisting of a soluble WSX-1 polypeptide, a p28 polypeptide, a soluble WSX-1/p28 polypeptide complex, a soluble WSX-1/EBI3 polypeptide complex, a soluble WSX-1/IL-27 polypeptide complex, a soluble gp130/IL-27 complex, a soluble gp130/p28 polypeptide complex, a soluble gp130/EBI3 polypeptide complex, a p28 polypeptide and a soluble WSX-1 polypeptide, an EBI3 polypeptide and a soluble WSX-1 polypeptide, IL-27 and a soluble WSX-1 polypeptide, a soluble gp130 polypeptide and a p28 polypeptide, a soluble gp130 polypeptide and IL-27, a soluble gp130 polypeptide and a EBI3 polypeptide, and a variant thereof. In embodiments in which a combination of recombinant or isolated polypeptides are administered (e.g., a p28 polypeptide and a soluble WSX-1 polypeptide), the polypeptides can but need not form a complex, and the polypeptides can be co-administered or separately administered. The methods optionally include diagnosing the patient with the inflammatory condition prior to said administering. The isolated or recombinant moiety is optionally administered to the subject in combination with a second compound, for example, transforming growth factor beta.

In another class of embodiments, the methods include administering to the subject a moiety that specifically binds to or modulates an activity of a gp130/WSX-1IL-27 complex, or that modulates formation of the complex in a cell, thereby treating the subject for the condition. The moiety can be, for example, an antibody, an antagonist, an agonist, and an activity modulator.

In another aspect, the invention provides methods of identifying a compound that binds to or modulates an activity of a soluble WSX-1 polypeptide, a soluble WSX-1/p28 polypeptide complex, a soluble WSX-1/IL-27 polypeptide complex, a soluble WSX-1/EBI3 polypeptide complex, a soluble gp130/p28 polypeptide complex, a soluble gp130/IL-27 polypeptide complex, or a soluble gp130/EBI3 polypeptide complex. In the methods, a biological or biochemical sample comprising the polypeptide or complex is contacted with a test compound. Binding of the test compound to the polypeptide or complex or modulation of the activity of the polypeptide or complex by the test compound is detected, thereby identifying the compound that binds to or modulates the activity of the polypeptide or complex. The compound optionally potentiates inhibition of a T cell response by the polypeptide or complex, potentiates antagonist activity against IL-2 or IL-17, or alters T cell proliferation, survival, or expression of IL-2, IFN-gamma, TNF-alpha, IL-6, IL-4, IL-13, IL-17, IL-25, IL-10, IL-5, or CD25.

BRIEF DESCRIPTION OF THE DRAWINGS

FIG. 3 Panels A-E illustrate that depletion of CD4+ T cells rescues Il27ra−/− mice and reduces inflammation in the brain. Panel A presents a bar graph of total BMNC harvested from groups of 4-5 chronically infected Il27ra−/− and WT mice. Results are representative of three independent experiments. Panel B presents a bar graph of CD4+ T cells, CD8+ T cells, macrophages and microglia. The percentage of CD4+ T cells, CD8+ T cells, macrophages and microglia in each BMNC preparation, as determined by flow cytometry, were used to calculate the total number of cells in each population. Bars are colored as in Panel A. Results are representative of two independent experiments with groups of 4-5 mice. Panel B presents a line graph showing survival of Il27ra−/− mice infected with 20 Me49 cysts and, at day 5 after infection, treated with sulfadiazine for 2 weeks to control parasite replication; at four weeks depletion of CD4+ T cells was started. Data represent two independent experiments with three mice per group. Panel D illustrates flow cytometry on BMNC or splenocytes isolated and stained for CD4 and CD8 to quantify the success of CD4 depletion in the brain. Panel E presents photographs of brain sections, taken at day 35 after infection for histology. * denotes a P value ≤0.05.

FIG. 4 Panels A-D illustrate that IL-27 inhibits production of IL-17 in the brain of mice chronically infected with *T. gondii*. Panel A presents bar graphs of quantitative real-time PCR for mRNAs for IL-17, IL-6 and TNF in the brain of chronically infected Il27ra−/− and WT mice (Day 30 after infection). Data are representative of two independent experiments. Panel B presents bar graphs of ELISA assay on supernatants from BMNC isolated from WT or Il27ra−/− mice restimulated in vitro in the presence of STAg for 48 hrs and evaluated for IL-17, IL-6 and TNF. Results are representative of four independent experiments with similar results and the error bars designating the SEM. Panel C presents a bar graph of ELISA assay on supernatants from BMNC isolated from WT mice and restimulated with STAg in the presence or absence of IL-23, IL-27 or IL-23 and IL-27 for 48 hrs. Results are representative of two independent experiments with similar results and the error bars represent the SEM. Panel D illustrates flow cytometry of BMNC from WT and Il27ra−/− mice stimulated for 2 hrs ex vivo with PMA and iononmycin in the presence of BFA and stained intracellularly for IL-17. Results are representative of two independent experiments with similar results. ND, not detected.

FIG. 6 Panels A-F illustrate that IL-27 mediated inhibition of IL-17 production by T cells is independent of SOCS3. Panels A and B present bar graphs of ELISA assay on supernatants from CD4+ T cells isolated from C57BL/6 mice grown under T$_H$-17-inducing conditions with increasing concentrations of IL-27 in the presence or absence of anti-IL-6 antibody for IL-17 production. Panel C illustrates flow cytometry on purified CD4+ T cells from gp130Y757F mice or WT littermate controls stained for intracellular P-STAT3 following stimulation with IL-6 (5 min, 60 min or 24 hr). Panel D illustrates flow cytometry on CD4+ T cells isolated from gp130Y757F mice or WT littermate controls and stimulated with anti-CD3 and anti-CD28 under T$_H$-17-inducing conditions in the presence or absence of IL-27 four days prior to staining for intracellular IL-17 and IFN-γ. Panel E presents a bar graph of ELISA assay on supernatants from CD4+ T cells from gp130Y757F or WT littermate controls grown under the T$_H$-17-inducing conditions in the presence of increasing amounts of IL-27 for IL-17 production. Panel F illustrates flow cytometry of Socs3−/− CD4+ T cells isolated from CreMMTVSocs3fl/fl mice activated to induce production of IL-17 in the presence or absence of IL-27 before staining for intracellular IL-17. Plots are gated on CD4+ T cells; numbers in quadrants represent the frequency in each. Data are representative of three independent experiments. Error bars represent the SEM.

Figure 7B:
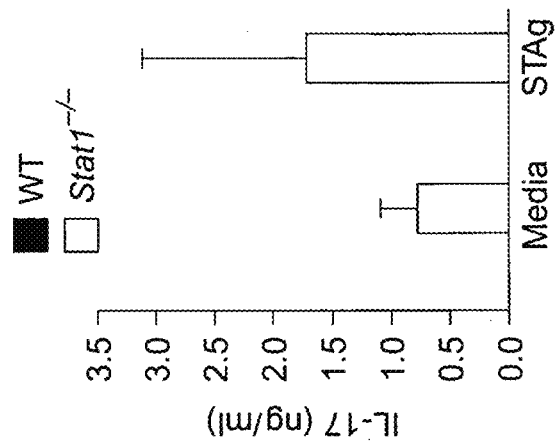
Figure 7A:
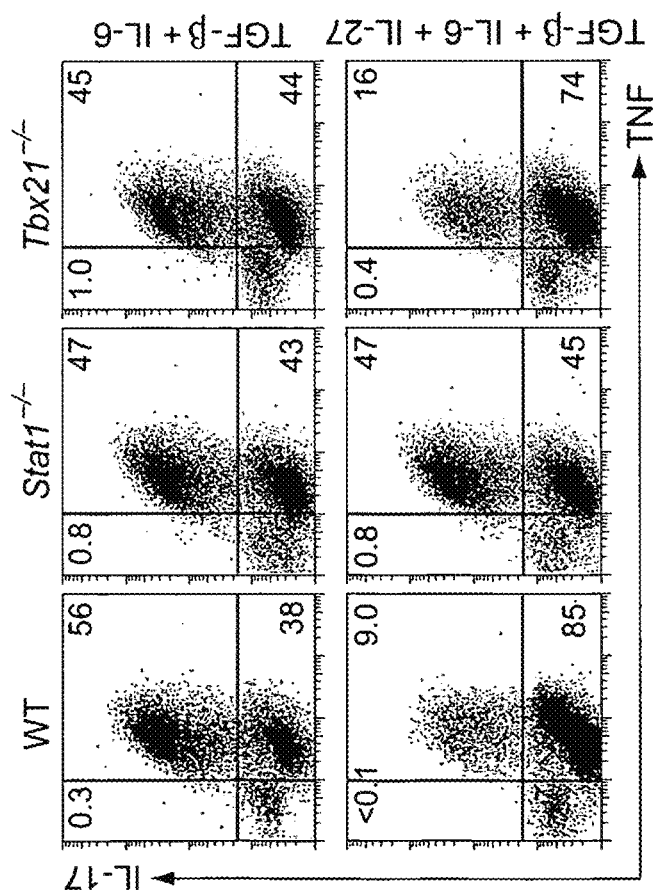

FIG. 7 Panels A-B illustrate that IL-27 mediated inhibition of IL-17 production by T cells is dependent on STAT1 but not T-bet. Panel A illustrates flow cytometry on CD4+ T cells isolated from CD57BL/6, Stat1−/−, or Tbx21−/− mice and activated with anti-CD3 and anti-CD28 under T$_H$-17-inducing conditions in the presence or absence of IL-27 and then stained for intracellular IL-17 and TNF. Data represent three independent experiments. Panel B presents a bar graph of ELISA assay on supernatants of splenocytes isolated from C57BL/6 (n=3) or Stat1−/− (n=3) mice seven days after intraperitoneal infection with 20 cysts from the Me49 strain of T. gondii and restimulated for 48 hrs in the presence or absence of STAg for IL-17 production. Plots are gated on CD4+ T cells; numbers in quadrants represent the frequency in each. Error bars denote the SEM.

Figure 8:
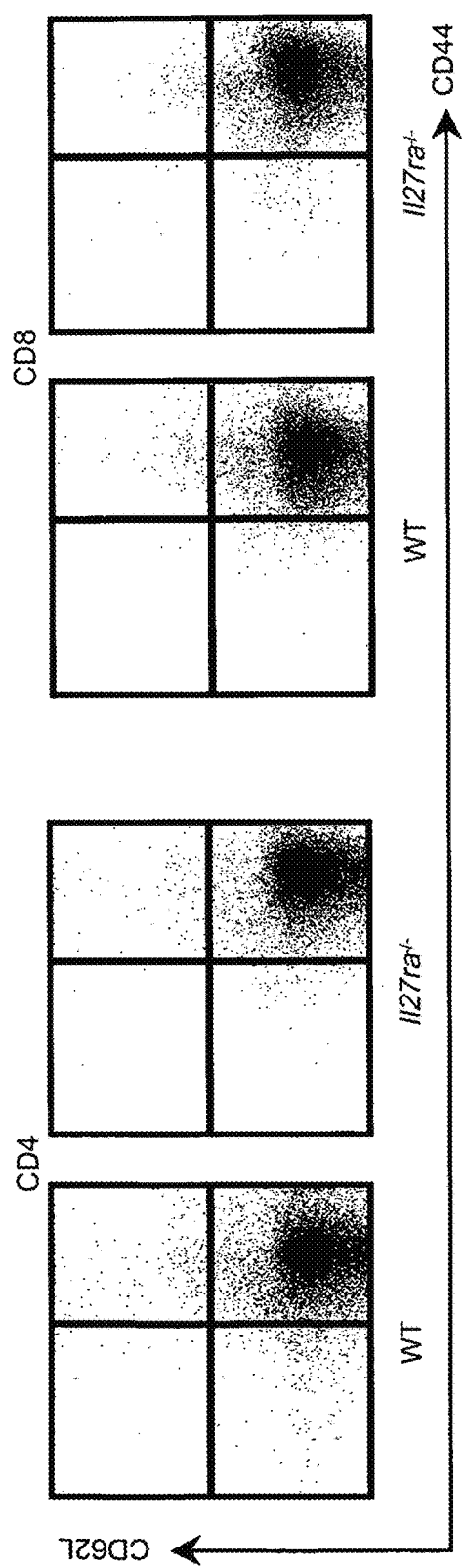

FIG. 8 presents flow cytometry data illustrating that T cells isolated from the brains of chronically infected Il27ra−/− and WT mice display an activated phenotype. BMNC were isolated from chronically infected Il27ra−/− and WT mice. The CD4+ and CD8+ T cells were stained for the activation markers CD44 and CD62L. Plots are gated on CD4+ or CD8+ T cells where indicated. Data are representative of three independent experiments.

Figure 9:
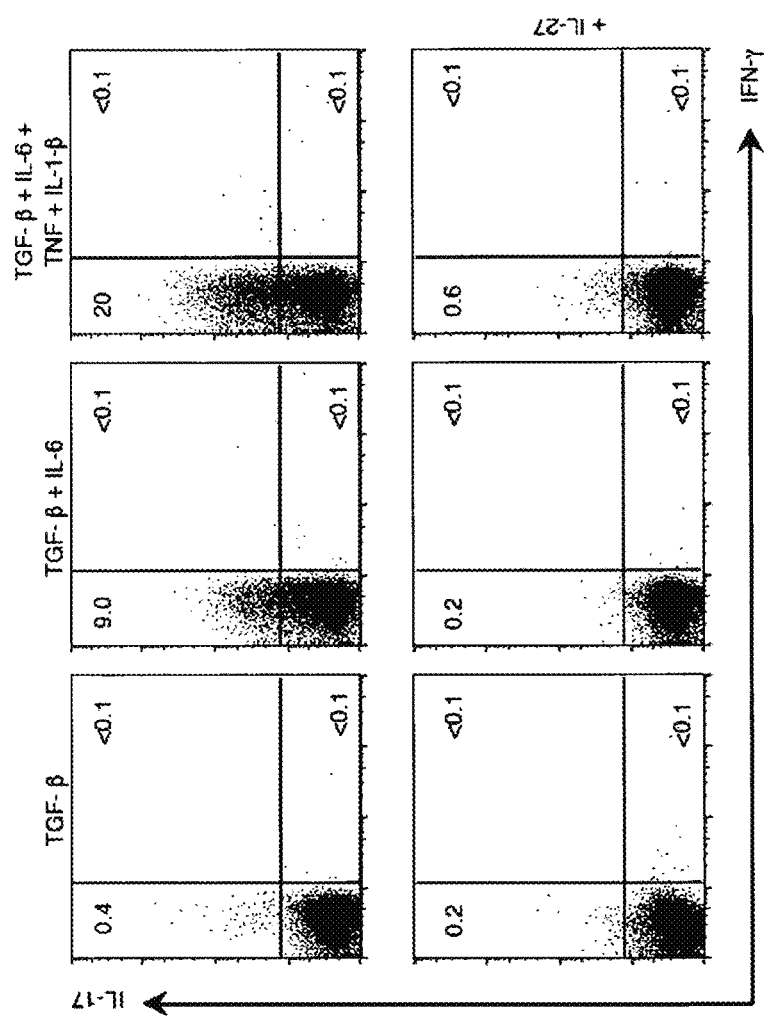

FIG. 9 presents flow cytometry data illustrating that IL-27 inhibits IL-17 production by CD4+ T cells without stimulation with PMA and ionomycin. CD4+ T cells isolated from C57BL/6 mice were activated with α-CD3 and α-CD28 under non-polarizing conditions (anti-IFN-γ, anti-IL-4). TGF-β alone or in combination with IL-6 or IL-6, IL-1-β, TNF were used to generate T$_H$-17 cells in the presence or absence of IL-27. Cells were stained for intracellular IL-17 and IFN-γ without PMA and ionomycin stimulation on day four. Plots are gated on CD4+ T cells; numbers in quadrants represent the frequency of cells in each. Data are representative of two independent experiments.

Figure 10:
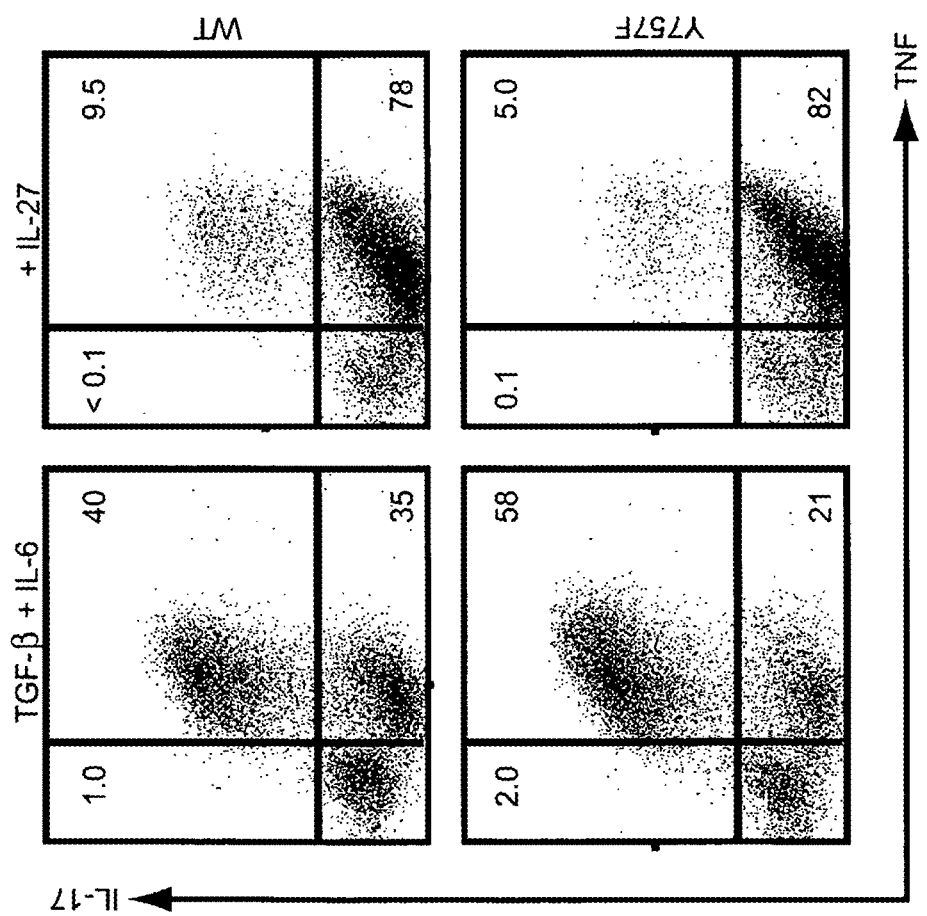

FIG. 10 presents flow cytometry data illustrating that IL-27 inhibition of IL-17 production by T cells is independent of SOCS3. CD4+ T cells from gp130Y757F mice or WT littermate controls were grown under T$_H$-17-inducing conditions in the presence or absence of IL-27. However, in this experiment the T cells were stimulated with PMA and ionomycin plus BFA for 4 hrs on day 4 prior to staining for intracellular IL-17 and TNF. Plots are gated on CD4+ T cells; numbers in quadrants represent the frequency of cells in each. Data are representative of three independent experiments.

Figure 11:
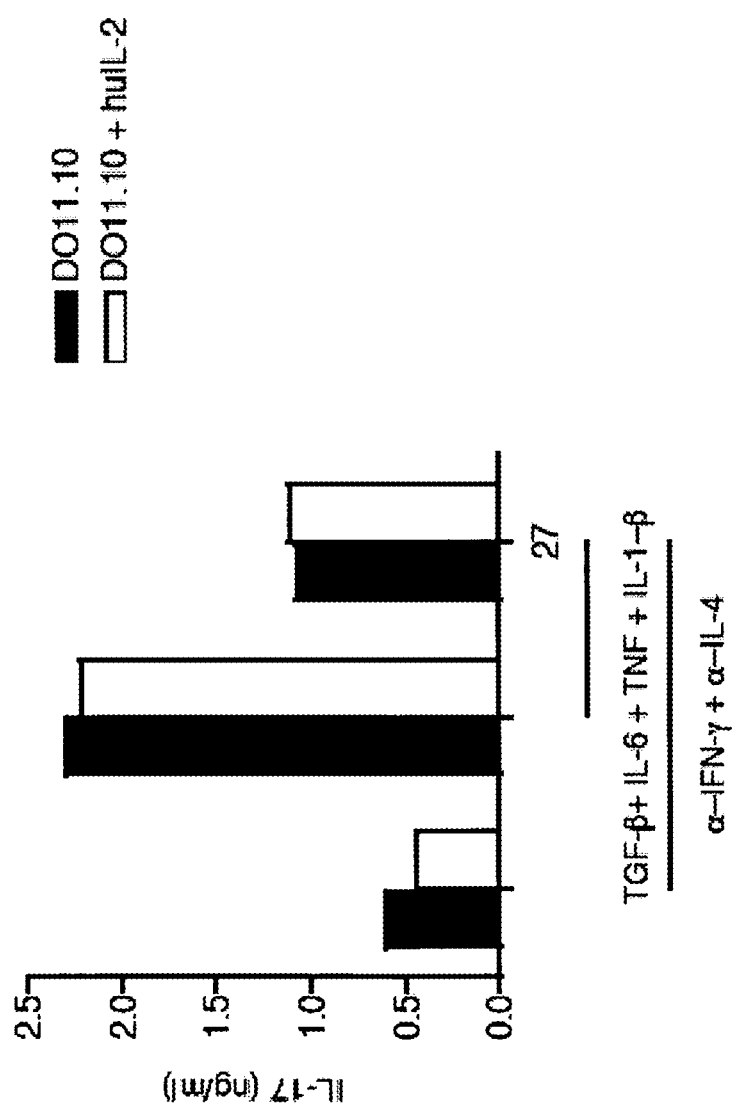
Figure 12A:
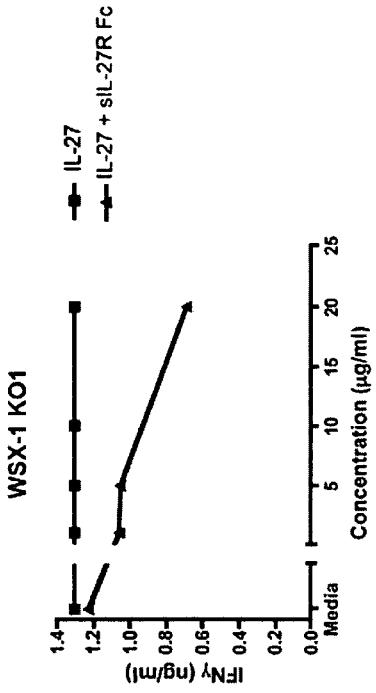
Figure 12B:
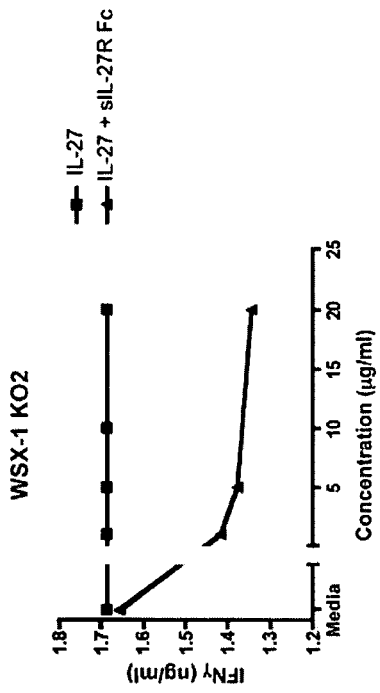
Figure 12C:
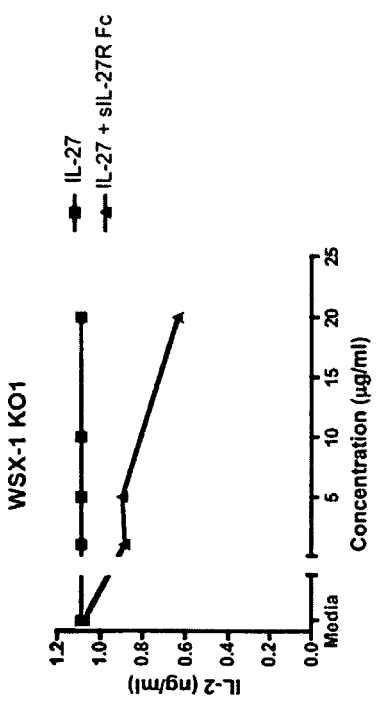
Figure 12D:
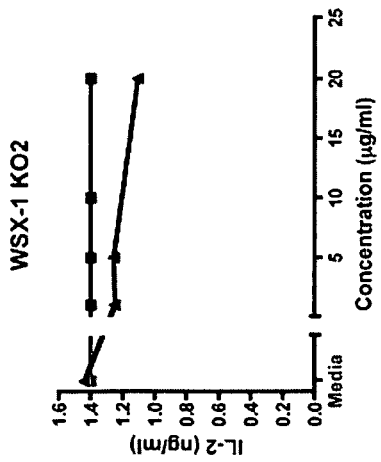

FIG. 11 presents a bar graph of IL-17 levels, showing that IL-27 inhibition of IL-17 occurs independently of its ability to inhibit IL-2 production. CD4+ T cells isolated from transgenic DO11.10 mice were activated with ovalbumin peptide under T$_H$-17-inducing conditions in the presence or absence of IL-27. Cells were cultured for four days in the presence or absence of human IL-2 before analyzing the cellular supernatants for IL-17 by ELISA. Data are representative of two independent experiments.

FIG. 12, panels A-D, presents line graphs of IL-2 (Panels A and C) and IFNγ (Panels B and D) levels, illustrating that inhibition of IL-2 and IFNγ production by IL-27 is potentiated by a soluble WSX-1 polypeptide in CD4+ T cells from WSX-1 knockout mice.

Figures 13A, 13B, 13C:
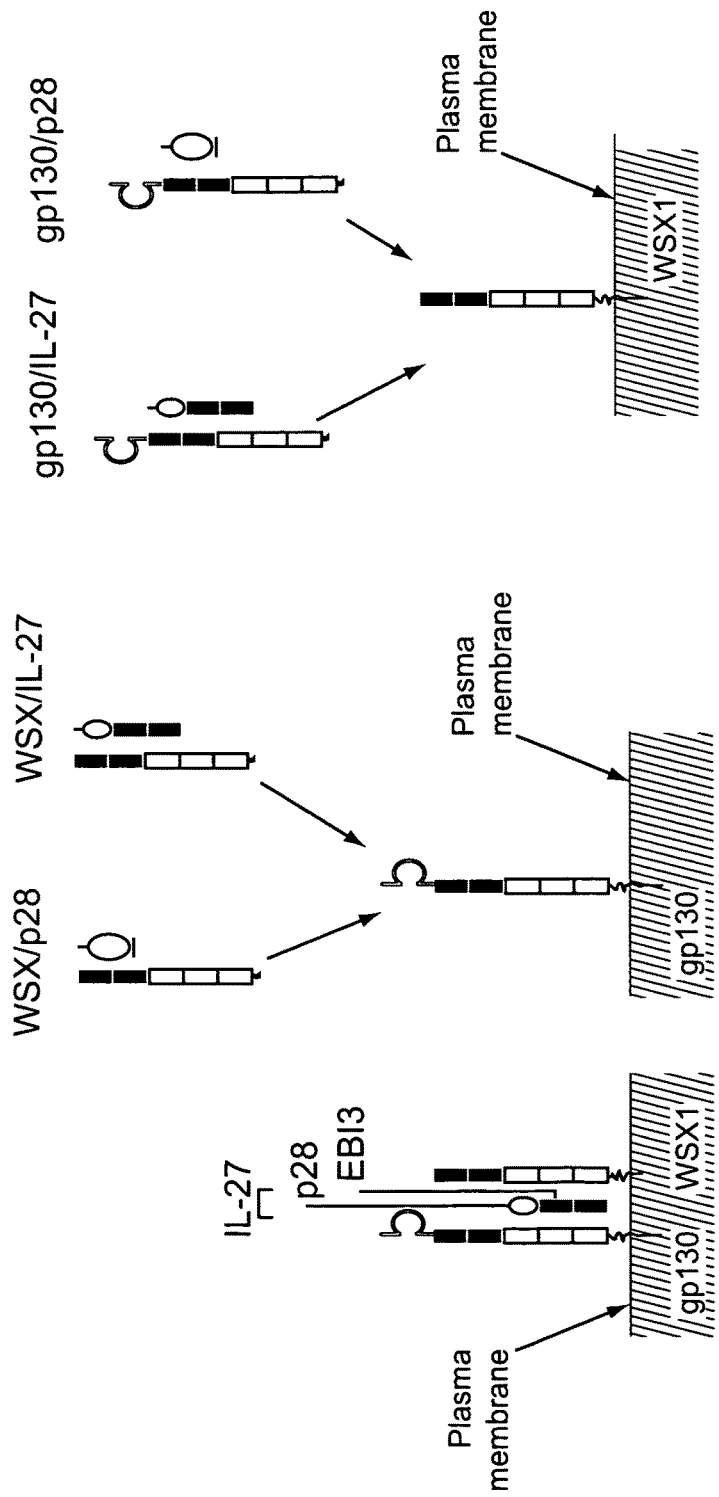

FIG. 13 Panels A-C schematically illustrate strategies for modulating the inflammatory response by modulating signaling through the IL-27 receptor or its components WSX-1 and gp130. Panel A schematically depicts signaling through the IL-27 receptor by IL-27 (a heterodimer of EBI3 and p28). Panel B schematically illustrates signaling through gp130 by a soluble WSX-1/p28 complex or a soluble WSX-1/IL-27 complex. Panel C schematically illustrates signaling through WSX-1 by a soluble gp130/p28 complex or a soluble gp130/IL-27 complex.

FIG. 14 Panels A-E illustrate that IL-27 promotes IL-10 production by CD4+ and CD8+ T cells. Panel A presents a bar graph showing results of the RodentMAP™ bioassay, which are expressed as the percent change between cells cultured under non-polarizing conditions and those stimulated with IL-27. Panels B and C illustrate production of IL-10 by CD4+ T cells (Panels B and D) and CD8+ T cells (Panels C and E) as measured by flow cytometry (Panels B and C) and ELISA (Panels D and E) of 72 h culture supernatants (error bars, s.d.). T cells were isolated from the spleen and lymph nodes of C57BL/6 mice and activated with anti-CD3 and anti-CD28 under non-polarizing conditions in the presence or absence of IL-27. CD4+ and CD8+ T cells cultured for 4 d and 3 d, respectively, were stimulated for 4 h with PMA and ionomycin in the presence of brefeldin A before staining for intracellular IL-10. Numbers in boxes indicate percent IL-10+ cells. Bold numbers represent the mean fluorescent intensity (MFI). Results in Panels B and C are representative of three independent experiments with similar results.

FIG. 15 Panels A-C illustrate that production of IL-10 is reduced in the absence of IL-27R signaling. Panel A presents a bar graph of ELISA of IL-10 in the supernatants from CD4+ T cells isolated from wild-type C57BL/6 (WT) or Il-27ra−/− mice; cells were grown under non-polarizing conditions in the presence or absence of IL-27. Results are representative of three independent experiments with similar results (error bars, s.d.). Panel B illustrates flow cytometry of BMNCs and spleens from WT and Il-27ra−/− mice chronically infected with T. gondii; cells were stimulated 5 h ex vivo with PMA and ionomycin in the presence of brefeldin A and stained intracellularly for IL-10. Numbers in the boxes indicate percent IL-10+ cells. Results are representative of three independent experiments with similar results. Panel C presents a line graph of ELISA of IL-10 in supernatants from WT BMNCs (n=4) restimulated for 48 h in vitro with soluble toxoplasma antigen (STAg) in the presence or absence of IL-27. Error bars, s.d. *, P=0.0275.

Figure 16A:
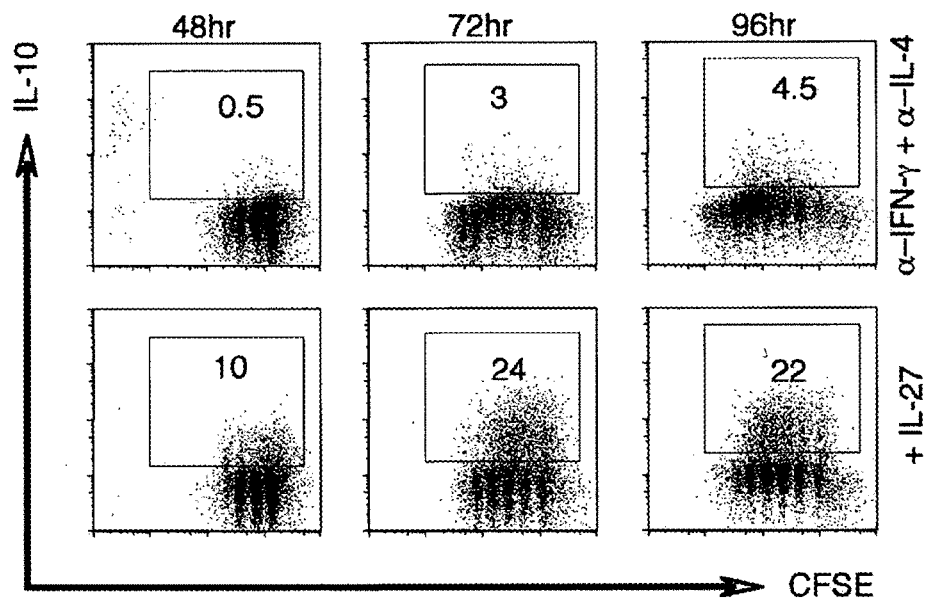
Figure 16B:
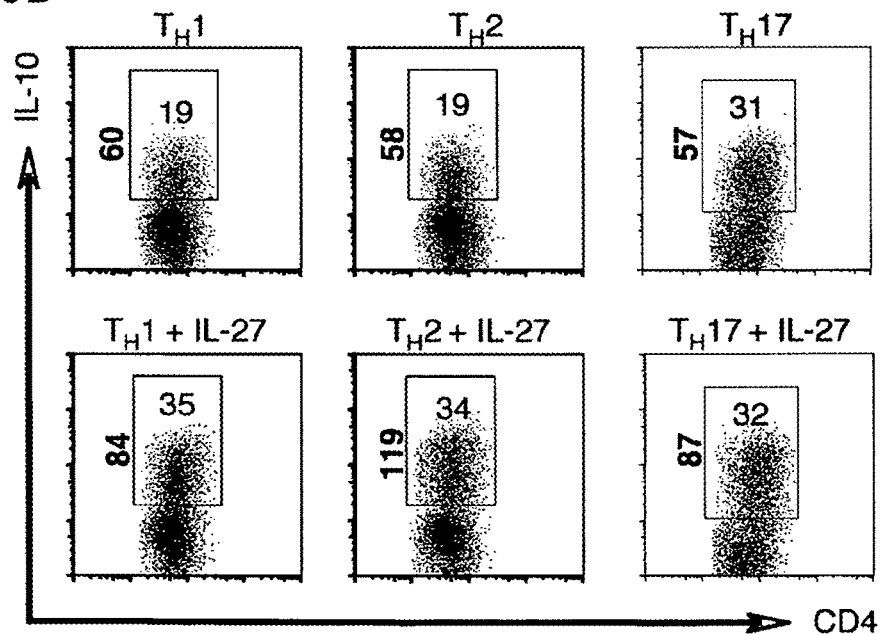
Figure 19A:
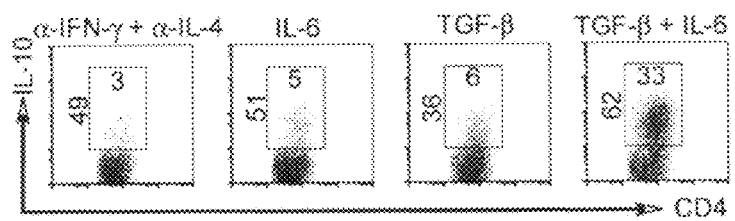
Figure 19B:
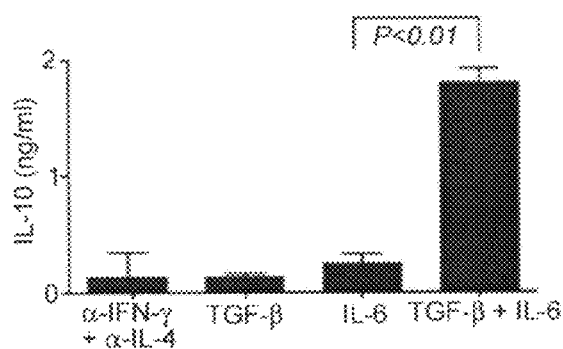
Figure 19C:
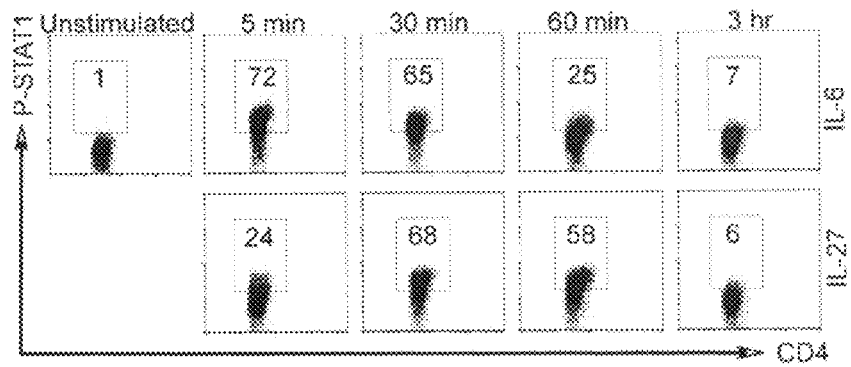
Figure 19D:
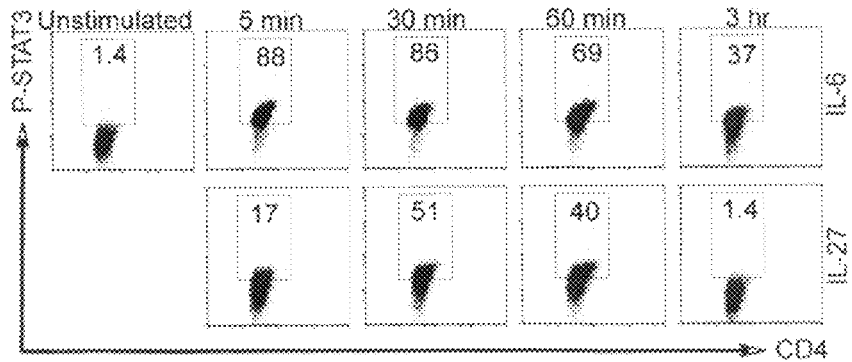
Figure 20A:
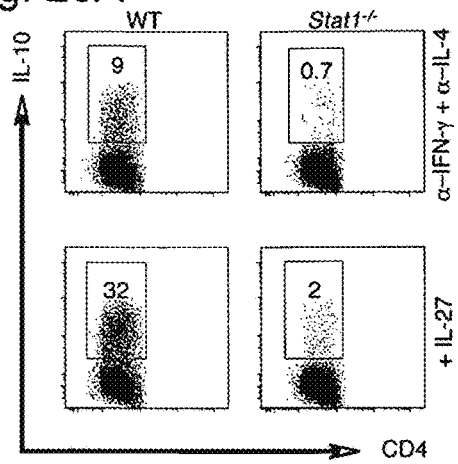
Figure 20B:
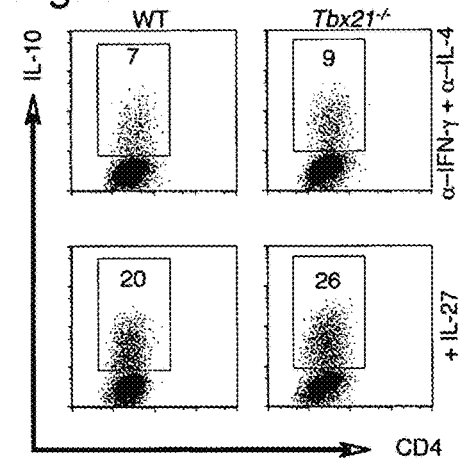
Figure 20C:
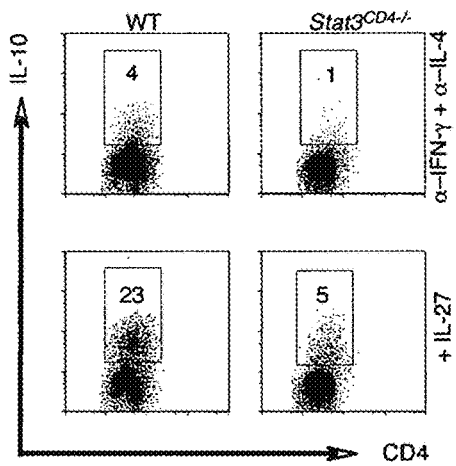
Figure 20D:
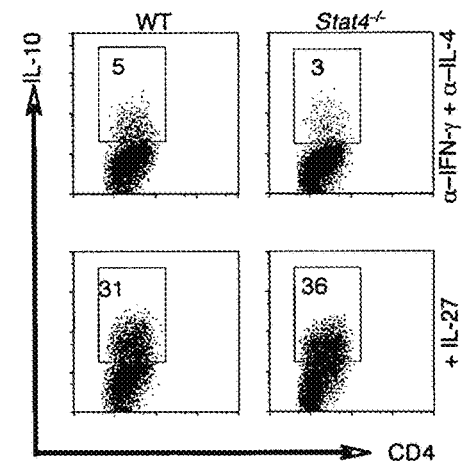
Figure 20E:
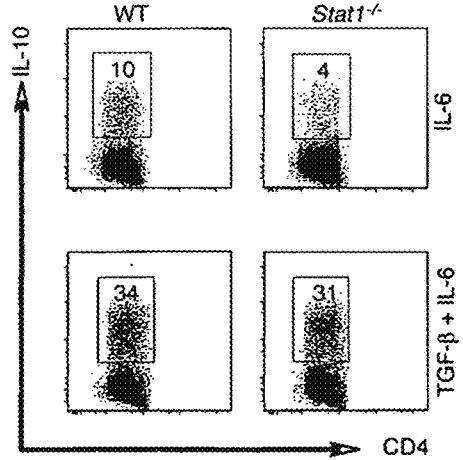
Figure 20F:
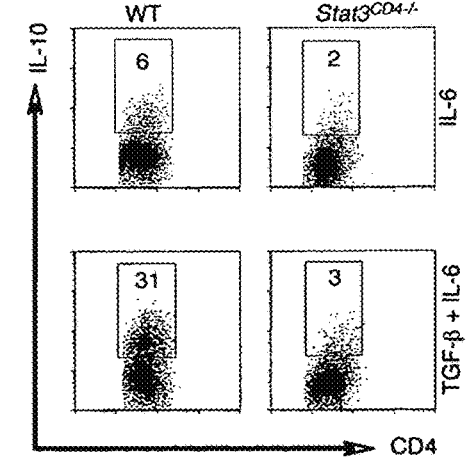

FIG. 16 Panels A-B illustrate that CD4+ T cells make IL-10 in response to IL-27 under T$_H$1 and T$_H$2 but not T$_H$17 conditions. Panel A shows CFSE dilution analysis of CD4+ T cells isolated from C57B/6 mice activated with anti-CD3 and anti-CD28 under non-polarizing conditions in the presence or absence of IL-27 (time, above plots) before staining for intracellular IL-10. Plots are gated on CD4+ T cells. Panel B illustrates flow cyometry of CD4+ T cells isolated from C57BL/6 mice activated with anti-CD3 and anti-CD28 under $T_H1$, $T_H2$ or $T_H17$ polarizing conditions in the presence or absence of IL-27 before intracellular staining of IL-10. Bold numbers represent the MFI. For Panels A and B, numbers in boxes indicate percent IL-10+ cells. Data are representative of three independent experiments with similar results.

FIG. 17 Panels A-B illustrate that IL-27 induces the generation of IFN-γ+IL-10+CD4+ T cells under $T_H1$ conditions. Panel A illustrates flow cytometry of CD4+ T cells isolated from C57BL/6 mice and activated with anti-CD3 and anti-CD28 under $T_H1$, $T_H2$ or $T_H17$ polarizing conditions in the presence or absence of IL-27 before staining for intracellular IL-10 and signature $T_H$ associated cytokines IFN-γ, IL-13 or IL-17. Panel B illustrates flow cytometry of CD4+ T cells isolated from IL-10−/− mice activated with anti-CD3 and anti-CD28 under $T_H17$ inducing conditions in the presence or absence of IL-27 before staining for intracellular IL-10 and IL-17. Plots are gated on CD4+ T cells; numbers in quadrants represent the frequency of cells in each. Data are representative of three (Panel A) or two (Panel B) independent experiments.

FIG. 18 Panels A-C illustrate that TGF-β augments IL-27 driven IL-10 production by CD4+ T cells. Production of IL-10 by CD4+ T cells as measured by flow cytometry (Panel A) and ELISA (Panel B) of 72 h culture supernatants. CD4+ T cells isolated from C7BL/6 mice were activated with anti-CD3 and anti-CD28 under non-polarizing conditions in the presence or absence of IL-27, TGF-β or the combination of both cytokines. CD4+ T cells cultured for 4 d, were stimulated for 4 h with PMA and ionomycin in the presence of brefeldin A before staining for intracellular IL-10. Numbers in boxes indicate percent IL-10+ cells; bold numbers represent MFI. Data are the mean ±s.d. of ten mice. Panel C illustrates flow cytometry of CD4+ T cells isolated from Foxp3GFP reporter mice activated with anti-CD3 and anti-CD28 under non-polarizing conditions in the presence or absence of IL-27, TGF-β or the combination of both cytokines. CD4+ T cells cultured for 3 d, were stimulated for 4 h with PMA and ionomycin in the presence of brefeldin A before staining for intracellular IL-10 and GFP. Plots are gated on CD4+ T cells; numbers in quadrants represent the frequency of cells in each. Data are representative of three (a, b) or two (c) independent experiments.

FIG. 19 Panels A-D illustrate that IL-6 synergizes with TGF-β to promote IL-10 production. Production of IL-10 by CD4+ T cells as measured by flow cytometry (Panel A) and ELISA (Panel B) of 72 h culture supernatants. CD4+ T cells isolated from C7BL/6 mice were activated with anti-CD3 and anti-CD28 under non-polarizing conditions in the presence or absence of IL-6, TGF-β or the combination of both cytokines. CD4+ T cells cultured for 4 d, were stimulated for 4 h with PMA and ionomycin in the presence of brefeldin A before staining for intracellular IL-10. Numbers in boxes indicate percent IL-10+ cells; bold numbers represent MFI. Data are the mean ±s.d. of triplicates. Panels C and D illustrate flow cytometry of purified CD4+ T cells from C57BL/6 mice; cells were left unstimulated or were stimulated with IL-6 or IL-27 (time, above plots), then were stained for intracellular phosphorylated (Panel C) STAT1 (P-STAT1) or (Panel D) STAT3 (P-STAT3). Numbers in boxes represent percent (Panel C) P-STAT1+ or (Panel D) P-STAT3+CD4+ T cells. Data are representative of three (Panels A and B) or two (Panels C and D) independent experiments.

FIG. 20 Panels A-F illustrate that STAT dependent induction of IL-10. Flow cytometry of CD4+ T cells isolated from C7BL/6, Stat1−/− (Panel A) Tbx21−/− (Panel B) Stat3CD4−/− (Panel C) or Stat4−/− (Panel D) mice activated with anti-CD3 and anti-CD28 under non-polarizing conditions in the presence or absence of IL-27 and then stained for intracellular IL-10. Flow cytometry of CD4+ T cells isolated from C7BL/6, Stat1−/− (Panel E) or Stat3CD4−/− (Panel F) mice activated with anti-CD3 and anti-CD28 under non-polarizing conditions with IL-6 in the presence or absence of TGF-β and then stained for intracellular IL-10. Numbers in boxes represent percent IL-10+ cells. Data are representative of three independent experiments.

Figure 21:
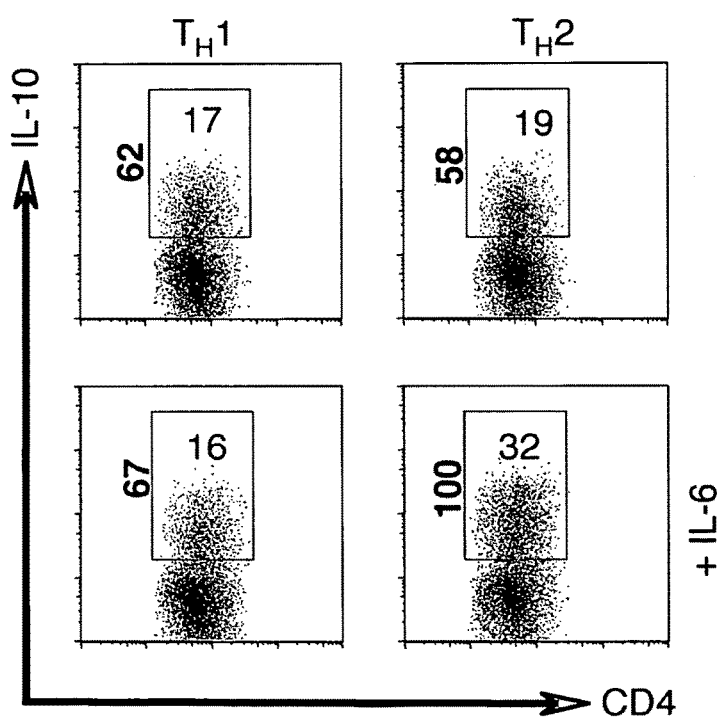

FIG. 21 presents flow cytometry data illustrating that IL-6 induces the generation of IL-10+CD4+ T cells under $T_H2$ conditions. Flow cytometry of CD4+ T cells isolated from C57BL/6 mice and activated with anti-CD3 and anti-CD28 under $T_H1$ or $T_H2$ polarizing conditions in the presence or absence of IL-27 before staining for intracellular IL-10. Numbers in boxes represent percent IL-10+ cells; bold numbers represent the MFI. Data are representative of three independent experiments.

Figure 22:
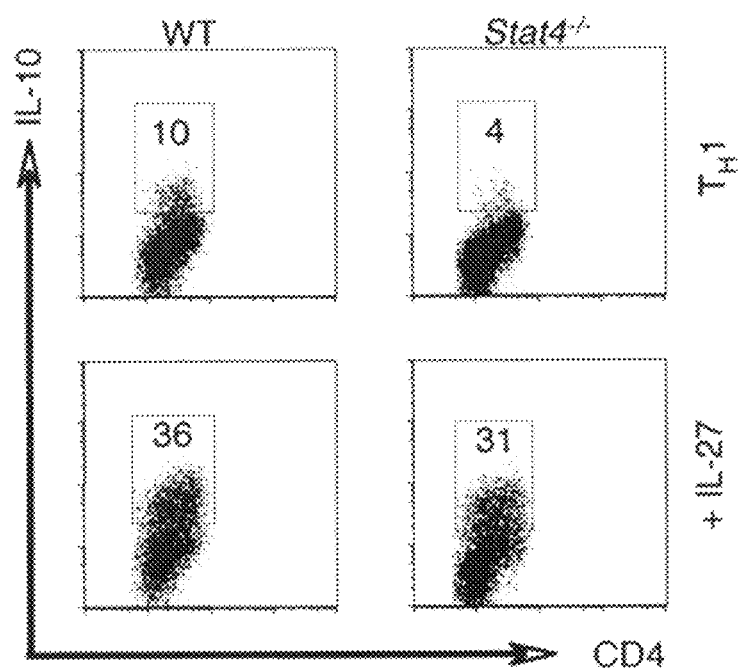

FIG. 22 presents flow cytometry data illustrating that IL-10 production under $T_H1$ conditions is dependent on STAT4. Flow cytometry of CD4+ T cells isolated from C7BL/6 and Stat4−/− mice activated with anti-CD3 and anti-CD28 under $T_H1$ polarizing conditions in the presence or absence of IL-27 and then stained for intracellular IL-10. Numbers in boxes represent percent IL-10+ cells. Data are representative of three independent experiments.

DEFINITIONS

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like.

The term "isolated" refers to a biological material, such as a nucleic acid or a polypeptide, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.)

becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids. An isolated polypeptide, for example, is in an environment (e.g., a cell culture system, or purified from cell culture) other than the native environment of wild-type polypeptide. Preferably, the isolated polypeptide is substantially free from proteins or polypeptides or other contaminants that are found in its natural environment that would interfere with its therapeutic, diagnostic, prophylactic, research or other use.

The term "recombinant" indicates that the material (e.g., a nucleic acid or a polypeptide) has been artificially or synthetically (non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other procedures; a "recombinant polypeptide" or "recombinant protein" is, e.g., a polypeptide or protein which is produced by expression of a recombinant nucleic acid.

The term "nucleic acid" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA, such as 2'-O-methylated oligonucleotides), and the like. A nucleic acid can be e.g., single-stranded or double-stranded. Unless otherwise indicated, a particular nucleic acid sequence of this invention encompasses complementary sequences, in addition to the sequence explicitly indicated.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

"Expression of a gene" or "expression of a nucleic acid" means transcription of DNA into RNA (optionally including modification of the RNA, e.g., splicing), translation of RNA into a polypeptide (possibly including subsequent modification of the polypeptide, e.g., posttranslational modification), or both transcription and translation, as indicated by the context.

The term "gene" is used broadly to refer to any nucleic acid associated with a biological function. Genes typically include coding sequences and/or the regulatory sequences required for expression of such coding sequences. The term "gene" applies to a specific genomic sequence, as well as to a cDNA or an mRNA encoded by that genomic sequence. Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one which regulates transcription in a specific tissue type or cell type, or types.

An "expression vector" is a vector, such as a plasmid, which is capable of promoting expression as well as replication of a nucleic acid incorporated therein. Typically, the nucleic acid to be expressed is "operably linked" to a promoter and/or enhancer, and is subject to transcription regulatory control by the promoter and/or enhancer.

As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In one aspect, the term encode describes the process of semi-conservative DNA replication, where one strand of a double-stranded DNA molecule is used as a template to encode a newly synthesized complementary sister strand by a DNA-dependent DNA polymerase. In another aspect, the term encode refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. In another aspect, a DNA molecule can encode a polypeptide, where it is understood that "encode" as used in that case incorporates both the processes of transcription and translation.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified.

An "amino acid sequence" is a polymer of amino acid residues (a protein, polypeptide, etc.) or a character string representing an amino acid polymer, depending on context.

"Interleukin-27" or "IL-27" is a heterodimeric cytokine that includes "EBI3" and "p28." Other names for p28 in the literature include interleukin 30 or IL30. p28 is described, for example, in entry 608273 in the Online Mendelian Inheritance in Man database, on the world wide web at www (dot) ncbi (dot) nlm (dot) nih (dot) gov/Omim. See also protein sequence id NP_663634 and NP_663611.1, nucleotide sequence accession number NM_145659 and NM_145636.1, and Gene ID 246778 and 246779, available, e.g., through the National Center for Biotechnology Information's Entrez protein, nucleotide, and gene browsers on the world wide web at www (dot) ncbi (dot) nlm (dot) nih (dot) gov/entrez. EBI3 ("Epstein-Barr virus-induced gene 3") is described, for example, in entry 605816 in the Online Mendelian Inheritance in Man database. See also protein sequence id NP_005746 and NP_056581.1, nucleotide sequence accession number NM_005755 and NM_015766, and Gene ID 10148 and 50498.

IL-27 signals through a receptor complex that includes the class I cytokine receptors "WSX-1" and "gp130." Other names for WSX-1 in the literature include T-cell cytokine receptor (TCCR), interleukin 27 receptor alpha (IL27RA), and interleukin 27 receptor (IL27R). WSX-1 is described, for example, in entry 605350 in the Online Mendelian Inheritance in Man database. See also protein sequence id NP_004834 and NP_057880.1, nucleotide sequence accession number NM_004843 and NM_016671, and Gene ID 9466 and 50931. Other names for gp130 in the literature include interleukin 6 signal transducer (IL6ST). gp130 is described, for example, in entry 600694 in the Online Mendelian Inheritance in Man database. See also protein sequence id NP_002175 and NP_034690, nucleotide sequence accession number NM_002184 and NM_010560, and Gene ID 3572 and 16195.

A "WSX-1 polypeptide" (or, analogously, "gp130 polypeptide," "p28 polypeptide," or "EBI3 polypeptide") refers to a polypeptide including the full-length amino acid sequence of a naturally occurring WSX-1 (or gp130, p28, or EBI3) or a subsequence or fragment thereof, or a variant thereof (i.e., a variant of the full-length sequence or the subsequence). Exemplary WSX-1, gp130, p28, and EBI3 polypeptides are presented above; WSX-1, gp130, p28, and EBI3 polypeptides also include polypeptides homologous or substantially identical thereto, and subsequences or variants thereof.

A "subsequence" or "fragment" is any portion of an entire sequence, up to and including the complete sequence. Typically a subsequence or fragment comprises less than the full-length sequence. Optionally, and depending on the length of the complete sequence, a subsequence can include, e.g., at least about 25, at least about 50, at least about 75, at least about 100, at least about 200, at least about 300, or at least about 500 contiguous amino acids of the complete sequence.

The term "variant" (or "derivative") with respect to a polypeptide indicates the variant has an amino acid sequence that is altered by one or more amino acids with respect to a reference sequence (e.g., a naturally occurring sequence). The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variation can also include amino acid deletion or insertion, or both. Guidance in determining which amino acid residues can be substituted, inserted, or deleted without eliminating biological or immunological activity can be found using computer programs well known in the art, for example, DNASTAR software. Examples of conservative substitutions are also described below. Variants also include fusion proteins and polypeptides otherwise derived from the polypeptide. Optionally, the variant is at least about 60% identical to the reference sequence (e.g., a naturally occurring sequence, e.g., a human or mouse WSX-1, gp130, p28, or EBI3 polypeptide sequence) or a subsequence thereof. Frequently, such sequences are at least about 70%, at least about 75%, at least about 80%, at least about 85%, at least about 90%, at least about 95%, at least about 98%, at least about 99%, or at least about 99.5% identical to the reference sequence, for example, over a subsequence of the reference sequence including, e.g., at least about 25, at least about 50, at least about 75, at least about 100, at least about 200, at least about 300, or at least about 500 contiguous amino acids of the reference sequence.

The term "derived from" refers to a component that is isolated from or made using a specified molecule, or information from the specified molecule. For example, a polypeptide that is derived from a second polypeptide can include an amino acid sequence or subsequence that is identical or substantially identical to the amino acid sequence or subsequence of the second polypeptide. In the case of polypeptides, the derived species can be obtained by, for example, naturally occurring mutagenesis, artificial directed mutagenesis, artificial random mutagenesis, or other techniques for producing recombinant polypeptides. Mutagenesis of a polypeptide typically entails manipulation of the polynucleotide that encodes the polypeptide.

The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a cell (or in an in vitro expression system) as a single recombinant fusion protein. As another example, a fusion protein can be produced by covalently connecting (e.g., in vitro) the polypeptide components after each component is produced separately.

A "soluble WSX-1 polypeptide" or "soluble WSX-1" comprises all or part of the extracellular domain of a WSX-1 polypeptide (e.g., a naturally occurring WSX-1 or a variant thereof) but not the transmembrane domain or intracellular domain. The polypeptide (or a complex including the polypeptide) is optionally soluble in aqueous solution at a concentration of at least about 10 µg/ml, at least about 100 µg/ml, at least about 1 mg/ml, or at least about 10 mg/ml.

A "soluble gp130 polypeptide" or "soluble gp130" comprises all or part of the extracellular domain of a gp130 polypeptide (e.g., a naturally occurring gp130 or a variant thereof) but not the transmembrane domain or intracellular domain. The polypeptide (or a complex including the polypeptide) is optionally soluble in aqueous solution at a concentration of at least about 10 µg/ml, at least about 100 µg/ml, at least about 1 mg/ml, or at least about 10 mg/ml.

A "domain" of a protein is any portion of the entire protein, up to and including the complete protein but typically comprising less than the complete protein. A domain can, but need not, fold independently of the rest of the protein chain and/or be correlated with a particular biological function or location (e.g., a ligand binding domain, or a cytosolic, transmembrane or extracellular domain).

The term "inflammatory condition" refers to any disease, disorder, or other condition in which inflammation is present. The inflammation can be, e.g., acute, chronic, localized, and/or systemic and can be mediated by cells of the innate and/or adaptive immune response.

An "anti-inflammatory" composition is one which ameliorates inflammation. For example, the composition can cause resolution of or prevent further worsening of an inflammatory condition.

A "subject" herein is typically a human, but can be a non-human mammal. Exemplary non-human mammals include laboratory, domestic, pet, sport, and stock animals, e.g., mice, cats, dogs, horses, and cows. In one aspect, such subject is eligible for treatment of an inflammatory condition. For the purposes herein, such eligible subject is one that is experiencing or has experienced one or more signs, symptoms, or other indicators of the inflammatory condition. Diagnosis of the condition (and determination of eligibility for treatment) can be performed as established in the art.

"Treatment" of a subject herein refers to both therapeutic treatment and prophylactic or preventative measures. Those in need of treatment include those already with an inflammatory condition as well as those in which inflammation is to be prevented. Hence, the subject may have been diagnosed as having an inflammatory condition or may be predisposed or susceptible to the inflammatory condition.

The term "ameliorates" or "amelioration" as used herein refers to a decrease, reduction or elimination of a condition, disease, disorder, or phenotype, including an abnormality or symptom.

A "symptom" of a condition, disease or disorder is any morbid phenomenon or departure from the normal in structure, function, or sensation, experienced by a subject and indicative of the condition, disease or disorder.

The expression "therapeutically effective amount" refers to an amount that is effective for preventing, ameliorating, or treating a condition, disease or disorder. For example, a "therapeutically effective amount" of a polypeptide or complex refers to an amount of the polypeptide or complex that is effective for preventing, ameliorating, or treating the specified inflammatory condition. Similarly, a "therapeutically effective amount" of a combination of a polypeptide or complex and a second compound (e.g., an antibody, another polypeptide or complex, or a drug) refers to an amount of the polypeptide or complex and an amount of the second compound that, in combination, are effective for preventing, ameliorating, or treating the specified condition.

It is to be understood that the terminology "a combination of" two compounds does not mean that the compounds have to be administered in admixture with each other. Thus, treatment with or use of such a combination encompasses a mixture of the compounds or separate administration of the compounds, and includes administration on the same day or different days. Thus the terminology "combination" means two or more compounds are used for the treatment, either individually or in admixture with each other. When a polypeptide or complex and a second compound, for example, are administered in combination to a subject, the polypeptide or complex is present in the subject at a time when the second compound is also present in the subject, whether the polypeptide or complex and second compound are administered individually or in admixture to the subject.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes.

"Antibody fragments" comprise a portion of an intact antibody, preferably comprising the antigen-binding region thereof. Examples of antibody fragments include Fab, Fab', F(ab')$_2$, and Fv fragments; diabodies; linear antibodies; single-chain antibody molecules; and multispecific antibodies formed from antibody fragments.

An "intact antibody" is one comprising heavy- and light-variable domains as well as an Fc region.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light-chain and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light-chain and the heavy-chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al. Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody-dependent cell-mediated cytotoxicity.

Papain digestion of antibodies produces two identical antigen-binding fragments, called "Fab" fragments, each with a single antigen-binding site, and a residual "Fc" fragment, whose name reflects its ability to crystallize readily. The term "Fc region" refers to such a non-antigen-binding fragment resulting from digestion of whole antibody, whether in monomeric or multimeric form. Pepsin treatment yields an F(ab')$_2$ fragment that has two antigen-binding sites and is still capable of cross-linking antigen.

"Fv" is the minimum antibody fragment that contains a complete antigen-recognition and antigen-binding site. This region consists of a dimer of one heavy-chain and one light-chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy-chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known. See, e.g., Fundamental Immunology, W. E. Paul, ed., Raven Press, N.Y. (1999), for a more detailed description of other antibody fragments.

While various antibody fragments are defined in terms of the digestion of an intact antibody, one of skill will appreciate that such fragments may be synthesized de novo either chemically or by utilizing recombinant DNA methodology. Thus, the term antibody, as used herein, includes antibodies or fragments thereof either produced by the modification of whole antibodies or synthesized de novo using recombinant DNA methodologies.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of antibodies are called α (alpha), δ (delta), ε (epsilon), γ (gamma), and μ (mu), respectively. The subunit structures and three-dimensional configurations of different classes of immunoglobulins are well known.

"Single-chain Fv" or "scFv" antibody fragments that comprise the $V_H$ and $V_L$ domains of antibody, wherein these domains are present in a single polypeptide chain. Preferably, the Fv polypeptide further comprises a polypeptide linker between the $V_H$ and $V_L$ domains that enables the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 1993/11161; and Hollinger et al., Proc. Natl. Acad. Sci. USA, 90:6444-6448 (1993).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). Chimeric antibodies of interest herein include "primatized" antibodies comprising variable-domain antigen-binding sequences derived from a non-human primate (e.g. Old World Monkey, such as baboon, rhesus, or cynomolgus monkey) and human constant-region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

The term "hypervariable region" when used herein refers to the amino acid residues of an antibody that are responsible for antigen binding. The hypervariable region comprises amino acid residues from a "complementarity-determining region" or "CDR" (see, e.g., Kabat et al. Sequences of Proteins of Immunological Interest, 5th Ed. Public Health Service, National Institutes of Health, Bethesda, Md. (1991)) and/or those residues from a "hypervariable loop" (see, e.g., Chothia and Lesk J. Mol. Biol. 196:901-917 (1987)). "Framework" or "FR" residues are those variable-domain residues other than the hypervariable region residues as herein defined.

The terms "Fc receptor" and "FcR" are used to describe a receptor that binds to the Fc region of an antibody. FcRs are reviewed in Ravetch and Kinet (1991) Annu. Rev. Immunol 9:457-92; Capel et al. (1994) Immunomethods 4:25-34; and de Haas et al. (1995) J. Lab. Clin. Med. 126:330-41. Other FcRs, including those to be identified in the future, are encompassed by the term "FcR" herein. The term also includes the neonatal receptor, FcRn, which is responsible for the transfer of maternal IgGs to the fetus (Guyer et al. (1976) J. Immunol. 117:587 and Kim et al. (1994) J. Immunol. 24:249).

An "activity modulator" modulates (enhances or inhibits) an activity of a polypeptide or complex (e.g., a receptor or receptor ligand), either partially or completely. A modulator can be, e.g., a small molecule, a polypeptide, a nucleic acid, etc.

An "agonist" is a compound (e.g., an endogenous substance or a drug) that can bind to and activate a receptor, thereby initiating a response (e.g., a physiological or pharmacological response) characteristic of that receptor. Agonists can be, e.g., full agonists or partial agonists.

An "antagonist" is a compound (e.g., a drug) that can bind to a receptor and prevent an agonist from binding to and activating that receptor. Typically, binding of an antagonist to a receptor forms a complex which does not give rise to any response, as if the receptor were unoccupied. Alternatively, the antagonist can be a partial agonist.

It is worth noting that certain compounds can be classified as both an agonist and an antagonist. For example, a "mixed agonist-antagonist" (also called a "partial agonist") is a compound which possesses affinity for a receptor, but which, unlike a full agonist, will elicit only a small degree of the response characteristic of that receptor, even if a high proportion of receptors are occupied by the compound. Such occupancy of the receptors by the partial agonist can prevent binding of a full agonist (e.g., an endogenous agonist) to the receptor.

A variety of additional terms are defined or otherwise characterized herein.

DETAILED DESCRIPTION

There are numerous inflammatory conditions in which T cells are critical mediators of disease, and much effort has focused on the development of strategies to specifically inhibit T cell responses. For example, inflammatory bowel disease, Crohn's disease, multiple sclerosis, uveitis, psoriasis, arthritis, asthma, lupus and transplant rejection are all conditions which involve T cells. The immune response has also been implicated in a variety of other idiopathic conditions, such as ankalyzing spondalitis and sarcoidosis. For all of these conditions, there is a pressing need to develop new therapeutic approaches. The recognition that WSX-1 is important in the inhibition of T cell responses means that this receptor represents a viable target to prevent these type of inflammatory responses. Alternatively, blockade of this receptor could be used to augment T cell responses, for example during vaccination or immune mediated therapy for cancer. In addition, certain types of tumors that express WSX-1 may also be susceptible to inhibitory signaling through this receptor.

Other cells expressing WSX-1 or its partner gp130 (including cells expressing both) can be similarly targeted. Responses mediated by either WSX-1-expressing cells or by gp130-expressing cells can be modulated, for example, by a soluble gp130 polypeptide or complex or a soluble WSX-1 polypeptide or complex, respectively, or by p28. Thus, responses mediated by B cells, mast cells, neutrophils, macrophages, dendritic cells, and/or the like can be modulated by activation or blockade of the relevant receptor(s).

Potential Commercial Uses and Applications p28, alone or in combination with a soluble form of WSX-1, can be used to suppress many inflammatory conditions including, but not limited to, allergies, arthritis, inflammatory bowel disease, uveitis, certain cancers, psoriasis, lupus, multiple sclerosis, and chronic infectious diseases such as tuberculosis and hepatitis. Similar approaches are implied as being useful therapeutic approaches from these observations. Thus, a WSX-1 fusion protein (e.g., with an immunoglobulin) is useful since it interacts with endogenous IL-27 and promotes its interaction with gp130 and promotes negative effects on the targets. Therapeutic molecules can also be constructed to have dual functions; for example, such a molecule can be based on an antibody structure where one chain can recognize a cell specific marker such as, but not limited to, CD4, CD8, CD11c, etc. and the other chain contains a WSX-1 or p28 fusion. This permits targeting of very specific cell types. Additionally, the recognition that the receptor biology encompasses elements of trans signaling leads to the idea that soluble forms of gp130 in complexes with IL-27 or p28 (or even EBI3) can also act to promote specific signaling through WSX-1. Without limitation to any particular mechanism, in our current model the different receptor chains of the IL-27 receptor have unique signaling functions and can affect distinct T cell functions. This concept leads to the design of molecules that affect T cell production of particular cytokines very specifically. Based exclusively on our work and data, we suggest that this approach can be used to target, for example, IL-2, IFN-gamma, TNF-alpha, IL-6, IL-4, IL-13, IL-17 and IL-25, as well as IL-10, IL-5, and/or CD25. These all represent valid drug targets for biotech and are important in many T cell mediated inflammatory diseases. FIG. 13 Panels A-C outline some candidate strategies. As discussed in greater detail and with additional examples herein, there are many additional approaches that can be formulated based on this information that allow us to rationally target discrete immune functions.

Anti-Inflammatory Compositions

One aspect of the invention provides compositions including novel polypeptides and complexes, including compositions having anti-inflammatory activity.

One general class of embodiments provides a composition comprising an isolated or recombinant soluble WSX-1/p28 polypeptide complex, an isolated or recombinant soluble WSX-1/EBI3 polypeptide complex, an isolated or recombinant soluble WSX-1/IL-27 complex, an isolated or recombinant soluble gp130/p28 polypeptide complex, an isolated or recombinant soluble gp130/EBI3 polypeptide complex, an isolated or recombinant soluble gp130/IL-27 complex, or a variant thereof. By way of example, a "soluble WSX-1/p28 polypeptide complex" comprises a soluble WSX-1 polypeptide in complex with a p28 polypeptide, and a variant of the complex includes a variant soluble WSX-1 polypeptide and/or a variant p28 polypeptide.

In one aspect, the composition is anti-inflammatory. The composition optionally decreases inflammation when administered to a subject, e.g., a human or animal exhibiting inflammation prior to such administration. Similarly, the composition optionally alters (e.g., decreases) one or more cellular activities characteristic of an inflammatory response, for example, expression of particular cytokines, in cells to which the composition is applied relative to cells not exposed to the composition. The composition optionally includes a pharmaceutically acceptable excipient, for example, in embodiments in which the composition is to be administered to a subject. In one embodiment, the composition suppresses development of IL-17 producing cells (also called T17 cells) from naïve T cells induced by IL-6 and transforming growth factor beta (TGF-β). For example, the composition can suppress development of IL17 producing CD4$^+$ T helper cells (T$_H$-17) from naïve T cells induced by IL-6 and transforming growth factor beta. Similarly, the composition optionally suppresses one or more function of T17 cells. In one embodiment, the composition includes TGF-β.

The composition can include one or more cell, for example, one or more T cell, B cell, mast cell, neutrophil, macrophage, dendritic cell, or other cell expressing gp130 (e.g., endothelial cell) or WSX-1. The complex can affect a function or activity of the cell. In one embodiment, the composition includes a T-cell, and the composition alters a function or activity of the T-cell, relative to a corresponding T-cell not treated with the composition. For example, the T-cell can display altered expression of IL-2, IFN-gamma, TNF-alpha, IL-6, IL-4, IL-13, IL-17, IL-25, IL-10, IL-5, or CD25, altered proliferation, or altered survival. Expression of the various cytokines can be detected by any of a variety of techniques well known in the art, e.g., for detecting mRNA and/or protein levels. Expression of the cytokines (e.g., IL-2 and IFN-gamma) is typically downregulated by the complex, although production of inhibitory cytokine IL-10 is typically increased. Typically, a WSX-1 complex is used to modulate activity of a cell that expresses gp130 (and optionally also WSX-1), while a gp130 complex is used to modulate activity of a cell that expresses WSX-1 (and optionally also gp130).

Suitable soluble WSX-1 and gp130 polypeptides include, for example, the extracellular domain of WSX-1 or gp130 or a portion (a subsequence) thereof. The extracellular domain is optionally part of a fusion protein, e.g., one of those described herein or a fusion with a Fc region, e.g., an IgG Fc domain. See, for example, U.S. patent application publication 20040185049 by Hunter and Villarino entitled "Methods for modulating an inflammatory response" and Wirtz et al. "Protection from lethal septic peritonitis by neutralizing the biological function of interleukin 27" J. Exp. Med. 10.1084/jem.20060471 for a description of exemplary soluble WSX-1 polypeptides. Additional soluble WSX-1 polypeptides are readily constructed, and some are commercially available. For example, human and mouse TCCR/WSX-1/Fc chimeras are available from R&D Systems (on the web at www (dot) rndsystems (dot) com). Soluble gp130 polypeptides can be analogously produced; see, e.g., Jostock et al. (2001) "Soluble gp130 is the natural inhibitor of soluble interleukin-6 receptor transsignaling responses" Eur. J. Biochem. 268:160-167 and Lin et al. (2006) "The functional expression of a biologically active fragment of soluble gp130 as an ELP fusion protein in transgenic plants: purification via inverse-transition-cycling" Biochem J. May 23 doi: 10.1042/BJ20060544. Similarly, suitable p28 and EBI3 polypeptides include, e.g., p28 or EBI3 or a subsequence thereof. The components of the complex are optionally noncovalently associated in the complex, or are optionally covalently connected by a chemical crosslinker or the like in the complex.

Fusion proteins are another feature of the invention. Accordingly, one general class of embodiments provides a recombinant or isolated WSX-1 fusion protein. The fusion protein includes a WSX-1 polypeptide, which can be, e.g., at the N-terminus of the fusion protein, at the C-terminus of the fusion protein, or internal to the fusion protein. The WSX-1 polypeptide can include the extracellular domain, or a subsequence thereof, of a naturally occurring WSX-1 (e.g., human WSX-1) or a variant thereof.

In one class of embodiments, the fusion protein comprises one or more domains that recognize a cell-specific marker, for example, one or more antibody domains (e.g., $V_H$ and $V_L$ domains) that recognize the marker. The cell-specific marker can be essentially any cell-specific marker, for example, a marker for a lymphocyte population, a T cell, a cell of the innate immune response such as a neutrophil, dendritic cell, or mast cell, or a cancer cell. A variety of such markers for various cell types are known in the art, and more can be determined by techniques well known in the art. In one class of embodiments, the cell-specific marker is selected from CD4, CD8, CD11c, CD11b, and NK1.1.

In one class of embodiments, the fusion protein comprises one or more polypeptide domains derived from p28 or EBI3. The fusion protein optionally includes domains derived from both p28 and EBI3. The WSX-1 polypeptide can be joined to the p28 or EBI3 polypeptide through a linker. Many suitable linkers are known in the art (e.g., linkers including 4-6 Gly and/or Ala residues), and additional linkers are readily designed (see, e.g., Crasto and Feng (2000) "LINKER: A program to generate linker sequences for fusion proteins" Protein Engineering 13:309-312).

The fusion protein can be monomeric, dimeric (e.g., homodimeric or heterodimeric), or multimeric. The fusion protein is preferably soluble. Optionally, the fusion protein forms a complex with p28, EBI3, or IL-27.

Essentially all of the features noted for the embodiments above apply to these embodiments as well, as relevant. For example, a composition including the fusion protein optionally includes a pharmaceutically acceptable excipient, a cell (e.g., a T-cell), and/or TGF-β.

Another general class of embodiments provides a recombinant or isolated p28 fusion protein. The fusion protein includes a p28 polypeptide, which can be, e.g., at the N-terminus of the fusion protein, at the C-terminus of the fusion protein, or internal to the fusion protein. The p28 polypeptide can be derived from a naturally occurring p28 (e.g., human p28) or a variant thereof.

The fusion protein optionally comprises one or more antibody domains. For example, the fusion protein can include one or more antibody domains that recognizes a cell-specific marker.

Essentially all of the features noted for the embodiments above apply to these embodiments as well, as relevant, for example, with respect to cell-specific markers, solubility, monomeric, dimeric, or multimeric status, complex formation, inclusion in compositions (e.g., with a pharmaceutically acceptable excipient, a cell, and/or TGF-β), and/or the like.

It will be evident that gp130 and EBI3 fusion proteins are analogously constructed and form another feature of the invention.

Screening for Modulators

Compounds that modulate the activity of WSX-1, p28, EBI3, and/or gp130 can be useful, for example, for treating inflammation or otherwise modulating the inflammatory response. Accordingly, one general class of embodiments provides methods of identifying a compound that binds to or modulates an activity of a soluble WSX-1 polypeptide, a soluble WSX-1/p28 polypeptide complex, a soluble WSX-1/IL-27 polypeptide complex, a soluble WSX-1/EBI3 polypeptide complex, a soluble gp130/p28 polypeptide complex, a soluble gp130/IL-27 polypeptide complex, or a soluble gp130/EBI3 polypeptide complex. In the methods, a biological or biochemical sample comprising the polypeptide or complex is contacted with a test compound. Binding of the test compound to the polypeptide or complex or modulation of the activity of the polypeptide or complex by the test compound is detected, thereby identifying the compound that binds to or modulates the activity of the polypeptide or complex.

In one class of embodiments, the compound potentiates inhibition of a T cell response by the polypeptide or complex, potentiates antagonist activity against IL-2 or IL-17, or alters T cell proliferation, survival, or expression of IL-2, IFN-gamma, TNF-alpha, IL-6, IL-4, IL-13, IL-17, IL-25, IL-10, IL-5, or CD25 relative to a corresponding T cell not treated with the compound. The compound optionally binds to the IL-27 receptor, blocks interaction between WSX-1 and gp130, potentiates interaction between WSX-1 and gp130, potentiates interaction of p28 with WSX-1 or the IL-27 receptor, or the like. Exemplary compounds include antibodies (e.g., antibodies against WSX-1, p28, EBI3, and/or gp130 polypeptides), agonists, antagonists, and activity modulators, for example, small molecules.

The biological or biochemical sample can include isolated or recombinant polypeptides or complexes, cells (e.g., T-cells), tissue samples, and/or the like. T cell responses such as proliferation, survival, and marker expression can be assayed by techniques known in the art.

Antibodies

Antibodies that bind specifically to a soluble WSX-1 polypeptide, a p28 polypeptide, an isolated or recombinant soluble WSX-1/p28 polypeptide complex, an isolated or recombinant soluble WSX-1/EBI3 polypeptide complex, an isolated or recombinant soluble WSX-1IL-27 polypeptide complex, an isolated or recombinant soluble gp130/IL-27 complex, an isolated or recombinant soluble gp130/p28 polypeptide complex, an isolated or recombinant soluble gp130/EBI3 polypeptide complex, or a variant thereof are a feature of the invention. Such an antibody optionally modulates, e.g., potentiates, an activity of the polypeptide or polypeptide complex. In one embodiment, the antibody binds to or modulates an activity of a gp130/WSX-1/IL-27 complex or modulates formation of the complex in a cell. For example, the antibody can increase the half-life of the complex. Such antibodies can include, but are not limited to, polyclonal, monoclonal, chimeric, humanized, single chain, Fab fragments and fragments produced by an Fab expression library. Such antibodies find use, for example, in treatment of inflammatory conditions. Methods for generating such antibodies will be described here.

Antigen to be used for production of, or screening for, antibody(ies) may be, e.g., a soluble form of WSX-1, p28, gp130, or EBI3, or a portion or complex thereof, containing the desired epitope. Alternatively, or additionally, cells expressing WSX-1 or gp130 at their cell surface can be used to generate, or screen for, antibody(ies). Other forms of WSX-1, p28, gp130, or EBI3 polypeptides useful for generating antibodies will be apparent to those skilled in the art. Antibodies that facilitate action of IL2 and IL6 are known in the art; screening for antibodies that facilitate action of WSX-1, p28, gp130, and/or EBI3 can be obtained through similar methods. See, e.g., Boyman et al. (2006) "Selective Stimulation of T Cell Subsets with Antibody-Cytokine Immune Complexes" Science 311:1924-1927 and Suzuki et al. (1994) "Antibody against interleukin-6 reduces inflammation and numbers of cysts in brains of mice with toxoplasmic encephalitis" Infect Immun. 62: 2773-2778. For example, antibodies raised against WSX-1, p28, gp130, and/or EBI3 polypeptides (including complexes) can be assayed for binding to the polypeptides or complexes thereof or assayed to determine whether they modulate activity of the polypeptides or complexes using techniques known in the art. An antibody that binds to a complex is optionally an antibody which binds to a polypeptide component of the complex regardless of whether that polypeptide is part of the complex or not, or is optionally an antibody that specifically binds to the complex and not to any polypeptide component of the complex (e.g., the antibody can bind the complex with at least 1000-fold greater affinity than it binds a component of the complex).

Numerous methods for producing antibodies are known to those of skill in the art, and can be adapted to produce antibodies specific for polypeptides or complexes of the invention. See the sections below, as well as, e.g., Coligan (1991) *Current Protocols in Immunology* Wiley/Greene, NY; and Harlow and Lane (1989) *Antibodies: A Laboratory Manual* Cold Spring Harbor Press, NY; Stites et al. (eds.) *Basic and Clinical Immunology* (4$^{th}$ ed.) Lange Medical Publications, Los Altos, Calif., and references cited therein; Goding (1986) *Monoclonal Antibodies: Principles and Practice* (2d ed.) Academic Press, New York, N.Y.; *Fundamental Immunology*, e.g., 4$^{th}$ Edition (or later), W. E. Paul (ed.), Raven Press, N.Y. (1998); and Kohler and Milstein (1975) *Nature* 256: 495-497. Other suitable techniques for antibody preparation include selection of libraries of recombinant antibodies in phage or similar vectors. See, Huse et al. (1989) *Science* 246: 1275-1281; and Ward, et al. (1989) *Nature* 341: 544-546. Additional details on antibody production and engineering techniques can be found in U.S. Pat. No. 5,482,856, Borrebaeck (ed) (1995) *Antibody Engineering*, 2$^{nd}$ *Edition* Freeman and Company, NY (Borrebaeck); McCafferty et al. (1996) *Antibody Engineering, A Practical Approach* IRL at Oxford Press, Oxford, England (McCafferty), Paul (1995) *Antibody Engineering Protocols* Humana Press, Towata, N.J. (Paul), Ostberg et al. (1983) *Hybridoma* 2: 361-367, Ostberg, U.S. Pat. No. 4,634,664, and Engelman et al. U.S. Pat. No. 4,634,666. Specific antibodies (e.g., specific monoclonal and polyclonal antibodies) and antisera will usually bind with a $K_D$ of at least about 0.1 μM, preferably at least about 0.01 μM or better, and most typically and preferably, 0.001 μM or better. As will be appreciated, binding characteristics of such an antibody will typically depend upon the specific application to which the antibody is to be put, including environmental characteristics, e.g., pH, salt concentration, and the like. In certain preferred aspects, environmental conditions will typically include those of biochemical systems, e.g., pH between about 2 and about 9 (e.g., about 7), and salt levels at biochemically relevant ionic strength, e.g., between about 0 mM and 100 mM.

Polyclonal Antibodies

Polyclonal antibodies are preferably raised in animals by multiple subcutaneous or intraperitoneal injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or R'N=C=NR, where R and R' are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson et al., Anal. Biochem., 107: 220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose® cross-linked agarose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Revs., 130:151-188 (1992).

In a further embodiment, antibodies or antibody fragments can be isolated from antibody phage libraries generated using the techniques described in McCafferty et al., Nature, 348:552-554 (1990). Clackson et al., Nature, 352: 624-628 (1991) and Marks et al., J. Mol. Biol., 222:581-597 (1991) describe the isolation of murine and human antibodies, respectively, using phage libraries. Subsequent publications describe the production of high-affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 81:6851 (1984)), or by covalently joining to the immunoglobulin-coding sequence all or part of the coding sequence for a non-immunoglobulin polypeptide.

Optionally, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized Antibodies

Methods for humanizing non-human antibodies have been described in the art. Preferably, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting hypervariable-region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable-region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light- or heavy-chain variable regions. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain-joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589,369 and 5,545,807.

Alternatively, phage-display technology (McCafferty et al., Nature 348:552-553 (1990)) can be used to produce human antibodies and antibody fragments in vitro, from immunoglobulin variable (V)-domain gene repertoires from unimmunized donors. According to this technique, antibody V-domain genes are cloned in frame into either a major or minor coat-protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

Human antibodies may also be generated by in vitro-activated B cells (see U.S. Pat. Nos. 5,567,610 and 5,229,275).

Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10: 163-167 (1992)). According to another approach, F(ab')$_2$ fragments can be isolated directly from recombinant host-cell culture. Other techniques for the production of antibody fragments will be apparent to the skilled practitioner. In other embodiments, the antibody of choice is a single-chain Fv fragment (scFv). See WO 1993/16185 and U.S. Pat. Nos. 5,571,894 and 5,587,458. The antibody fragment may also be a "linear antibody", e.g., as described in U.S. Pat. No. 5,641,870. Such linear antibody fragments may be monospecific or bispecific.

Bispecific Antibodies

Bispecific antibodies are antibodies that have binding specificities for at least two different epitopes. Exemplary bispecific antibodies may bind to two different epitopes of the WSX-1, p28, gp130, or EBI3 antigen. Other such antibodies may bind one of WSX-1, p28, gp130, or EBI3 and further bind another of WSX-1, p28, gp130, or EBI3 or a T-cell surface marker. Bispecific antibodies may also be used to localize drugs or cytotoxic agents to a cell comprising the antigen; these antibodies possess a WSX-1, p28, gp130, or EBI3-binding arm and an arm that binds the drug or cytotoxic agent. Bispecific antibodies can be prepared as full-length antibodies or antibody fragments (e.g. F(ab')$_2$ bispecific antibodies).

Methods for making bispecific antibodies are known in the art. Traditional production of full-length bispecific antibodies is based on the coexpression of two immunoglobulin heavy-chain-light-chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 1993/08829, and in Traunecker et al., EMBO J., 10:3655-3659 (1991).

According to a different approach, antibody variable domains with the desired binding specificities (antibody-antigen combining sites) are fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1), containing the site necessary for light-chain binding, present in at least one of the fusions. DNAs encoding the immunoglobulin heavy-chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy-chain-light-chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 1994/04690. For further details of generating bispecific antibodies, see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 1991/00360, WO 1992/200373, and EP 03089). Heteroconjugate antibodies may be made using any convenient cross-linking methods. Suitable cross-linking agents are well known in the art, and are disclosed, for example, in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., J. Immunol., 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

It will be evident that certain fusion proteins, e.g., certain WSX-1 or p28 fusion proteins, can be prepared using techniques analogous to those for bispecific antibody production. A WSX-1 or p28 fusion protein based on a bispecific antibody can possess one arm that binds a cell-specific marker (e.g., CD4, CD8, CD11c, CD11b, and NK1.1), and one arm on which the antigen binding domains are replaced with a WSX-1 or p28 polypeptide.

Conjugates and Other Modifications of the Antibody

The antibody used in the methods or included in the articles of manufacture herein is optionally conjugated to a drug, e.g., as described in WO 2004/032828 and U.S. patent application publication 2006/0024295. The antibodies of the present invention may also be conjugated with a prodrug-activating enzyme that converts a prodrug (e.g. a peptidyl chemotherapeutic agent, see WO 1981/01145) to an active anti-cancer or other drug. See, for example, WO 1988/07378, U.S. Pat. No. 4,975,278, and U.S. patent application publication 2006/0024295.

Other modifications of the antibody are contemplated herein. For example, the antibody may be linked to one of a variety of nonproteinaceous polymers, e.g., polyethylene glycol (PEG), polypropylene glycol, polyoxyalkylenes, or copolymers of polyethylene glycol and polypropylene glycol.

The antibodies disclosed herein may also be formulated as liposomes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); U.S. Pat. Nos. 4,485,045 and 4,544,545; and WO 1997/38731 published Oct. 23, 1997. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody of the present invention can be conjugated to the liposomes as described in Martin et al. J. Biol. Chem. 257: 286-288 (1982) via a disulfide-interchange reaction. A chemotherapeutic agent is optionally contained within the liposome. See Gabizon et al. J. National Cancer Inst. 81(19) 1484 (1989).

Amino acid sequence modification(s) of protein or peptide antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine-scanning mutagenesis" as described by Cunningham and Wells Science, 244:1081-1085 (1989). Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody of an enzyme, or a polypeptide that increases the serum half-life of the antibody.

Another type of variant is an amino acid substitution variant. These variants have at least one amino acid residue in the antibody molecule replaced by a different residue. The sites of greatest interest for substitutional mutagenesis of antibodies include the hypervariable regions, but FR alterations are also contemplated. Such substitutions can be conservative or nonconservative.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

One type of substitutional variant involves substituting one or more hypervariable region residues of a parent antibody. Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine-scanning mutagenesis can be performed to identify hypervariable region residues contributing significantly to antigen binding. Alternatively, or in additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. Such altering includes deleting one or more carbohydrate moieties found in the antibody, and/or adding one or more glycosylation sites that are not present in the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered or removed. For example, in one glycosylation variant herein, one or more amino acid substitutions are introduced in an Fc region of an antibody to eliminate one or more glycosylation sites. Such an aglycosylated antibody can have reduced effector function, e.g., as compared to human IgG1, such that its ability to induce complement activation and/or antibody dependent cell-mediated cytotoxicity is decreased, and the aglycosylated antibody can have reduced (or no) binding to the Fc receptor.

For certain antibodies, e.g., depleting antibodies, modification of the antibody to enhance ADCC and/or CDC of the antibody may be desirable. For example, antibodies with a mature carbohydrate structure that lacks fucose attached to an Fc region of the antibody are described in U.S. 2003/0157108 (Presta, L.). See also U.S. 2004/0093621 (Kyowa Hakko Kogyo Co., Ltd.). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof.

Thus a glycosylation variant optionally comprises an Fc region, wherein a carbohydrate structure attached to the Fc region lacks fucose. Such variants have improved ADCC function. Optionally, the Fc region further comprises one or more amino acid substitutions therein that further improve ADCC, for example, substitutions at positions 298, 333, and/or 334 of the Fc region (Eu numbering of residues). Examples of publications related to "defucosylated" or "fucose-deficient" antibodies include: U.S. 2003/0157108; WO 2000/61739; WO 2001/29246; U.S. 2003/0115614; U.S. 2002/0164328; U.S. 2004/0093621; U.S. 2004/0132140; U.S. 2004/0110704; U.S. 2004/0110282; U.S. 2004/0109865; WO 2003/085119; WO 2003/084570; WO 2005/035586; WO 2005/035778; Okazaki et al. J. Mol. Biol. 336:1239-1249 (2004); and Yamane-Ohnuki et al. Biotech. Bioeng. 87: 614 (2004). Examples of cell lines producing defucosylated antibodies include Lec13 CHO cells deficient in protein fucosylation (Ripka et al. Arch. Biochem. Biophys. 249:533-545 (1986); U.S. 2003/0157108, Presta, L; and WO 2004/056312, Adams et al., especially at Example 11), and knockout cell lines, such as alpha-1,6-fucosyltransferase gene, FUT8,-knockout CHO cells (Yamane-Ohnuki et al. Biotech. Bioeng. 87: 614 (2004)).

Modification of the antibody with respect to effector function, e.g. so as to enhance ADCC and/or CDC of the antibody, may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and ADCC. See Caron et al., J. Exp Med. 176:1191-1195 (1992) and Shopes, B. J. Immunol 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered that has dual Fc regions and may thereby have enhanced complement lysis and ADCC capabilities. See Stevenson et al. Anti-Cancer Drug Design 3:219-230 (1989). WO 2000/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region. Preferably, the altered Fc region is a human IgG1 Fc region comprising or consisting of substitutions at one, two, or three of these positions.

Antibodies with altered C1q binding and/or CDC are described in WO 1999/51642 and U.S. Pat. Nos. 6,194,551, 6,242,195, 6,528,624, and 6,538,124 (Idusogie et al.). The antibodies comprise an amino acid substitution at one or more of amino acid positions 270, 322, 326, 327, 329, 313, 333, and/or 334 of the Fc region thereof.

To increase the serum half-life of the antibody, one may incorporate a salvage receptor binding epitope into the antibody (especially an antibody fragment) as described in U.S. Pat. No. 5,739,277, for example. As used herein, the term salvage receptor binding epitope refers to an epitope of the Fc region of an IgG molecule (e.g., $IgG_1$, $IgG_2$, $IgG_3$, or $IgG_4$) that is responsible for increasing the in vivo serum half-life of the IgG molecule. Antibodies with substitutions in an Fc region thereof and increased serum half-lives are also described in WO 2000/42072 (Presta, L.).

Any of the non-depleting (or other) antibodies of the invention may comprise at least one substitution in the Fc region that improves FcRn binding or serum half-life. For example, the invention further provides an antibody comprising a variant Fc region with altered neonatal Fc receptor (FcRn) binding affinity. FcRn is structurally similar to major histocompatibility complex (MHC) and consists of an α-chain noncovalently bound to β2-microglobulin. The multiple functions of the neonatal Fc receptor FcRn are reviewed in Ghetie and Ward (2000) Annu. Rev. Immunol. 18:39-766. FcRn plays a role in the passive delivery of immunoglobulin IgGs from mother to young and the regulation of serum IgG levels. FcRn acts as a salvage receptor, binding and transporting pinocytosed IgGs in intact form both within and across cells, and rescuing them from a default degradative pathway. Although the mechanisms responsible for salvaging IgGs are still unclear, it is thought that unbound IgGs are directed toward proteolysis in lysosomes, whereas bound IgGs are recycled to the surface of the cells and released. This control takes place within the endothelial cells located throughout adult tissues. FcRn is expressed in at least the liver, mammary gland, and adult intestine. FcRn binds to IgG; the FcRn-IgG interaction has been studied extensively and appears to involve residues at the CH2, CH3 domain interface of the Fc region of IgG. These residues interact with residues primarily located in the α2 domain of FcRn.

In certain embodiments of the invention, a non-depleting variant antibody may display increased binding to FcRn and comprise an amino acid modification at any one or more of amino acid positions 238, 256, 265, 272, 286, 303, 305, 307, 311, 312, 317, 340, 356, 360, 362, 376, 378, 380, 382, 413, 424 or 434 of the Fc region, wherein the numbering of the residues in the Fc region is that of the EU index as in Kabat. See, e.g., U.S. Pat. No. 6,737,056; and, Shields et al., J. Biol. Chem. 276: 6591-6604 (2001). In one embodiment of the invention, an antibody comprises a variant IgG Fc region comprising at least an amino acid substitution at Asn 434 to His (N434H). In one embodiment of the invention, an antibody comprises a variant IgG Fc region comprising at least an amino acid substitution at Asn 434 to Ala (N434A). Typically, these variants comprise a higher binding affinity for FcRN than polypeptides having native sequence/wild-type sequence Fc region. These Fc variant polypeptide and antibodies have the advantage of being salvaged and recycled rather than degraded. These non-depleting antibodies can be used in the methods provided herein.

Engineered antibodies with three or more (preferably four) functional antigen-binding sites are also contemplated (US 2002/0004587 A1, Miller et al.).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

Treatment of Inflammation

One aspect of the invention provides methods of treating an inflammatory condition in a mammalian subject, e.g., a human subject. The inflammatory condition to be treated can be essentially any inflammatory condition. The condition is optionally T cell-mediated; for example, the condition can be mediated by $T_H1$ cells, $T_H2$ cells, T17 cells, $T_H$-17 cells, $CD4^+$ T cells, $CD8^+$ T cells, gamma/delta T cells, natural killer T cells, and/or regulatory T cells. Exemplary inflammatory conditions to be treated include, but are not limited to, an immune disorder (e.g., an autoimmune disease); an infection; cancer, such as multiple myeloma and myelogenous and other leukemias, as well as tumor metastasis; an allergy; arthritis; asthma; inflammatory bowel disease, such as ulcerative colitis or Crohn's disease; uveitis; psoriasis; lupus; multiple sclerosis; a chronic infectious disease; tuberculosis; ankalyzing spondalitis; transplant rejection; sarcoidosis; hepatitis; inflammation of the central nervous system; Acquired Immune Deficiency Syndrome; acute pancreatitis; Addison's disease; alcohol-induced liver injury including alcoholic cirrhosis; Alzheimer's disease; amyelolateroschlerosis; asthma and other pulmonary diseases; atherosclerosis; autoimmune vasculitis; autoimmune hepatitis-induced hepatic injury; biliary cirrhosis; cachexia/anorexia, including AIDS-induced cachexia; chronic fatigue syndrome; *Clostridium* associated illnesses, including *Clostridium*-associated diarrhea; coronary conditions and indications, including congestive heart failure, coronary restenosis, myocardial infarction, myocardial dysfunction, and coronary artery bypass graft; diabetes, including juvenile onset Type 1, diabetes mellitus, and insulin resistance; endometriosis, endometritis, and related conditions; epididymitis; erythropoietin resistance; fever; fibromyalgia or analgesia; glomerulonephritis; graft versus host disease/transplant rejection; Graves' disease; Guillain-Barre syndrome; Hashimoto's disease; hemolytic anemia; hemorrhagic shock; hyperalgesia; inflammatory conditions of a joint and rheumatic diseases including, osteoarthritis, rheumatoid arthritis, juvenile (rheumatoid) arthritis, seronegative polyarthritis, ankylosing spondylitis, Reiter's syndrome and reactive arthritis, Still's disease, psoriatic arthritis, enteropathic arthritis, polymyositis, dermatomyositis, scleroderma, systemic sclerosis, vasculitis (e.g., Kawasaki's disease), cerebral vasculitis, Lyme disease, staphylococcal-induced arthritis, Sjogren's syndrome, rheumatic fever, polychondritis and polymyalgia rheumatica and giant cell arteritis; inflammatory eye disease, as may be associated with, for example, corneal transplant; inflammatory eye disease, as may be associated with, e.g., corneal transplant; inflammatory bowel disease; ischemia, including cerebral ischemia; Kawasaki's disease; learning impairment; lung diseases; lupus nephritis; multiple sclerosis; myasthenia gravis; myopathies; neuroinflammatory diseases; neurotoxicity; ocular diseases and conditions, including ocular degeneration and uveitis; osteoporosis; pain, including cancer-related pain; Parkinson's disease; pemphigus; periodontal disease; Pityriasis rubra pilaris; pre-term labor; prostatitis and related conditions; psoriasis and related conditions; psoriatic arthritis; pulmonary fibrosis; reperfusion injury; rheumatic fever; rheumatoid arthritis; sarcoidosis; scleroderma; septic shock; side effects from radiation therapy; Sjogren's syndrome; sleep disturbance; spondyloarthropathies; systemic lupus erythematosus; temporal mandibular joint disease; thyroiditis; tissue transplantation or an inflammatory condition resulting from strain, sprain, cartilage damage, trauma, and orthopedic surgery; vasculitis; or an inflammatory condition resulting from strain, sprain, cartilage damage, trauma, orthopedic surgery, infection or other disease processes.

In one class of embodiments, the methods include administering to the subject an isolated or recombinant moiety selected from the group consisting of a soluble WSX-1 polypeptide, a p28 polypeptide, a soluble gp130 polypeptide, an EBI3 polypeptide, a soluble WSX-1/p28 polypeptide complex, a soluble WSX-1/EBI3 polypeptide complex, a soluble WSX-1/IL-27 polypeptide complex, a soluble gp130/IL-27 complex, a soluble gp130/p28 polypeptide complex, a soluble gp130/EBI3 polypeptide complex, a p28 polypeptide and a soluble WSX-1 polypeptide, an EBI3 polypeptide and a soluble WSX-1 polypeptide, IL-27 and a soluble WSX-1 polypeptide, a soluble gp130 polypeptide and a p28 polypeptide, a soluble gp130 polypeptide and IL-27, a soluble gp130 polypeptide and a EBI3 polypeptide, and a variant thereof. In embodiments in which a combination of recombinant or isolated polypeptides are administered (e.g., a p28 polypeptide and a soluble WSX-1 polypeptide), the polypeptides can but need not form a complex, and the polypeptides can be co-administered or separately administered.

In another class of embodiments, the methods include administering to the subject a moiety that specifically binds to or modulates an activity of a gp130/WSX-1/IL-27 complex, or that modulates formation of the complex in a cell (e.g., at the plasma membrane), thereby treating the subject for the condition. The moiety can be, for example, an antibody, an antagonist, an agonist, and an activity modulator. Optionally, the moiety potentiates formation or activity of a gp130/WSX-1/IL-27 complex.

In either class of embodiments, the methods optionally include diagnosing the patient with the inflammatory condition prior to said administering. A therapeutically effective amount of the moiety is typically administered to the subject. Optionally, the subject is monitored for response to the treatment. In one class of embodiments, after initiation of treatment the subject displays decreased inflammation, for example, reduced numbers of inflammatory cells, a reduction in the number of IL17$^+$T cells in circulation or at the site of inflammation, and/or decreased expression of IL17.

It will be evident that relevant complexes can optionally be formed in vivo. For example, in embodiments in which a polypeptide is administered, the polypeptide can form an active complex with endogenous protein(s). As one example, when a soluble WSX-1 polypeptide (e.g., a WSX-1Fc fusion protein) is administered to the subject, the WSX-1 can form a complex with endogenous p28 and/or IL-27, leading to therapeutic results. A polypeptide to be administered is optionally a variant having a higher affinity for the receptor components, e.g., than wild-type protein (e.g., a variant p28 having a higher affinity for WSX-1 or the WSX-1/gp130 receptor complex than does a corresponding naturally occurring p28 from which the variant is derived, or a variant soluble WSX-1 having increased affinity for gp130).

In one aspect, the methods include administering to the subject a therapeutically effective amount of a combination of the moiety and at least a second compound. The second compound is typically one that is used to treat the inflammatory condition, for example, a standard of care or experimental treatment. Exemplary second compounds include, but are not limited to, immune modulators that affect IL-23, L-12, IL-6 or TGF (e.g., antibodies specific to IL-12 p40, p35 or IL-23 p19); antibodies or reagents that antagonize the functions of IL-1 (e.g., anakinra (Kineret®), soluble IL-1 receptor) and TNF (e.g., anti-TNF antibodies, etanercept, infliximab, and leflunomide); a cytotoxic agent; an immunosuppressive agent (e.g., cyclophosphamide); a B-cell surface marker antagonist; an antibody to a B-cell surface marker; a CD20 antibody, e.g., Rituximab, see US 20060051345); a CD5, CD28, or CD40 antibody or blocking agent; a corticosteroid (e.g., prednisone), CTLA4-Ig, an alpha-4-integrin antibody or antagonist such as natalizumab (Tysabri®), mycophenolate mofetil, a statin, an LFA-1 or CD-11a antibody or blocking agent (see U.S. patent application publication 20050281817 by Jardieu et al. entitled "Method for treating multiple sclerosis"), an interleukin-12 antibody, a beta interferon (e.g., an interferon β-1a such as Avonex® or Rebif®, or an interferon β-1b such as Betaseron®), glatiramer acetate (Copaxone®), a CD52 antibody such as alemtuzuman (CamPath®), an interleukin receptor antibody such as daclizumab (Zenapax®, an antibody to the interleukin-2 receptor alpha subunit), etc. In one class of embodiments, the second compound is transforming growth factor beta (TGF-β).

In one embodiment, the subject has never been previously treated with drug(s) to treat the inflammatory condition and/or has never been previously treated with a moiety of the invention. In another embodiment, the subject has been previously treated with drug(s) to treat the inflammatory condition and/or has been previously treated with such a moiety.

Typically, the subject is eligible for treatment for the inflammatory condition, i.e., an eligible subject. For the purposes herein, such eligible subject is one who is experiencing, has experienced, or is likely to experience, one or more signs, symptoms or other indicators of the inflammatory condition; has been diagnosed with the inflammatory condition, whether, for example, newly diagnosed, previously diagnosed with a new relapse or exacerbation, previously diagnosed and in remission, etc; and/or is at risk for developing the inflammatory condition.

Administration

As will be understood by those of ordinary skill in the art, the appropriate doses of moieties of the invention (e.g., polypeptides, complexes, antibodies, etc.) will be generally around those already employed in clinical therapies wherein similar moieties are administered alone or in combination with other therapeutics. Variation in dosage will likely occur depending on the condition being treated. The physician administering treatment will be able to determine the appropriate dose for the individual subject. Preparation and dosing schedules for commercially available second compounds administered in combination with the moieties may be used according to manufacturers' instructions or determined empirically by the skilled practitioner.

For the prevention or treatment of disease, the appropriate dosage of the moiety and any second compound administered in combination with the moiety will depend on the type of disease to be treated, as defined above, the severity and course of the disease, whether the moiety or combination is administered for preventive or therapeutic purposes, previous therapy, the patient's clinical history and response to the antibody or combination, and the discretion of the attending physician. The moiety or combination is suitably administered to the patient at one time or more typically over a series of treatments.

Depending on the type and severity of the disease, about 1 µg/kg to 50 mg/kg (e.g. 0.1-20 mg/kg) of the moiety is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. Typically, the clinician will administer a moiety of the invention (alone or in combination with a second compound) until a dosage(s) is reached that provides the required biological effect. The progress of the therapy of the invention is easily monitored by conventional techniques and assays.

The moiety can be administered by any suitable means, including parenteral, topical, subcutaneous, intraperitoneal, intrapulmonary, intranasal, and/or intralesional administration. Parenteral infusions include intramuscular, intravenous, intraarterial, intraperitoneal, or subcutaneous administration. Intrathecal administration is also contemplated (see, e.g., U.S. patent application publication 2002/0009444 by Grillo-Lopez). In addition, the moiety may suitably be administered by pulse infusion, e.g., with declining doses of the moiety. Optionally, the dosing is given intravenously or subcutaneously, and optionally by intravenous infusion(s). Each exposure may be provided using the same or a different administration means. In one embodiment, each exposure is by intravenous administration.

As noted, the moiety can be administered alone or in combination with at least a second compound. These second compounds are generally used in the same dosages and with administration routes as used heretofore, or about from 1 to 99% of the heretofore-employed dosages. If such second compounds are used, optionally they are used in lower amounts than if the moiety were not present, so as to eliminate or reduce side effects caused thereby.

The administration of the moiety of the invention and any second compound can be done simultaneously, e.g., as a single composition or as two or more distinct compositions using the same or different administration routes. Alternatively, or additionally, the administration can be done sequentially, in any order. In certain embodiments, intervals ranging from minutes to days, to weeks to months, can be present between the administrations of the two or more compositions. For example, the moiety may be administered first, followed by the second compound of the invention. However, simultaneous administration or administration of the second compound of the invention first is also contemplated.

A third, fourth, etc. compound is optionally administered in combination with the moiety and the second compound.

Similarly, treatment for symptoms secondary or related to the inflammatory condition (e.g., spasticity, incontinence, pain, fatigue, etc.) can be administered to the subject, e.g., during treatment with the moiety or combination.

Pharmaceutical Formulations

Therapeutic formulations of the moieties of the invention (e.g., polypeptides, complexes, antibodies, etc.) used in accordance with the present invention are prepared for storage by mixing a moiety having the desired degree of purity with optional pharmaceutically acceptable carriers, excipients, or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low-molecular-weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as Tween®, Pluronics®, or PEG.

Lyophilized formulations adapted for subcutaneous administration are described, for example, in U.S. Pat. No. 6,267,958 (Andya et al.). Such lyophilized formulations may be reconstituted with a suitable diluent to a high protein concentration and the reconstituted formulation may be administered subcutaneously to the mammal to be treated herein. Crystallized forms of the moiety are also contemplated. See, for example, U.S. 2002/0136719A1 (Shenoy et al.).

The formulation herein may also contain at least a second compound as necessary for the particular indication being treated, preferably those with complementary activities that do not adversely affect each other. For example, it may be desirable to further provide transforming growth factor beta (TGF-β), a cytotoxic agent (e.g. methotrexate, cyclophosphamide, or azathioprine), chemotherapeutic agent, immunosuppressive agent, cytokine, cytokine antagonist or antibody, growth factor, hormone, integrin, integrin antagonist or antibody (e.g., an LFA-1 antibody, or an alpha 4 integrin antibody such as natalizumab), interferon class drug such as IFN-beta-1a or IFN-beta-1b, an oligopeptide such as glatiramer acetate, intravenous immunoglobulin (gamma globulin), lymphocyte-depleting drug (e.g., mitoxantrone, cyclophosphamide, CamPath® antibodies, or cladribine), non-lymphocyte-depleting immunosuppressive drug (e.g., MMF or cyclosporine), cholesterol-lowering drug of the "statin" class, estradiol, drug that treats symptoms secondary or related to lupus or MS (e.g., spasticity, incontinence, pain, fatigue), a TNF inhibitor, disease-modifying anti-rheumatic drug, nonsteroidal antiinflammatory drug, corticosteroid (e.g., methylprednisolone, prednisone, dexamethasone, or glucorticoid), levothyroxine, cyclosporin A, somatastatin analogue, anti-metabolite, a T- or B-cell surface antagonist/antibody, etc., or others as noted above in the formulation.

The type and effective amounts of such other agents depend, for example, on the amount of moiety present in the formulation, the type of inflammatory condition being treated, and clinical parameters of the subjects.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug-delivery systems (for example, liposomes, albumin microspheres, microemulsions, nano-particles and nanocapsules) or in macroemulsions. Such techniques are disclosed, e.g., in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

Discussion of Related Technologies

There are several cytokines or cytokine specific antagonists that are currently in development or commercially available:

A number of recombinant cytokines are used in a variety of clinical settings. These include IL-2, GM-CSF, IL-11, IL-12 and type I IFNs. These proteins are primarily being used as stimulators of immune cells and to act as growth factors or to enhance anti-cancer or viral responses. Few cytokines have been used to inhibit the immune system; for example, IL-10, which works indirectly on accessory cell functions necessary for T cell functions and which was being developed specifically with Crohn's disease and Inflammatory Bowel Disease as targets, and TGF. Success with these has been limited.

Antagonists of IL-12 p40 have been tested in clinical trials for patients with Crohn's disease with some success.

Antagonists of IL-15 are in clinical trials for arthritis based on the observation that this cytokine was involved in the development of this disease.

The IL-1 receptor antagonist is a commercially available product that is used to treat patients with rheumatoid arthritis. This is a product that blocks the interaction of the pro-inflammatory cytokine IL-1 with its receptor.

Amgen, Schering Plough and Centrocor (amongst others) have developed antibodies/antagonists specific for the cytokine TNF-α which are currently used in the treatment of patients with rheumatoid arthritis. This is an approach that relies on the neutralization of endogenous cytokine to prevent inflammation. A similar approach has been investigated with antibodies specific for IL-1 and IL-6. One safety issue is that these treatments are associated with the development of opportunistic infections including TB and toxoplasmosis.

Differences/Advantages Over Other Products

Many of these products (in particular IL-10) fail to directly target the T cell response during inflammation. Since WSX-1 is expressed by T cells, it is anticipated that strategies that target this receptor will have a much more specific effect than some of the other approaches that are currently being used or developed. Additionally, many of the current targets are single molecules downstream of T cell activity whereas p28/WSX-1 (and other fusion proteins and complexes described herein) directly target many of these factors (e.g., IL-2, IFN-gamma, IL-4, IL-17, TNF, IL-6) and can additionally increase expression of IL-10, thereby amplifying their therapeutic effect. Additionally, while side effects are noted with many cytokines (IL-2, IL-12, IFNs) we have not observed any obvious signs of clinical disease in mice treated with recombinant IL-27.

Nucleic Acid and Polypeptide Sequences and Variants

Sequences for a variety of naturally occurring WSX-1, gp130, p28, and EBI3 proteins and nucleic acids are publicly available. See, for example, protein sequence id NP_663634 and nucleotide sequence accession number NM_145659 for human p28, protein sequence id NP_005746 and nucleotide sequence accession number NM_005755 for human EBI3, protein sequence id NP_004834 and nucleotide sequence accession number NM_004843 for human WSX-1, protein sequence id NP_002175 and nucleotide sequence accession number NM_002184 for human gp 130, protein sequence id NP_663611.1 and nucleotide sequence accession number NM_145636.1 for murine p28, protein sequence id NP_056581.1 and nucleotide sequence accession number NM_015766 for mouse EBI3, protein sequence id NP_057880.1 and nucleotide sequence accession number NM_016671 for mouse WSX-1, and protein sequence id NP_034690 and nucleotide sequence accession number NM_010560 for mouse gp130. Sequences homologous or substantially identical to these nucleotide or amino acid sequences are also of interest in the present invention. As noted herein, various soluble and/or fusion variants of such proteins have been described (see, e.g., U.S. patent application publication 20040185049 and Wirtz et al., supra), and recombinant varieties of p28 and EBI3 are commercially available.

A number of additional, novel polypeptides are described herein, including novel WSX-1 and p28 fusion proteins. Such fusion proteins can include antibody domains and, as detailed above, are optionally based on bispecific antibodies.

In one aspect, the invention provides a variety of polynucleotides encoding the novel polypeptides of the invention. For example, one embodiment provides a nucleic acid that encodes a recombinant or isolated WSX-1 fusion protein, wherein the fusion protein comprises one or more domains that recognize a cell-specific marker or one or more polypeptide domains derived from p28 or EBI3. The nucleic acid optionally encodes one or more polypeptide domains selected from: an antibody domain, an Fc region, a p28 domain, or an EBI3 domain, as well as encoding a WSX-1 polypeptide. Another exemplary embodiment provides a nucleic acid that includes a recombinant or isolated p28 fusion protein. As for the preceding embodiments, the nucleic acid optionally encodes one or more of an antibody domain, an Fc region, and an EBI3 domain, as well as a p28 polypeptide.

One of skill will appreciate that the invention provides many related sequences with the functions described herein, for example, polynucleotides encoding a WSX-1 fusion protein, a p28 fusion protein, a gp130 fusion protein, an EBI3 fusion protein, a soluble WSX-1 polypeptide, a soluble gp130 polypeptide, etc.

Because of the degeneracy of the genetic code, many polynucleotides equivalently encode a given polypeptide sequence. Polynucleotide sequences complementary to any of the above described sequences are included among the polynucleotides of the invention. Similarly, an artificial or recombinant nucleic acid that hybridizes to a polynucleotide indicated above under highly stringent conditions over substantially the entire length of the nucleic acid (and is other than a naturally occurring polynucleotide) is a polynucleotide of the invention.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally similar sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid, while retaining the relevant function. Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional or tagging sequence (introns in the nucleic acid, poly His or similar sequences in the encoded polypeptide, etc.), is a conservative variation of the basic nucleic acid or polypeptide.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. Table 1 sets forth example groups that contain natural amino acids of like chemical properties, where substitutions within a group is a "conservative substitution".

TABLE 1

Conservative Amino Acid Substitutions

| Nonpolar and/or Aliphatic Side Chains | Polar, Uncharged Side Chains | Aromatic Side Chains | Positively Charged Side Chains | Negatively Charged Side Chains |
|---|---|---|---|---|
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Nucleic Acid Hybridization

Comparative hybridization can be used to identify nucleic acids of the invention, including conservative variations of nucleic acids of the invention. In addition, target nucleic acids which hybridize to a nucleic acid of the invention under high, ultra-high and ultra-ultra high stringency conditions, where the nucleic acids are other than a naturally occurring nucleic acid, are a feature of the invention. Examples of such nucleic acids include those with one or a few silent or conservative nucleic acid substitutions as compared to a given nucleic acid sequence of the invention.

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, N.Y.), as well as in *Current Protocols in Molecular Biology*, Ausubel et al., eds., *Current Protocols*, a joint venture between Greene Publishing Associates, Inc. and John Wiley & Sons, Inc., (supplemented through 2007) ("Ausubel"); Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook et al., *Molecular Cloning—A Laboratory Manual* (3rd Ed.), Vol. 1-3, Cold Spring Harbor Laboratory, Cold Spring Harbor, N.Y., 2000 ("Sambrook") for a description of SSC buffer). Often the high stringency wash is preceded by a low stringency wash to remove background probe signal. An example low stringency wash is 2×SSC at 40° C. for 15 minutes. In general, a signal to noise ratio of 5×(or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids that do not hybridize to each other under stringent conditions are still substantially identical if the polypeptides which they encode are substantially identical.

This occurs, e.g., when a copy of a nucleic acid is created using the maximum codon degeneracy permitted by the genetic code.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a WSX-1, p28, EBI3, or gp130 polypeptide, or the amino acid sequence of a WSX-1, p28, EBI3, or gp130 polypeptide) refers to two or more sequences or subsequences that have at least about 60%, about 80%, about 90%, about 95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues (nucleotides or amino acids) is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available. "Orthologs" are genes in different species that evolved from a common ancestral gene by speciation. Normally, orthologs retain the same or similar function in the course of evolution. As used herein "orthologs" are included in the term "homologs."

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Current Protocols in Molecular Biology, Ausubel et al., eds., Current Protocols, a joint venture between Greene Publishing Associates, Inc. and John Wiley & Sons, Inc., supplemented through 2007).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Making and Isolating Recombinant Polypeptides

Generally, nucleic acids encoding a polypeptide of the invention or for use in the methods or compositions of the invention can be made by cloning, recombination, in vitro synthesis, in vitro amplification and/or other available methods. Essentially any nucleic acid can be custom or standard ordered from any of a variety of commercial sources, such as Operon Technologies Inc. (Alameda, Calif.). In addition, a variety of recombinant methods can be used for expressing an expression vector that encodes a polypeptide of the invention. Recombinant methods for making nucleic acids, expression and isolation of expressed products are well known and are described, e.g., in Sambrook, Ausubel, and Innis et al. (eds.), *PCR Protocols: A Guide to Methods and Applications*, Academic Press Inc., San Diego, Calif. (1990).

A plethora of kits are commercially available for the purification of plasmids or other relevant nucleic acids from cells, (see, e.g., EasyPrep™, FlexiPrep™, both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both. See, Giliman & Smith, Gene 8:81 (1979); Roberts, et al., Nature, 328:731 (1987); Schneider, B., et al., Protein Expr. Purif. 6435:10 (1995); Ausubel supra, Sambrook supra, and Berger and Kimmel, Guide to Molecular Cloning Techniques, Methods in Enzymology volume 152 Academic Press, Inc., San Diego, Calif. A catalogue of bacteria and bacteriophages useful for cloning is provided, e.g., by the ATCC, e.g., The ATCC Catalogue of Bacteria and Bacteriophage published yearly by the ATCC. Additional basic procedures for sequencing, cloning and other aspects of molecular biology and underlying theoretical considerations are also found in Watson et al. (1992) Recombinant DNA Second Edition, Scientific American Books, NY.

Other useful references, e.g. for cell isolation and culture (e.g., for subsequent nucleic acid or polypeptide isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg N.Y.) and Atlas and Parks (eds) *The Handbook of Microbiological Media* (1993) CRC Press, Boca Raton, Fla.

A variety of protein isolation and detection methods are known and can be used to isolate polypeptides, e.g., from recombinant cultures of cells expressing the recombinant fusion or soluble proteins of the invention. A variety of protein isolation and detection methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods, 2nd Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3rd Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Additional details regarding protein purification and detection methods can be found in Satinder Ahuja ed., *Handbook of Bioseparations*, Academic Press (2000).

Soluble WSX-1 and gp130 polypeptides, p28 polypeptides, and EBI3 polypeptides can thus be expressed and purified by one of skill. Alternatively, a number of such polypeptides are commercially available. For example, recombinant p28 and EBI3 are available from Abnova Corporation (www (dot) abnova (dot) corn (dot) tw). Where polypeptide complexes are desired, the two (or more) polypeptide components of the complex are optionally co-expressed and purified together as a complex, or the components can be purified separately and then combined to form the complex. The components are optionally noncovalently associated in the complex, or are optionally covalently connected by a chemical crosslinker or the like in the complex.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

Interleukin 27 Negatively Regulates Development of Interleukin 17-Producing T Helper 17 Cells During Chronic CNS Inflammation Recent studies have focused on the events that influence the development of $T_H$-17 cells associated with autoimmunity, such as experimental autoimmune encephalitis, but relatively little is known about the cytokines that antagonize $T_H$-17 effector responses. The experiments herein show that interleukin (IL)-27R-deficient mice chronically infected with *Toxoplasma gondii* developed severe neuro-inflammation that was CD4+ T cell-dependent and associated with a prominent IL-17 response. In vitro, IL-27 treatment of naive primary T cells suppressed the development $T_H$-17 cells induced by IL-6 and TGF-β, which was dependent on STAT1 but independent of SOCS3-mediated inhibition of IL-6 signaling. Thus IL-27, a potent inhibitor of $T_H$-17 cell development, may be a useful target for treating inflammatory diseases mediated by these cells. Similarly, the fusion proteins and complexes described hereinabove provide useful approaches for treating inflammatory diseases mediated by these cells.

While the T helper type 1 ($T_H$1)-$T_H$2 paradigm has dominated studies of T helper cell function for almost 20 years[1], recent work has identified a novel subset of CD4+ T cells that produce IL-17A, IL-17F, TNF and IL-6 in response to IL-23[2,3]. These '$T_H$-17' lymphocytes have been implicated as mediators of the inflammation associated with several autoimmune diseases, including experimental autoimmune encephalitis (EAE) and collagen induced arthritis[3-

7. As a consequence there has been an interest in defining the ontogeny of these pathological CD4+ T cells and the factors that regulate their activities[8-10]. While early studies established a role for IL-23 in promoting the production of $T_H$-17 cells, later work showed that IL-23 is not a strong inducer de novo of $T_H$-17 cells. The observation that T cells from IL-23 deficient mice can secrete IL-17 when stimulated by IL-23[3] indicated that other factors promote the development of IL-17-producing cells[8]. Several recent reports have in fact identified a critical role for TGF-β and IL-6 for the de novo development of murine $T_H$-17 cells[11-13]. Although success in demonstrating the importance of IL-6 and TGF-β in their development has been relatively rapid (at least in mice), considerably less has been known about the physiological antagonists of $T_H$-17 cells.

IL-27, a heterodimeric cytokine composed of Epstein-Barr virus induced gene 3 (EBI3) and p28, signals through a receptor complex composed of IL-27R (WSX-1/TCCR) and gp130[14,15]. While expression of the IL-27R is confined to immune cells[15-18], its partner gp130, a shared receptor component of several cytokines including IL-6, is constitutively expressed on immune and non-immune cells[19,20]. Although few studies have directly addressed the events that lead to the production of IL-27, a current model holds that IL-27 heterodimer is produced by activated APCs[21]. Initial reports focused on the ability of IL-27 to promote T cell proliferation and development of $T_H$1 responses[18,22]; subsequent studies have indicated that it can also limit $T_H$1 and $T_H$2 responses involved in resistance to various parasitic infections. Thus, IL-27R-deficient (Il27ra−/−) mice develop exaggerated T helper cell responses during the acute stages of toxoplasmosis, Chagas' disease, leishmaniasis and following helminth challenge[23-26]. Recently, a similar phenotype has been linked to IL-27 inhibition of IL-2 production[27], but it was unclear whether IL-27 has additional suppressive effects on other T cell subsets or functions.

While there is an appreciation of the role of IL-27 in acute models of inflammation[8], there has been a limited understanding of its role in chronic disease and its tissue specific effects. Evidence suggests that IL-27 is produced during inflammation in the CNS[28], but a possible function for IL-27 during chronic toxoplasmosis has not been addressed; it has been unclear whether IL-27 has pro- or anti-inflammatory effects in the 'immunoprivileged' CNS.

The results described herein demonstrate that Il27ra−/− mice chronically infected with *T. gondii* control parasite replication in the brain but develop a lethal CD4+ T cell-mediated pathology associated with an exaggerated $T_H$-17 response. Additional ex vivo studies showed that IL-27—or even its p28 component alone, to a lesser extent—were able to antagonize the development of $T_H$-17 cells. The suppressive activity of IL-27 was independent of SOCS3-dependent inhibition of gp130 signaling but dependent on STAT1. Together, these findings identify IL-27 to be an antagonist of $T_H$-17 cell development and therefore indicate a possible therapeutic target for treating inflammatory diseases associated with $T_H$-17 cells.

Results

Production of IL-27 During Toxoplasmic Encephalitits

Figure 1A:
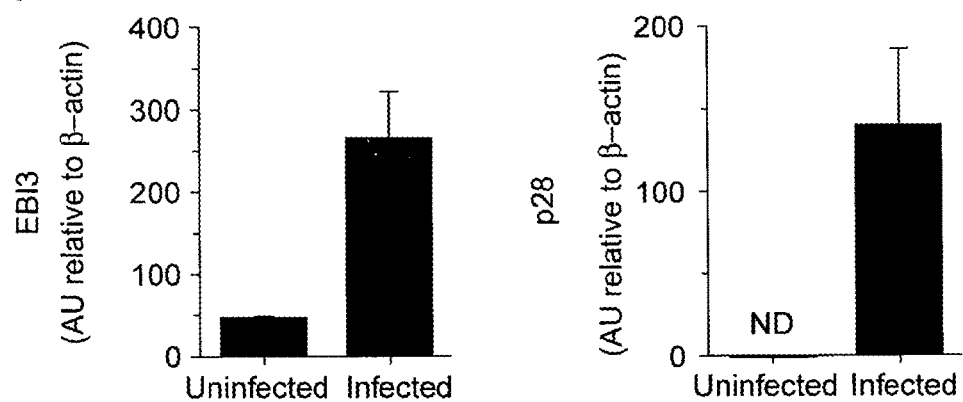
FIG. 1 Panels A and B illustrate expression of IL-27 in the brain during TE. Panel A presents bar graphs of results from quantitative real-time PCR on total cellular RNA isolated from the brains of uninfected and chronically infected (Day 30 post infection) WT C57BL/6 mice to detect ebi3 and Il27 (p28) mRNA. Panel B presents bar graphs of results from quantitative real-time PCR of ebi3 and Il27 mRNA isolated from primary WT C57BL/6 astrocyte cultures. $1\times10^6$ astrocytes were plated/well and stimulated for 18 hr followed by isolation of RNA. Results of real-time PCR were normalized against mRNA for Actb (β-actin). Data are representative of two independent experiments. ND, not detected.
Figure 1B:
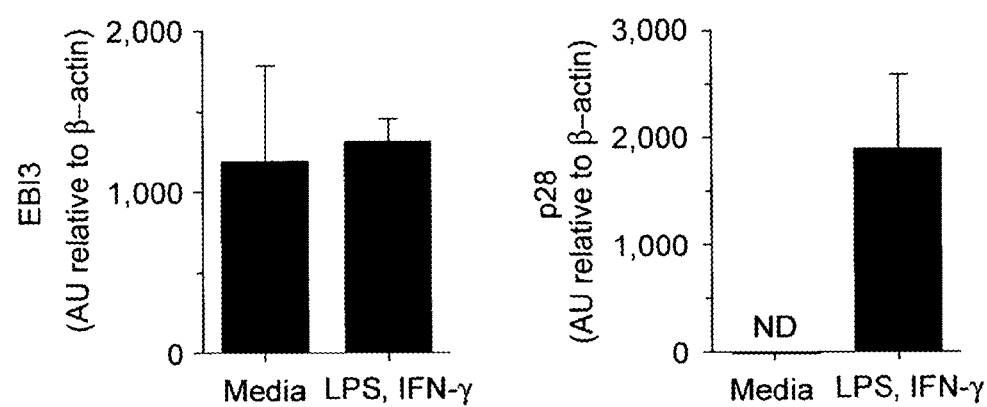
Figure 2A:
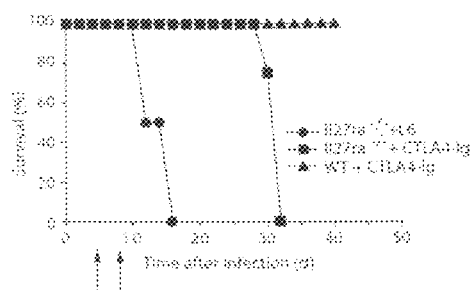
FIG. 2 Panels A-H illustrate that IL-27 is required for resistance to chronic TE. Panel A presents a line graph showing survival of Il27ra−/− (n=8) and WT C57BL/6 (n=10) mice infected intraperitoneally with 20 cysts from the Me49 strain of *T. gondii* and treated with CTLA4-Ig. Arrows denote days of CTLA4-Ig treatment. Panel B presents a line graph showing survival of Il27ra−/− (n=10) or WT (n=10) mice treated with sulfadiazine starting at day 5 after infection (arrow). Treatment was stopped after two weeks. Panel C presents photographs of histopathological analysis of the liver and lungs at day 14 and 30 after infection from Il27ra−/− mice treated with CTLA4-Ig. Panel D presents photographs for analysis of pathology in the brain of chronically infected WT and Il27ra−/− mice at day 30 after infection with astrocyte specific marker GFAP. Panel E presents a bar graph of parasite DNA isolated from the brains of chronically infected WT and Il27ra−/− mice measured by real-time quantitative PCR. Results are representative of two experiments with 4-5 mice per group. Panels F—H present bar graphs showing NO (Panel F), IFN-γ (Panel G), and IL-12 (Panel H) production from BMNC isolated from WT or Il27ra−/− mice restimulated in vitro in the presence of STAg; after 48 hrs the supernatants were collected and analyzed. Results are representative of four independent experiments with similar results and the error bars designating the SEM.
Figure 2C:
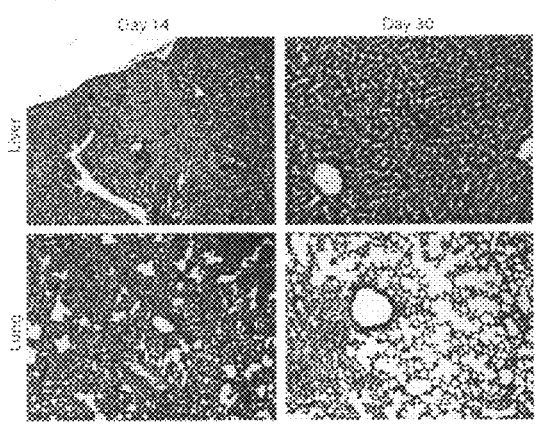
Figure 2B:
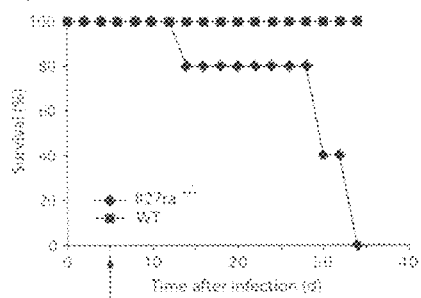
Figure 2D:
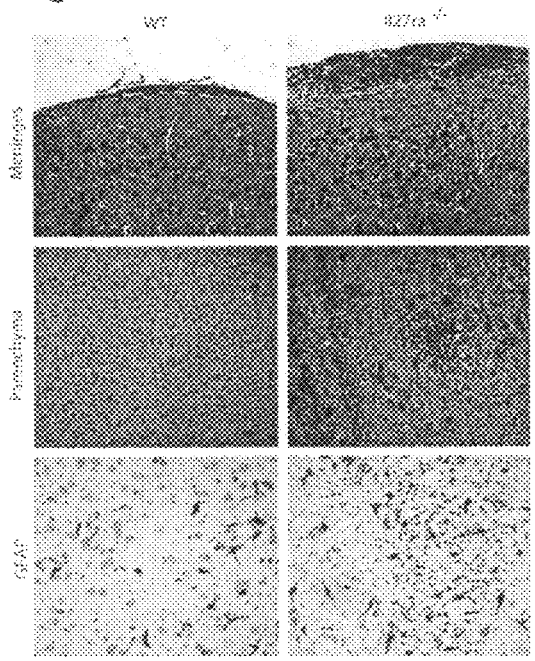
Figures 2E, 2F:
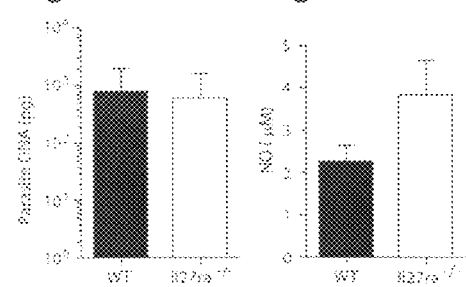
Figures 2G, 2H:
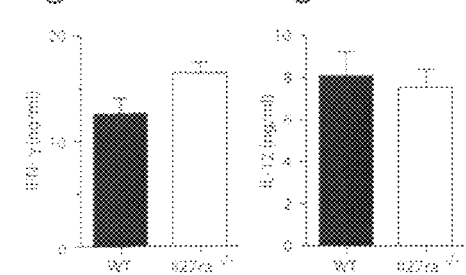

Real-time PCR was used to quantify relative levels of the transcripts for IL-27 during TE. Low to minimal amounts of mRNA for ebi3 (gene for EBI3) and Il27 (gene for p28) were detected in uninfected brains. In tissues from chronically infected mice, however, there was a >3 fold increase in the amount of ebi3 mRNA in the brain and a >500 fold increase in the mRNA amounts for Il27 (FIG. 1 Panel A). Given that dendritic cells and macrophages are thought to be sources of IL-27 in peripheral tissues 4, it is possible that the elevated ebi3 and Il27 transcripts detected during TE are due to the migration of these cells into the CNS. Alternatively, resident brain cells that are also capable of producing IL-27 include microglia and brain resident monocytes[29]. Activation of astrocytes, a subset of resident cells in the CNS, during TE and their ability to produce cytokines in response to infection[30] suggest that they may represent a source of IL-27. However, although primary astrocytes from WT mice expressed basal levels of ebi3 mRNA, no increase was observed in response to stimulation with LPS plus IFN-γ (FIG. 1 Panel B). In contrast, amounts of Il27 mRNA increased almost 2000 fold after stimulation with LPS and IFN-γ. Together these observations suggest that both components of IL-27 are produced locally during TE and that activated astrocytes can express both EBI3 and p28.

The Role of IL-27 During Chronic Infection with *T. gondii*

Previous focus on IL-27 implicated a role for it in the differentiation of naive T cells into effector $T_H$1 cells[14,31-34]. However, Il27ra−/− mice were found to generate robust $T_H$1 responses when challenged with *T. gondii*, though the mice succumbed to an acute, lethal CD4+ T cell-dependent inflammatory disease characterized by exaggerated production of IFN-γ and IL-2[26,27] associated with severe liver and lung pathology[26].

Given the susceptibility of Il27ra−/− mice to acute toxoplasmosis, several strategies were devised that would allow chronic infection to develop. The first of these was to treat infected mice with CTLA4-Ig, an antagonist of CD28-dependent co-stimulation of T cells[35], on days 7 and 10 post infection. After treatment with CTLA4-Ig, infected Il27ra−/− mice survived over 14 days after infection and progressed to the chronic stage; however, the treatment did not provide long-term protection, as the Il27ra−/− mice that received the CTLA4-Ig died within five weeks of infection. The lethality observed after CTLA4-Ig treatment did not appear to be a secondary consequence of CTLA4-Ig-mediated immune suppression as WT mice that received the same treatment survived (FIG. 2 Panel A). Histological analysis of liver and lung revealed that although Il27ra−/− mice treated with CTLA4-Ig survived the acute phase they still developed prominent immune cell infiltration, necrosis and inflammation in these organs at day 14 post infection (FIG. 2 Panel C). The pathology was not apparent in infected WT mice whether or not they had been treated with CTLA4-Ig (data not shown). In contrast to what was observed in the liver and lungs at this time point, there were no histological signs of inflammation observed in the brain of either Il27ra−/− or WT mice (data not shown).

In Il27ra−/− mice that progressed to the chronic stage of infection (day 30), however, the pathology present in the liver and lungs during acute infection had resolved (FIG. 2 Panel C). In contrast, in the brain and CNS, Il27ra−/− mice displayed areas of intense inflammation, numerous perivascular cuffs in the parenchyma and severe meningitis (FIG. 2 Panel D). WT mice, on the other hand, had minimal to mild TE. Moreover, astrocyte activation, as assessed by staining for glial fibrillary protein (GFAP), revealed that although infection led to increased expression of this structural protein in WT animals this was markedly increased in the Il27ra−/− mice (FIG. 2 Panel D). In a complimentary approach to allow Il27ra−/− mice to progress to the chronic stage, treatment with the anti-parasitic drug sulfadiazine starting at day 5 post infection, which inhibits parasite replication but does not eradicate infection, also prevented acute mortality in the Il27ra−/− mice. After cessation of drug treatment, WT mice did not manifest clinical disease, but the Il27ra−/− mice developed symptoms of disease associated with severe CNS pathology and died within 2-3 weeks (FIG. 2 Panel B). The data presented in the remainder of this example is thus derived from mice that were allowed to develop chronic disease through treatment with CTLA4-Ig or sulfadiazine and no differences were apparent between these different experimental groups.

Given reports that IL-27 can augment the production of IFN-γ[18,22,31-34], a cytokine critical for the control of *T. gondii* in the CNS[36], the enhanced inflammation seen in the brain in the absence of IL-27 signaling could be a consequence of a failure to make IFN-γ and an inability to control parasite replication. However, no measurable difference in parasite burden was found in the brains of chronically infected Il27ra−/− and WT mice (FIG. 2 Panel E). Moreover, mononuclear cells isolated from the brains (BMNC) of WT and Il27ra−/− mice were not deficient in their ability to produce the IFN-γ dependent anti-parasitic effector molecule nitric oxide (NO) (FIG. 2 Panel F). Consistent with this observation, BMNC from WT and Il27ra−/− mice stimulated with STAg (soluble *Toxoplasma* antigens) produced similar levels of IL-12 and IFN-γ (FIG. 2 Panels G and H). Those findings indicated that the severe neuro-inflammation in Il27ra−/− mice was not the result of a defect in IFN-γ production or an increase in parasite burden. Because IL-27 inhibits the production of IL-2 by CD4+ T cells[27,37] it was possible that in the absence of IL-27 signaling heightened production of this T cell growth factor in the brain could contribute to the observed immunopathology. However, consistent with previous reports, no detectable amounts of Il2 (IL-2) mRNA or protein were found in the brain of chronically infected WT mice and this was not altered in the absence of the IL-27R (data not shown). Similarly, there were no detectable transcripts for Il4 (IL-4) or Il3 (IL-13), two $T_H2$-associated cytokines, in the brain of these experimental groups. Lastly, examination of other T cell subsets revealed the presence of a minor population of Foxp3+ T regulatory ($T_{reg}$) cells in the brain, but there was no difference in cell numbers between chronically infected WT or Il27ra−/− mice (data not shown).

Absence of IL-27R Results in Accumulation of Pathogenic CD4+ T Cells

Given the prominent infection-induced CNS inflammation in the absence of the IL-27R, experiments were performed to identify the phenotype of the infiltrating cells. In accord with the histopathology, analysis of BMNC isolated from chronically infected mice showed a marked increase in the number of cells recovered from Il27ra−/− brains (P≤0.05; FIG. 3 Panel A) and a significant increase in the number and percentage of CD4+ T cells (P≤0.05) as well as the number of CD8+ T cells recovered (FIG. 3 Panel B). Despite differences in the composition of the T cell populations, analysis of the T cells from the brains of WT and Il27ra−/− mice displayed an activated phenotype of CD44hi and CD62Llow (FIG. 8). Moreover, monocytes from both sets of mice displayed an activated phenotype characterized by the heightened expression of major histocompatibility complex class II on their surface (data not shown). However, while there were no differences in the number of resident microglia (CD11bint, CD45int) there was a significant increase in the number of infiltrating macrophages (CD11bhi, CD45hi) in the absence of the IL-27R (P≤0.05; FIG. 3 Panel B).

In the studies mentioned above, one of the striking features noted in the chronically infected Il27ra−/− mice is the significant increase in the number of CD4+ T cells present in the brain. Although infiltrating lymphocytes are required for the control of TE[38]; they can also contribute to the development of CNS pathology during this infection[39]. To determine if the CD4+ T cells were involved in the lethal disease seen in the chronically infected Il27ra−/− mice, the mice were treated with a depleting mAb specific for CD4 at four weeks post infection and monitored for survival. Analyses of the mice following treatment with the anti-CD4 mAb revealed a depletion >95% of CD4+ T cells in the spleen and a 50% reduction in the brain (FIG. 3 Panel C). Survival of the Il27ra−/− mice treated with anti-CD4 mAb was longer than 60 days after infection, whereas the majority of the untreated mice developed severe pathology in the brain and died from disease by day 50 (FIG. 3 Panel D). Furthermore, histological analysis 7 days after this treatment revealed decreased inflammation in the paranchyma and meninges (FIG. 3 Panel E). Together, these data established that infiltrating CD4+ T cells contribute to the lethal pathology in the brain observed during TE in the absence of IL-27.

IL-27 Inhibits Production of IL-17 by Antigen Experienced T Cells

The recognition that the neuro-pathology in chronically infected Il27ra−/− mice is not a consequence of a defective $T_H1$ response but is instead mediated by CD4+ T cells led to the decision to examine the possible role of the recently described $T_H$-17 subset of CD4+ T cells in the lethal pathology. Because $T_H$-17 cells have been characterized by the production of IL-17, IL-6 and TNF, involved in the development of disease in a model of CNS inflammation[3], the amount of mRNA transcripts for these cytokines was assessed by real-time PCR using RNA derived from the brain of chronically infected WT and Il27ra−/− mice. Whereas both WT and Il27ra−/− mice expressed comparable amounts of Il6 (IL-6) and Tnf (TNF), transcripts for Il17 (IL-17) were only detected in the samples from Il27ra−/− mice (FIG. 4 Panel A).

Although there are multiple cellular sources (astrocytes, microglia, macrophages, T cells) for IL-6 and TNF in the brain during TE, the production of IL-17 is largely restricted to T cells. Accordingly, BMNC from Il27ra−/− mice were restimulated in the presence of STAg produced significantly more IL-17, IL-6 and TNF than cells from WT mice (FIG. 4 Panel B). Low amounts of IL-17 were also produced by WT BMNCs stimulated with STAg, which was augmented by adding IL-23 and was almost completely blocked by addition of IL-27 (FIG. 4 Panel C). Furthermore, intracellular staining of CD4+ and CD8+ T cell populations in BMNC preparations from chronically infected WT and Il27ra−/− mice revealed elevated IL-17 production by cells in the brain of Il27ra−/− mice (FIG. 4 Panel D). Together, those results suggest that IL-27 regulates inflammation in the CNS during chronic TE by limiting $T_H$-17 activity.

IL-27 Inhibits Production of IL-17 CD4+ and CD8+ T Cells

Figure 5B:
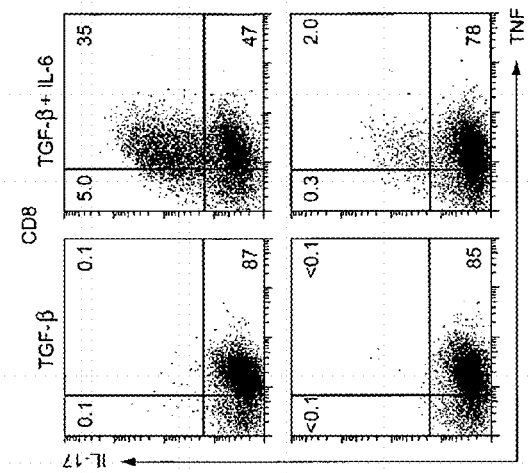
FIG. 5 Panels A-C illustrate that IL-27 inhibits production of IL-17 by in vitro generated $T_H$-17 cells. Panels A-C illustrate flow cytometry on CD4+ (Panels A and C) and CD8+ (Panels B and C) T cells isolated from C57BL/6 mice and activated with anti-CD3 and anti-CD28 under $T_H$-17-inducing conditions in the presence or absence of IL-27 (Panels A, B, and C) or p28 (Panel C). The CD4+ and CD8+ T cells cultured for four and three days respectfully were stimulated with PMA and ionomycin in the presence of BFA for 4 hrs before staining for intracellular IL-17 (Panels A, B, and C), TNF (Panels A and B) or IFN-γ (Panel C). Plots are gated on CD4+ or CD8+ T cells where specified; numbers in quadrants represent the frequency of cells in each. Data are representative of three independent experiments.
Figure 5A:
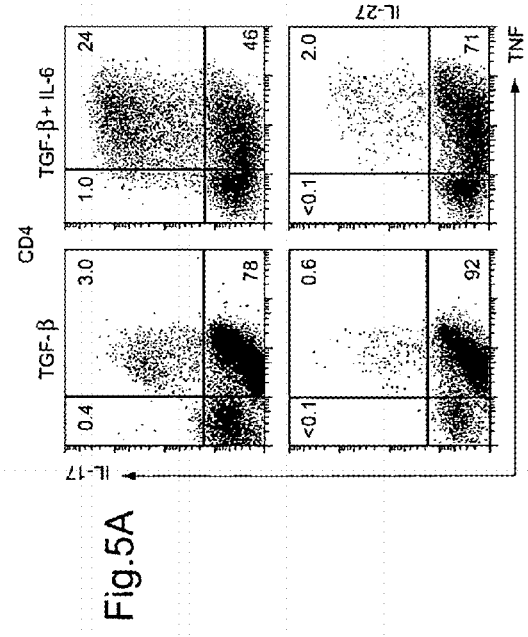
Figure 5C:
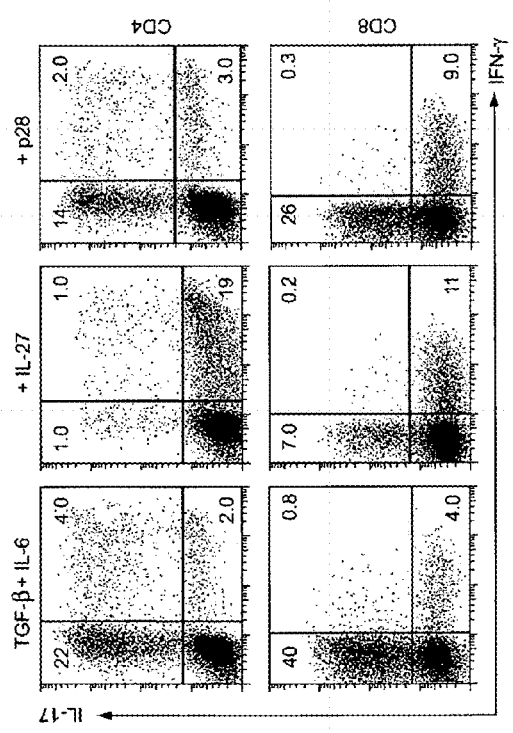

Recent reports on the differentiation of $T_H$-17 cells in vitro have concluded that TGF-β and IL-6 are required for the generation of these cells from naive CD4+ T cells, while blockage of IFN-γ and IL-4 supports an environment favorable for $T_H$-17 development[3,11-13,40,41]. Therefore, naive CD4+ and CD8+ T cells isolated from the spleens of C57BL/6 mice were cultured under these conditions to directly evaluate the ability of IL-27 to inhibit T cell production of IL-17. Following stimulation with PMA and ionomycin almost all the T cells produced TNF and a significant population co-expressed IL-17 and TNF. Consistent with the studies presented above, the addition of IL-27 efficiently inhibited IL-17 production by CD4+ and CD8+ T cells, but did not alter the production of TNF by these cells (FIG. 5 Panels A and B). In the absence of PMA and ionomycin stimulation the percentage and mean fluorescent intensity of IL-17 producing cells were lower, but IL-27 was still a potent antagonist of this activity (FIG. 9).

The original description of p28 indicated that this protein could be secreted by itself but, unlike IL-27, did not promote T cell proliferation or promote IFN-γ production[14]. In light of the finding that IL-27 inhibits IL-17 production and p28 expression increases dramatically in activated astrocytes, while EBI3 expression was unaltered (FIG. 1 Panel B), studies were performed to determine if p28 by itself could inhibit production of IL-17 by T cells. CD4+ or CD8+ T cells isolated from C57BL/6 mice were stimulated under IL-17 inducing conditions in the presence of p28. Although not as efficient as IL-27, p28 treatment alone could inhibit the production of IL-17 by CD4+ and CD8+ T cells (FIG. 5 Panel C).

gp130 Associated Cytokines have Distinct Effects on $T_H$-17 Development

Recent work by multiple groups has revealed a role for IL-6 in the development of $T_H$-17 cells[11-13]. Because IL-6 and IL-27 signal through a shared receptor component, gp130, it was possible that the ability of IL-27 to inhibit production of IL-17 was a consequence of competition with IL-6 for gp130 binding and or signaling. To address this issue, a series of experiments were performed using CD4+ T cells isolated from the spleens of WT C57BL/6 mice. When these cells were activated with anti-CD3 plus anti-CD28 antibodies in the presence of IL-23 or TGF-β under non-polarizing conditions (anti-IFN-γ, anti-IL-4) robust secretion of IL-17 occurred, and the addition of IL-27 could inhibit production of IL-17 in a dose dependent manner (FIG. 6 Panels A and B). Subsequent neutralization of IL-6 in the culture conditions (using an anti-IL-6 antibody) resulted in a decrease in IL-17 production, similar to previous reports[11]; however, even in those conditions the addition of IL-27 still reduced the levels of IL-17 in a dose dependent manner (FIG. 6 Panels A and B), indicating that IL-27 and IL-6, closely related cytokines, have contrasting effects on $T_H$-17 cells.

One of the direct consequences of signaling by many type I cytokines is the downstream activation of SOCS proteins, which leads to the suppression of T cell responses through a negative regulatory feedback loop[42]. It has previously been reported that like IL-6, IL-27 induces SOCS3 expression in CD4+ T cells[27,37] and it has been proposed that this activity accounts for the ability of IL-27 to inhibit the production of L-2[37]. To explore the possible role of this pathway on the ability of IL-27 to inhibit $T_H$-17 activity, gp130Y757F mice, which express a hypermorphic mutation in gp130, were used[43]; in these transgenic mice, wild-type gp130 has been replaced with a version in which the Tyr757 residue is replaced with phenylalanine. Previous studies have associated this residue with the binding of SOCS3 and SHP2, and consistent with this observation this substitution results in IL-6 mediated hyper-activation of STAT3 and impaired activation of the Ras-ERK pathway[44].

T cells from the gp130Y757F mice stimulated with IL-6 resulted in exaggerated and prolonged STAT3 phosphorylation (FIG. 6 Panel C and data not shown). The peak of STAT3 phosphorylation occurred at 1 hr and remained elevated in the gp130Y757F T cells after 24 hrs (FIG. 6 Panel C and data not shown). Subsequently, CD4+ T cells were isolated from gp130Y757F mice and WT littermate controls and grown under $T_H$-17-inducing conditions for 4 days followed by measurement of intracellular IL-17. In these experiments this mutation in gp130 led to an increase by a factor of 3 in the frequency of IL-17+ cells without restimulation with PMA and ionomycin (FIG. 6 Panel D) although this effect was less apparent when PMA and ionomycin stimulation was used (FIG. 10). Analysis of culture supernatants revealed that gp130Y757F CD4+ T cells secreted five times more IL-17 than WT CD4+ T cells (FIG. 6 Panel E). Those data establish that IL-6-mediated production of SOCS3 limits the ability of IL-6 to promote IL-17 and are in agreement with the recent report of a role for SOCS3 as a negative regulator of IL-23-induced IL-17 production[45]. Nevertheless, the addition of IL-27 antagonized the production of IL-17 by the gp130Y757F $T_H$-17 cells with or without PMA and ionomycin restimulation (FIG. 6 Panel D and FIG. 10) and IL-27 was able to reduce the levels of secreted IL-17 by mutant and WT CD4+ T cells in a dose dependent manner (FIG. 6 Panel E). Finally, to directly examine the role of SOCS3 in limiting IL-17 production by IL-27 Cre$^{MMTV}$ Socs$^{fl/fl}$ mice with a conditional deletion of Socs3 in CD4+ T cells were used. When Cre$^{mmtv}$ Socs$^{fl/fl}$ CD4+ T cells were grown under $T_H$-17-inducing conditions in the presence of IL-27, IL-17 production was still inhibited (FIG. 6 Panel F). Together, those results indicate that the ability of IL-27 to inhibit IL-17 production cannot be attributed to a SOCS3-mediated dampening of gp130-IL-6 signaling.

IL-27 Inhibits IL-17 Production Through STAT1

Although IL-6 and IL-27 are closely related cytokines and share gp130 mediated signaling, the data presented thus far demonstrate they have opposing effects on IL-17 production. That conclusion implies that the inhibitory signals from IL-27 are mediated through the IL-27R specific component, and while IL-6 activates STAT3 predominantly, several studies have linked the unique IL-27R chain to the activation of STAT1 and subsequent induction of the transcription factor T-bet[32,33]. Therefore, in order to determine if the ability of IL-27 to inhibit IL-17 production involved these transcription factors, CD4+ T cells from either Stat1−/− or Tbx21−/− (T-bet-deficient) mice were stimulated under $T_H$-17 inducing conditions in the presence or absence of IL-27. As before, the addition of IL-27 resulted in a marked inhibition of IL-17 production by WT and T-bet-deficient CD4+ T cells, but the effect was compromised in the absence of STAT1 (FIG. 7 Panel A). Those data identify a dominant role for STAT1 in the ability of IL-27 to antagonize $T_H$-17 function.

To examine the role of STAT1 in vivo, Stat1−/− mice were acutely infected with *T. gondii* and IL-17 production was monitored. Restimulation of splenocytes with STAg at day 7 post infection showed that Stat1−/− splenocytes secrete more IL-17 than their WT counterparts (FIG. 7 Panel B). Although consistent with the in vitro data, the in vivo data have to be interpreted with caution because the Stat1−/− mice are unable to control parasite replication[46]; yet the results are similar to studies with EAE[7] which previously provided in vivo evidence for STAT1-mediated inhibition of $T_H$-17 activity.

Discussion

Recently a unique subset of T cells linked to the production of IL-17, TNF and IL-6 have been implicated in the development of the pathology observed in models of multiple sclerosis, inflammatory bowel disease and rheumatoid arthritis[3-7]. While aberrant $T_H$-17 responses are associated with autoimmunity, they also have a role in acute resistance to challenge with the pathogens klebsiella and toxoplasma[47-49], but in those situations the $T_H$-17 responses do not lead to autoimmunity. The implication of those results, similar to what is known for most T cell responses, is that mechanisms exist to appropriately regulate $T_H$-17 activity; there is now clear evidence that IFN-γ and IL-4 are required for other T helper cells to antagonize $T_H$-17 cells[3,13,40,41].

The results herein showed that Il27ra[−/−] mice chronically infected with *T. gondii* develop severe neuropathology mediated by CD4[+] T cells, associated with abnormal T cell production of IL-17, IL-6 and TNF, which indicates a role for IL-27 in the regulation of $T_H$-17 activity. The suppressive effects of IL-27 on $T_H$-17 cells was demonstrated by experiments in which IL-27 inhibited production of IL-17 by BMNC from chronically infected mice stimulated with IL-23, as well as TCR transgenic CD4+ T cells and splenic derived CD4+ and CD8+ T cells. Those results indicate that IL-27 is likely to regulate $T_H$-17 cells at other sites of inflammation.

As highlighted earlier, IL-6 and IL-27 are closely related cytokines which both signal through gp130 and their cellular effects are mediated through activation of the JAK-STAT pathway[8,52], yet they have very different effects on $T_H$-17 activity. A recent report has linked IL-23 induced activation of STAT3 to promoting CD4[+] T cell production of IL-17[53], a finding consistent with the ability of IL-6, a major activator of STAT3, to promote $T_H$-17 activity. Similarly, the observation that the gp130Y757F T cells produce elevated amounts of IL-17 is in agreement with current models that indicate that SOCS3 is part of a classic negative feedback loop that limits IL-6 mediated signaling. However, although IL-27 activates SOCS3[27,37] the ability of IL-27 to reduce $T_H$-17 activity in the absence of IL-6 and in the gp130Y757F- or SOCS3-deficient CD4[+] T cells indicates that it has inhibitory effects distinct from simply antagonizing IL-6 mediated signaling.

Although initial reports focused on the pro-inflammatory activities of IL-27, there is a growing recognition that IL-27 antagonizes pathological T cell responses. Recent studies showing that IL-27 inhibits T helper cell production of IL-2 have provided insights into its possible anti-inflammatory activities[27]. Moreover, the ability of IL-27 to decrease IL-17 production in the presence of exogenous IL-2 indicates that decreased $T_H$-17 activity is not simply a consequence of reduced levels of IL-2 (FIG. 11). Indeed, some data suggest that IL-2 preferentially promotes IFN-γ and not IL-17 responses[11].

The data presented here demonstrates that IL-27 employs STAT1 to suppress IL-17 production by CD4[+] and CD8+ T cells, an effect that is independent of T-bet. That observation contrasts with a previous report that IL-27 inhibition of IL-2 production was independent of STAT1[27]. Although the activation of STAT1 by IFN-γ or IL-27 has been predominantly associated with the development of $T_H$1 responses, the present data highlight that this signaling pathway also mediates anti-inflammatory activities. This conclusion is supported by the observation of enhanced development of $T_H$-17 cells in vivo in Stat1[−/−] mice[7,54] and by the fact that neutralization of IFN-γ promotes IL-17 production[3,40,41] Moreover, the hypothesis that IL-27 mediated activation of STAT1 represents an endogenous inhibitory pathway of IL-17-producing T cells in the CNS may explain the finding that Stat1[−/−] mice develop more severe EAE[55]. Although the latter finding has been attributed to the lack of IFN-γ signaling[8], it seems likely that it may also be a function of reduced IL-27 activity. At present the molecular basis for the inhibitory effects of STAT1 in different experimental systems is unknown, yet literature highlighting the role of various STATs in repression of immune responses continues to grow[56,57].

The inhibition of IL-17 production by p28 alone raises several questions about the biology of how this protein binds to its receptor and transduces its inhibitory effects. One possibility is that the secretion of p28 may dimerize with constitutively available EBI3 leading to the formation of IL-27 or p28 may signal in trans in a fashion similar to IL-6[19]. Although none of the immuno-stimulatory activities of IL-27 have been previously ascribed to p28[14], a better understanding of the biology of this secreted protein may provide insight into ways that it can be used therapeutically. The findings presented here suggest a relevance of p28 signaling by itself and the importance of IL-27 as a physiological antagonist of $T_H$-17 activity. Although strong evidence has been uncovered that blockade of IL-17 activity ameliorates disease in a variety of autoimmune disorders[3, 50,51,58], the neutralization of IL-17 specifically targets the cytokines downstream of $T_H$-17 activity. In contrast, stimulation by IL-27 and/or its p28 subunit can directly antagonize antigen specific $T_H$-17 cells and provide an opportunity to specifically target the cellular sources of IL-17, which may provide a more efficient approach for the treatment of certain autoimmune diseases.

Methods

Mice and Parasites

C57BL/6 mice were obtained from Jackson laboratories and WSX-1-/- (Il27ra-/-) mice were provided by Dr. Christiaan Saris (Amgen Inc.). The transgenic DO11.10 mice with a TCR specific for the chicken ovalbumin peptide (OVA(323-339)) in the context of 1-Ad, Stat1-/- mice and Tbx21-/- mice were provided by Dr Phillip Scott (University of Pennsylvania, Philadelphia, Pa.). The gp130Y757F and CreMMTVSocs3fl/fl mice were previously described[43,45]. Mice were housed and bred in specific pathogen free facilities in the Department of Pathobiology at the University of Pennsylvania in accordance to institutional guidelines.

The Me49 strain of *T. gondii* was prepared from chronically infected CBA/ca mice and experimental animals were infected intraperitoneally with 20 cysts. Il27ra-/- mice were administered 200 µg of CTLA4-Ig (Bristol Meyers Squibb) intraperitoneally. on day 7 and 10 post-infection or treated on day 5 post-infection with 200 mg/L of sulfadiazine (Sigma) in their drinking water for two weeks. Soluble toxoplasma antigen (STAg) was prepared from tachyzoites of the RH strain as described previously[59]. For histological examinations, livers, lungs and brains were collected from animals, fixed in 10% formalin, embedded in paraffin, sectioned and stained with hematoxylin and eosin. To determine astrocyte activation brain sections were stained for GFAP as previously described[30]. To measure parasite burden the 35-fold repetitive *T. gondii* B1 gene was amplified by real-time PCR using SYBR® Green PCR Master mix (Applied Biosystems) in an AB7500 fast real-time PCR machine (Applied Biosystems) using previously described conditions[30]. In order to normalize the $C_t$ values obtained from the experimental samples, the mouse β-actin gene was amplified under the same conditions[30].

Analysis of Brain Mononuclear Cells (BMNC)

Isolation of BMNC from chronically infected WT and Il27ra-/- mice was performed in accordance with a previously described protocol[30,60]. Cells were processed for ex vivo surface staining and intracellular staining as previously described[27]. Cells were surface stained using antibodies against CD4, CD8, CD44, CD45, I-A/I-E (BD Pharmingen), CD62L and CD11b (eBioscience). T cells were stained intracellularly using antibodies against IL-17 (BD Pharmingen), IFN-γ and TNF (eBioscience). Samples were acquired on a FACScaliber flow cytometer (Becton Dickenson) and the results were analyzed using FloJo software (TreeStar Inc.). BMNC were plated at a final density of 2×105 cells per well in a final volume of 200 µl in 96-well round bottom plates (Costar). Cells were stimulated with or without STAg (50 µg/ml) in the presence or absence of recombinant mIL-27 (100 ng/ml; Amgen Inc.), IL-23 (10 ng/ml; DNAX) or both. Supernatants were collected after 48 hrs and the levels of IL-2, IFN-γ, IL-12, IL-17, TNF and IL-6 were measured by ELISA. Nitric oxide (NO) levels were measured by the use of a Greiss assay.

Real-time Quantitative PCR Analysis

Total cellular RNA was isolated from perfused and homogenized brains of chronically infected WT and Il27ra−/− mice as well as uninfected WT mice using standard procedures and converted to cDNA as described[26]. In addition, total RNA was isolated from WT C57BL/6 primary astrocyte cultures and used to make cDNA. Primary astrocytes were harvested from the brains of 1-3 day old mice as described previously[30], and the purity of astrocyte cultures as judged by glial fibrillary acidic proteins (GFAP) staining (anti-mouse GFAP, BD Pharmingen) was consistently greater than 90%. Expression of TNF, IL-6, IL-27p28 and EBI3 was determined using primers obtained from Qiagen and carried out in an AB7500 fast real-time PCR machine using Power Sybr Green® reagents (Applied Biosystems). Expression of IL-17 was determined using Taqman® primers, probe and reagents obtained from Applied Biosystems. The β-actin housekeeping gene was used as a normalization control in both cases.

Generation of $T_H$-17 Cells

IL-17-producing CD4+ and CD8+ T cells were produced as described elsewhere[11,40] with modified changes. Briefly, splenocytes isolated from the aforementioned mice were depleted of CD8+ and NK1.1+ cells to enrich for CD4+ T cells or they were depleted of CD4+ and NK1.1+ cells to enrich for CD8+ T cells by magnetic bead separation (Polysciences). Cells were plated in 96 well plates (Costar) at a density of 5×106 cells/ml. The Tg CD4+ T cells were stimulated with 5 µg/ml of OVA peptide, while the other T cells were stimulated with anti-TCR antibody (anti-CD3; 1 g/ml; eBioscience) and anti-CD28 (1 µg/ml; eBioscience). For production of $T_H$-17 cells cultures were supplemented with either recombinant mouse IL-23 (10 ng/ml; DNAX) or human TGF-β (1 ng/ml; R & D) alone or in combination with IL-6 (10 ng/ml; eBioscience), TNF (10 ng/ml; eBioscience) and IL-1β, (10 ng/ml; BD Pharmingen). Additionally IFN-γ and IL-4 were neutralized in the cultures using anti-IFN-γ (10 µg/ml; clone XMG1.2) and anti-IL-4 (10 µg/ml; clone 11B11). Recombinant IL-27 (10 ng/ml; Amgen) was added where stated. Recombinant p28 was provided by eBioscience and used at a concentration of 100 ng/ml where stated. The CD8+ T cells were harvested on day 3, while the CD4+ T cells were supplemented with fresh medium and reagents on day 3 and harvested on day 4. Both cell types were subsequently stained for intracellular IL-17, TNF and IFN-γ in the presence or absence of PMA and ionomycin stimulation plus Brefeldin A (Sigma).

Statistics

An unpaired Student t test was used to determine significant differences and a P value <0.05 was considered significant.

References for Example 1

1. Mosmann, T. R. & Coffman, R. L. TH1 and TH2 cells: different patterns of lymphokine secretion lead to different functional properties. *Annu Rev Immunol* 7, 145-73 (1989).
2. Aggarwal, S., Ghilardi, N., Xie, M. H., de Sauvage, F. J. & Gurney, A. L. Interleukin-23 promotes a distinct CD4 T cell activation state characterized by the production of interleukin-17. *J Biol Chem* 278, 1910-4 (2003).
3. Langrish, C. L. et al. IL-23 drives a pathogenic T cell population that induces autoimmune inflammation. *J Exp Med* 201, 233-40 (2005).
4. Cua, D. J. et al. Interleukin-23 rather than interleukin-12 is the critical cytokine for autoimmune inflammation of the brain. *Nature* 421, 744-8 (2003).
5. Murphy, C. A. et al. Divergent pro- and antiinflammatory roles for IL-23 and IL-12 in joint autoimmune inflammation. *J Exp Med* 198, 1951-7 (2003).
6. Yen, D. et al. IL-23 is essential for T cell-mediated colitis and promotes inflammation via IL-17 and IL-6. *J Clin Invest* 116, 1310-6 (2006).
7. Chen, Y. et al. Anti-IL-23 therapy inhibits multiple inflammatory pathways and ameliorates autoimmune encephalomyelitis. *J Clin Invest* 116, 1317-26 (2006).
8. Hunter, C. A. New IL-12-family members: IL-23 and IL-27, cytokines with divergent functions. *Nat Rev Immunol* 5, 521-31 (2005).
9. McKenzie, B. S., Kastelein, R. A. & Cua, D. J. Understanding the IL-23-IL-17 immune pathway. *Trends Immunol* 27, 17-23 (2006).
10. Bettelli, E. & Kuchroo, V. K. IL-12- and IL-23-induced T helper cell subsets: birds of the same feather flock together. *J Exp Med* 201, 169-71 (2005).
11. Veldhoen, M., Hocking, R. J., Atkins, C. J., Locksley, R. M. & Stockinger, B. TGFbeta in the context of an inflammatory cytokine milieu supports de novo differentiation of IL-17-producing T cells. *Immunity* 24, 179-89 (2006).
12. Bettelli, E. et al. Reciprocal developmental pathways for the generation of pathogenic effector T(H)17 and regulatory T cells. *Nature* (2006).
13. Mangan, P. R. et al. Transforming growth factor-beta induces development of the T(H)17 lineage. *Nature* (2006).
14. Pflanz, S. et al. IL-27, a heterodimeric cytokine composed of EBI3 and p28 protein, induces proliferation of naive CD4(+) T cells. *Immunity* 16, 779-90 (2002).
15. Pflanz, S. et al. WSX-1 and glycoprotein 130 constitute a signal-transducing receptor for IL-27. *J Immunol* 172, 2225-31 (2004).
16. Villarino, A. V. et al. Positive and negative regulation of the IL-27 receptor during lymphoid cell activation. *J Immunol* 174, 7684-91 (2005).
17. Sprecher, C. A. et al. Cloning and characterization of a novel class I cytokine receptor. *Biochem Biophys Res Commun* 246, 82-90 (1998).
18. Chen, Q. et al. Development of Th1-type immune responses requires the type I cytokine receptor TCCR. *Nature* 407, 916-920 (2000).
19. Heinrich, P. C., Behrmann, I., Muller-Newen, G., Schaper, F. & Graeve, L. Interlukin-6-type cytokine signaling through the gp130/Jak/STAT pathway. *Biochem. J.* 334, 297-314 (1998).
20. Taga, T. & Kishimoto, T. Gp130 and the interleukin-6 family of cytokines. *Annu Rev Immunol* 15, 797-819 (1997).
21. Villarino, A. V. & Hunter, C. A. Biology of recently discovered cytokines: discerning the pro- and anti-inflammatory properties of interleukin-27. *Arthritis Res Ther* 6, 225-33 (2004).

22. Yoshida, H. et al. WSX-1 is required for the initiation of Th1 responses and resistance to *L. major* infection. *Immunity* 15, 569-78 (2001).
23. Artis, D. et al. The IL-27 receptor (WSX-1) is an inhibitor of innate and adaptive elements of type 2 immunity. *J Immunol* 173, 5626-34 (2004).
24. Hamano, S. et al. WSX-1 is required for resistance to Trypanosoma cruzi infection by regulation of proinflammatory cytokine production. *Immunity* 19, 657-67 (2003).
25. Rosas, L. E. et al. Interleukin-27R (WSX-1/T-Cell Cytokine Receptor) Gene-Deficient Mice Display Enhanced Resistance to *Leishmania donovani* Infection but Develop Severe Liver Immunopathology. *Am J Pathol* 168, 158-69 (2006).
26. Villarino, A. et al. The IL-27R (WSX-1) is required to suppress T cell hyperactivity during infection. *Immunity* 19, 645-55 (2003).
27. Villarino, A. V. et al. IL-27 limits IL-2 production during Th1 differentiation. *J Immunol* 176, 237-47 (2006).
28. Li, J., Gran, B., Zhang, G. X., Rostami, A. & Kamoun, M. IL-27 subunits and its receptor (WSX-1) mRNAs are markedly up-regulated in inflammatory cells in the CNS during experimental autoimmune encephalomyelitis. *J Neurol Sci* 232, 3-9 (2005).
29. Sonobe, Y. et al. Production of IL-27 and other IL-12 family cytokines by microglia and their subpopulations. *Brain Res* 1040, 202-7 (2005).
30. Wilson, E. H., Wille-Reece, U., Dzierszinski, F. & Hunter, C. A. A critical role for IL-10 in limiting inflammation during toxoplasmic encephalitis. *J Neuroimmunol* 165, 63-74 (2005).
31. Hibbert, L., Pflanz, S., De Waal Malefyt, R. & Kastelein, R. A. IL-27 and IFN-alpha signal via Stat1 and Stat3 and induce T-Bet and IL-12Rbeta2 in naive T cells. *J Interferon Cytokine Res* 23, 513-22 (2003).
32. Kamiya, S. et al. An indispensable role for STAT1 in IL-27-induced T-bet expression but not proliferation of naive CD4+ T cells. *J Immunol* 173, 3871-7 (2004).
33. Takeda, A. et al. Cutting edge: role of IL-27/WSX-1 signaling for induction of T-bet through activation of STAT1 during initial Th1 commitment. *J Immunol* 170, 4886-90 (2003).
34. Lucas, S., Ghilardi, N., Li, J. & de Sauvage, F. J. IL-27 regulates IL-12 responsiveness of naive CD4+ T cells through Stat1-dependent and -independent mechanisms. *Proc Natl Acad Sci USA* 100, 15047-52 (2003).
35. Egen, J. G., Kuhns, M. S. & Allison, J. P. CTLA-4: new insights into its biological function and use in tumor immunotherapy. *Nat Immunol* 3, 611-8 (2002).
36. Suzuki, Y., Conley, F. K. & Remington, J. S. Importance of endogenous IFN-gamma for prevention of toxoplasmic encephalitis in mice. *J Immunol* 143, 2045-50 (1989).
37. Owaki, T. et al. IL-27 suppresses CD28-mediacted IL-2 production through suppressor of cytokine signaling 3. *J Immunol* 176, 2773-80 (2006).
38. Gazzinelli, R., Xu, Y., Hieny, S., Cheever, A. & Sher, A. Simultaneous depletion of CD4+ and CD8+ T lymphocytes is required to reactivate chronic infection with *Toxoplasma gondii*. *J Immunol* 149, 175-80 (1992).
39. Israelski, D. M. et al. Treatment with anti-L3T4 (CD4) monoclonal antibody reduces the inflammatory response in toxoplasmic encephalitis. *J Immunol* 142, 954-8 (1989).
40. Harrington, L. E. et al. Interleukin 17-producing CD4+ effector T cells develop via a lineage distinct from the T helper type 1 and 2 lineages. *Nat Immunol* 6, 1123-32 (2005).
41. Park, H. et al. A distinct lineage of CD4 T cells regulates tissue inflammation by producing interleukin 17. *Nat Immunol* 6, 1133-41 (2005).
42. Alexander, W. S. & Hilton, D. J. The role of suppressors of cytokine signaling (SOCS) proteins in regulation of the immune response. *Annu Rev Immunol* 22, 503-29 (2004).
43. Tebbutt, N. C. et al. Reciprocal regulation of gastrointestinal homeostasis by SHP2 and STAT-mediated trefoil gene activation in gp130 mutant mice. *Nat Med* 8, 1089-97 (2002).
44. Croker, B. A. et al. SOCS3 negatively regulates IL-6 signaling in vivo. *Nat Immunol* 4, 540-5 (2003).
45. Chen, Z. et al. Selective regulatory function of Socs3 in the formation of IL-17-secreting T cells. *Proc Natl Acad Sci USA* 103, 8137-8142 (2006).
46. Lieberman, L. A., Banica, M., Reiner, S. L. & Hunter, C. A. STAT1 plays a critical role in the regulation of antimicrobial effector mechanisms, but not in the development of Th1-type responses during toxoplasmosis. *J Immunol* 172, 457-63 (2004).
47. Kelly, M. N. et al. Interleukin-17/interleukin-17 receptor-mediated signaling is important for generation of an optimal polymorphonuclear response against *Toxoplasma gondii* infection. *Infect Immun* 73, 617-21 (2005).
48. Happel, K. I. et al. Divergent roles of IL-23 and IL-12 in host defense against *Klebsiella pneumoniae*. *J Exp Med* 202, 761-9 (2005).
49. Happel, K. I. et al. Cutting edge: roles of Toll-like receptor 4 and IL-23 in IL-17 expression in response to *Klebsiella pneumoniae* infection. *J Immunol* 170, 4432-6 (2003).
50. Koenders, M. I. et al. Blocking of interleukin-17 during reactivation of experimental arthritis prevents joint inflammation and bone erosion by decreasing RANKL and interleukin-1. *Am. J. Pathol.* 167, 141-149 (2005).
51. Lubberts, E. et al. Treatment with a neutralizing anti-murine interleukin-17 antibody after the onset of collagen-induced arthritis reduces joint inflammation, cartilage destruction, and bone erosion. *Arthritis Rheum.* 50, 650-659 (2004).
52. Watford, W. T. et al. Signaling by IL-12 and IL-23 and the immunoregulatory roles of STAT4. *Immunol Rev* 202, 139-56 (2004).
53. Cho, M. L. et al. STAT3 and NF-{kappa}B Signal Pathway Is Required for IL-23-Mediated IL-17 Production in Spontaneous Arthritis Animal Model IL-1 Receptor Antagonist-Deficient Mice. *J Immunol* 176, 5652-61 (2006).
54. Hashimoto, K. et al. Respiratory syncytial virus infection in the absence of STAT 1 results in airway dysfunction, airway mucus, and augmented IL-17 levels. *J Allergy Clin Immunol* 116, 550-7 (2005).
55. Bettelli, E. et al. Loss of T-bet, but not STAT1, prevents the development of experimental autoimmune encephalomyelitis. *J Exp Med* 200, 79-87 (2004).
56. Nguyen, K. B. et al. Interferon alpha/beta-mediated inhibition and promotion of interferon gamma: STAT1 resolves a paradox. *Nat Immunol* 1, 70-6 (2000).
57. Lee, C. K., Smith, E., Gimeno, R., Gertner, R. & Levy, D. E. STAT1 affects lymphocyte survival and proliferation partially independent of its role downstream of IFN-gamma. *J Immunol* 164, 1286-92 (2000).
58. Hellings, P. W. et al. Interleukin-17 orchestrates the granulocyte influx into airways after allergen inhalation in a mouse model of allergic asthma. *Am J Respir Cell Mol Biol* 28, 42-50 (2003).

59. Sharma, S. D., Mullenax, J., Araujo, F. G., Erlich, H. A. & Remington, J. S. Western blot analysis of the antigens of *Toxoplasma gondii* recognized by human IgM and IgG antibodies. *J. Immunol.* 131, 977-983 (1983).
60. Villegas, E. N. et al. Blockade of costimulation prevents infection-induced immunopathology in interleukin-10-deficient mice. *Infect. Immun.* 68, 2837-2844 (2000).

Example 2

Soluble WSX-1 Enhances Inhibition of IL-2 Production by IL-27

Total splenocytes were isolated from two Il27ra−/− mice (WSX-1 KO1 and WSX-1 KO2). The splenocytes were depleted of NK1.1+ and CD8+ cells to enrich for CD4+ T cells. The CD4+ T cells were then labeled with CFSE (carboxyfluoroscein succinimidyl ester) and stimulated with anti-CD3 antibody and anti-CD28 antibody. IL-27 with or without the sIL-27R Fc protein (a soluble WSX-1 polypeptide, an Fc fusion protein including WSX-1 extracellular domain sequence, provided by Amgen Inc.) was added to wells containing the cells. The sIL-27R Fc protein was incubated for 30 minutes with IL-27 prior to addition to the cell wells to facilitate binding. The cells were incubated for 48 hrs at 37° C. The supernatants were used in ELISA assays to measure the production of IL-2 and IFN-γ (FIG. 12).

Addition of the soluble WSX-1 fusion protein sIL-27R Fc potentiated inhibition of IL-2 and IFN-γ production by IL-27. The results demonstrate that the soluble receptor can function in the absence of endogenous receptor and indicate that the receptor can work in trans.

Example 3

A Central Role for Interleukin 27 and IL-6 Mediated Activation of STAT3 in T Cell Production of IL-10

IL-10 has a prominent role in regulating the balance between protective and pathological T cell responses. Consistent with this activity there are multiple sources of this cytokine including myeloid cells as well as a variety of T cell subsets. However, while there are many pathways that regulate innate production of IL-10, the factors that govern its production by the adaptive response are poorly understood. The studies presented in this example reveal that IL-27 and IL-6 are able to induce a variety of T cell populations to produce IL-10. This effect is dependent on the transcription factors STAT1 and STAT3 for IL-27, and STAT3 for IL-6. Together these studies identify a novel pathway that allows the immune system to temper inflammatory responses.

IL-10 was initially described as a $T_H2$ associated cytokine that inhibited the production of IFN-γ by $T_H1$ cells[1,2]. It was later recognized that this was an indirect effect and that its ability to temper $T_H1$ cell function was due to its ability to antagonize accessory cell activity. Thus, IL-10 reduced the ability of macrophages to produce pro-inflammatory cytokines such as IL-1, TNF and IL-12, and decreased expression of co-stimulatory and MHC molecules required for T cell responses[3-9]. While IL-10 has a variety of biological properties, one of its main roles in vivo is to limit inflammatory responses, consistent with its inhibitory effects on antigen presenting cells. This function was first highlighted in the initial reports that revealed that IL-10−/− mice spontaneously develop inflammatory bowel disease (IBD)[10]. Subsequent studies using mouse models of sepsis, infectious disease and autoimmunity have extended understanding of the role of IL-10 in the regulation of innate and adaptive responses associated with $T_H1$, $T_H2$ and $T_H17$ activities[11,13]. In the context of infectious disease, there are several examples of how the absence of IL-10 leads to enhanced resistance to pathogens, but also results in the development of an aberrant inflammatory response that can kill the host[14-16]. Together, these studies illustrate the central role of IL-10 in maintaining a balance between protective immunity and the development of pathology.

Given the important role of IL-10 in limiting inflammation perhaps it is not surprising that there are multiple sources of this immune-modulator, including macrophages and dendritic cells stimulated with microbial products. In addition, although IL-10 was initially characterized as a $T_H2$ cytokine[1,2], it is now recognized that Tr1 cells[17], CD25+[18,19] and CD25− regulatory T cells (Treg)[20,21] and $T_H1$ cells[22,23] also secrete IL-10. The relative importance of these different subsets as sources of IL-10 has been a long-standing question[24,25], but in recent years the link between Treg cells and IL-10 has dominated this area of research. Nevertheless, there is an established literature on the presence of IFN-γ+IL-10+T helper cells in a variety of disease settings[26,27], and several recent studies have highlighted the importance of IL-10-dependent immune suppression by CD4+ CD25-Foxp3-T cells that also produce IFN-γ during infection with *T. gondii* and in a non-healing model of *Leishmania major*[28,29]. Nevertheless, despite extensive evidence for the importance of T cell derived IL-10 to limit inflammation, the events that induce the production of this cytokine by T cells has remained unclear[24,25].

IL-10 is not the sole anti-inflammatory mediator used by the immune system to control inflammation, and the list of pathways (CTLA4, BTLA, PD1) involved in this process continues to grow. Recently the cytokine IL-27, a heterodimeric cytokine composed of Epstein-Barr induced protein 3 (EBI3) and p28[30], has been described as an antagonist of several T cell functions. This cytokine was initially identified as a factor that promotes the development of $T_H1$ cells[31,32], but subsequent reports highlighted that IL-27 can also limit $T_H1$, $T_H2$ and $T_H17$ responses involved in various models of infection and autoimmunity[32-40]. Indeed, studies in these laboratories revealed that, like IL-10−/− mice, IL-27ra−/− mice infected with *T. gondii* developed a lethal CD4+ T cell mediated response that was characterized by excessive production of pro-inflammatory cytokines, large areas of necrosis in the liver and the presence of severe immune cell infiltrates in multiple organs[14,33,38,41,42]. The similarities of these phenotypes not only highlight the important role that these anti-inflammatory cytokines play in regulating an ongoing immune response, but also suggest a potential link between these two immune modulators.

In order to better understand the effect of IL-27 on T cells, the production of 67 soluble immune mediators in the presence or absence of IL-27 were assayed. This analysis revealed that while IL-27 inhibited multiple cytokines associated with $T_H1$, $T_H2$ and $T_H17$ cells, surprisingly it also promoted the production of IL-10. This observation was mirrored in vivo as T cells from IL-27ra−/− mice chronically infected with *T. gondii* had a defect in their ability to make IL-10. In vitro studies revealed that IL-27 could enhance CD4+ and CD8+ T cell production of IL-10, but the majority of the IL-10+ T cells induced by IL-27 did not express Foxp3 indicating that IL-27 can stimulate IL-10 production by multiple T cell populations. Furthermore, the stimulation of T cells with IL-27 plus TGF-β resulted in an additive effect on IL-10, and IL-6 (which like IL-27 signals through gp130) when combined with TGF-β was also a potent inducer of IL-10. The ability of IL-27 to stimulate IL-10 production was independent of the intracellular signaling molecule STAT4 and the transcription factor T-bet, but was dependent on STAT1 and STAT3 activation, whereas IL-6 only requires STAT3. Collectively, these data provide a novel insight into the cytokine environment that promotes T cell production of IL-10 and the molecular events that underpin this regulatory pathway.

Results

IL-27 Induces T Cell Production of IL-10

While recent studies have highlighted the ability of IL-27 to inhibit T cell production of multiple pro-inflammatory cytokines[38, 43], a screen that could identify additional targets for IL-27 was of interest. Therefore, naïve CD4+ T cells from C57BL/6 mice were activated with anti-TCR (α-CD3) and α-CD28 antibodies in the presence of accessory cells under non-polarizing conditions (α-IFN-γ and α-IL-4) in the presence or absence of IL-27. After the cells were cultured for three days the supernatants were assayed for a panel of 67 secreted immune products using a Rodent Multi-Analyte Profile (RodentMA™). Consistent with previous reports the addition of IL-27 to these non-polarized cultures led to decreases in multiple cytokines associated with $T_H1$ (IFN-γ), $T_H2$ (IL-5) and $T_H17$ (IL-17) responses but also included GM-CSF, IL-1β, IL-3, MIP-1α and -β and lymphotactin (FIG. 14 Panel A). In addition, several other cytokines including IL-18, IL-6, IL-7 and chemokines including MCP-1, MCP-3, M-CSF, MMP-9 were unaltered by this treatment (Table 2). However, the most striking result was the observation that IL-27 led to a 1000-fold increase in the levels of IL-10 in these culture supernatants (FIG. 14 Panel A and Table 2).

TABLE 2

Rodent MAP results.

| | pg/ml | |
|---|---|---|
| | Non-polarizing | IL-27 |
| Apo A1 (Apolipoprotein A1) | 1.2E+05 | 1.3E+05 |
| Beta-2 Microglobulin | <LOW> | <LOW> |
| Calbindin | 51 | 51 |
| Clusterin | 19000 | 19000 |
| CRP (C Reactive Protein) | <LOW> | <LOW> |
| Cystatin-C | 64000 | 53000 |
| EGF (Epidermal Growth Factor) | 3.7 | 2.8 |
| Endothelin-1 | 8 | 5 |
| Eotaxin | 4.4 | 3 |
| Factor VII | 480 | 330 |
| FGF-9 (Fibroblast Growth Factor-9) | 550 | 460 |
| FGF-basic (Fibroblast Growth Factor-basic) | 800 | 470 |
| Fibrinogen | 1.70E+06 | 1.20E+06 |
| GCP-2 (Granulocyte Chemotactic Protein-2) | 5.4 | 4.4 |
| GM-CSF | 272 | 96 |
| Growth Hormone | <LOW> | <LOW> |
| GST-alpha (Glutathione S-Transferase alpha) | <LOW> | <LOW> |
| GST-Mu | 8700 | 6600 |
| Haptoglobin | 3.10E+05 | 2.90E+05 |
| IFN-gamma (Interferon-gamma) | 765 | 342 |
| IgA (Immunoglobulin A) | 1.6E+05 | 1.2E+05 |
| IL-10 (Interleukin-10) | 303 | 3480 |
| IL-11 (Interleukin-11) | 14 | 13 |
| IL-12p70 (Interleukin-12p70) | <LOW> | 9.9 |
| IL-17 (Interleukin-17) | 1900 | 820 |
| IL-18 (Interleukin-18) | 180 | 130 |
| IL-1alpha (Interleukin-1alpha) | 12 | 11 |
| IL-1beta (Interleukin-1beta) | 430 | 380 |
| IL-2 (Interleukin-2) | 638 | 570 |
| IL-3 (Interleukin-3) | 205 | 93 |
| IL-4 (Interleukin-4) | 8.8 | <LOW> |
| IL-5 (Interleukin-5) | 1600 | 670 |
| IL-6 (Interleukin-6) | 14 | 15 |
| IL-7 (Interleukin-7) | 17 | 23 |
| Insulin | 1.3* | 1.2* |
| IP-10 (Inducible Protein-10) | 108 | 121 |
| KC/GROalpha | <LOW> | <LOW> |
| Leptin | 42 | 21 |
| LIF (Leukemia Inhibitory Factor) | 2410 | 2580 |
| Lymphotactin | 1690 | 749 |
| MCP-1 (Monocyte Chemoattractant Protein-1) | 12 | 9 |
| MCP-3 (Monocyte Chemoattractant Protein-3) | 8.9 | 7.5 |
| MCP-5 (Monocyte Chemoattractant Protein-5) | 1.9 | 0.62 |
| M-CSF (Macrophage-Colony Stimulating Factor) | 17 | 13 |
| MDC (Macrophage-Derived Chemokine) | 1450 | 429 |
| MIP-1alpha (Macrophage Inflammatory Protein-1alpha) | 1300 | 410 |
| MIP-1beta (Macrophage Inflammatory Protein-1beta) | 1540 | 1340 |
| MIP-1gamma (Macrophage Inflammatory Protein-1gamma) | 170 | 110 |
| MIP-2 (Macrophage Inflammatory Protein-2) | 33 | 14 |
| MIP-3beta (Macrophage Inflammatory Protein-3beta) | 380 | 190 |
| MMP-9 (Matrix Metalloproteinase-9) | 750 | 890 |
| MPO (Myeloperoxidase) | 400 | 540 |

TABLE 2-continued

Rodent MAP results.

| | pg/ml | |
| --- | --- | --- |
| | Non-polarizing | IL-27 |
| Myoglobin | <LOW> | <LOW> |
| NGAL (Lipocalin-2) | 9900 | 6700 |
| OSM (Oncostatin M) | 82 | 98 |
| Osteopontin | 170 | 270 |
| RANTES | 46 | 22 |
| SAP (Serum Amyloid P) | <LOW> | <LOW> |
| SCF (Stem Cell Factor) | 17 | 14 |
| SGOT (Serum Glutamic-Oxaloacetic Transaminase) | <LOW> | <LOW> |
| TIMP-1 (Tissue Inhibitor of Metalloproteinase Type-1) | 120 | 160 |
| Tissue Factor | 1700 | 920 |
| TNF-alpha (Tumor Necrosis Factor-alpha) | 700 | 1000 |
| TPO (Thrombopoietin) | 1800 | 470 |
| VCAM-1 (Vascular Cell Adhesion Molecule-1) | 1400 | 1300 |
| VEGF (Vascular Endothelial Cell Growth Factor) | 2810 | 2460 |
| vWF (von Willebrand Factor) | 190 | 230 |

<LOW> values reflect samples not measurable on the standard curve
*uIU/ml

Further analysis using intracellular staining revealed that when stimulated under similar conditions followed by restimulation with phorbol 12-myristate 13-acetate (PMA) and ionomycin there was a small percentage of IL-10+ CD4+ and CD8+ T cells, but the addition of IL-27 led to a marked increase in this percentage (FIG. 14 Panels B and C). While these results indicated that a similar number of CD4+ and CD8+ T cells made IL-10 in response to IL-27, the amount of IL-10 in the supernatant from the cultures enriched for CD4+ T cells was higher than that observed for the cultures containing the CD8+ T cells, consistent with differences in the mean fluorescent intensity (MFI) (FIG. 14 Panels B and C). Consequently, the majority of the studies presented in this example focused on CD4+ T cells as a source of IL-10.

The IL-27R is Required for Optimal T Cell Production of IL-10 In Vitro and In Vivo The studies described above indicated that IL-27 could enhance T cell production of IL-10. To assess the role of the IL-27R in these events, splenocytes from WT or Il-27ra−/− mice were activated under non-polarizing conditions in the presence or absence of IL-27, and IL-10 was assayed. Whereas cells from WT mice secreted enhanced levels of IL-10 in response to IL-27, this was not observed in the cultures from the Il-27ra−/− mice (FIG. 15 Panel A). Indeed, even basal levels of IL-10 in these supernatants were reduced compared with WT controls. To assess whether IL-27/IL-27R was involved in the regulation of inflammatory responses in vivo, an experimental system in which WT and Il-27ra−/− mice were chronically infected with $T.$ $gondii^{38}$ was used. In these studies, restimulation of brain mononuclear cell (BMNC) preparations and splenocytes from chronically infected WT mice directly ex vivo revealed the presence of CD4+ T cells that produce IL-10. In contrast, when cells from the brains and spleens of chronically infected Il-27ra−/− mice were used there was a marked defect in IL-10 (FIG. 15 Panel B). Conversely, restimulation of wild-type BMNC with STAg in the presence of IL-27 resulted in a significant augmentation of IL-10 (FIG. 15 Panel C). These results collectively suggest a prominent role for IL-27 and the IL-27R in promoting T cell production of IL-10 in vitro and in the setting of chronic infection-induced inflammation associated with $T.$ $gondii$.

IL-27 Induces the Production of Il-10 Under $T_H1$ and $T_H2$ But not $T_H17$ Conditions While the studies described above were performed under neutral conditions, the data from mice infected with $T.$ $gondii$ implicate a role for IL-27 in the development of IL-10 producers during a $T_H1$ dominated response. Therefore, additional in vitro studies were performed to determine at what point after T cell activation IL-10 was produced and to assess the ability of IL-27 to promote IL-10 under conditions that favored the development of $T_H1$, $T_H2$ or $T_H17$ cells. Analysis of L-10 production by CD4+ T cells over a four day period in response to IL-27 revealed that the cells began making IL-10 48 hours after activation and that the numbers of IL-10+ cells peaked at 72 hours and were maintained over 96 hours (FIG. 16 Panel A). In addition, the cells were CFSE labeled to determine if the IL-10 producing T cells generated by IL-27 were actively proliferating or part of a non-replicating population of T cells. As shown by CFSE dilution only the CFSE dim cells made IL-10 in response to IL-27. This finding is consistent with models in which proliferation is required for T cells to acquire cytokine production[44]. Also, the pattern of IL-10 production in these experiments correlates with the expression profile of the IL-27R on recently activated T cells[45].

Consistent with previous reports[23], under $T_H1$ conditions (IL-12 plus (α-IL-4) there were low numbers of CD4+ T cells that made IL-10, but the addition of IL-27 resulted in an increase in the percentage of cells that stained positively for IL-10 (FIG. 16 Panel B). Under $T_H2$ conditions (IL-4 plus α-IFN-γ) there was a considerable number of IL-10+ CD4+ T cells, similar to previous reports, and the addition of IL-27 resulted in a marked increase in the percentage and MFI for IL-10 staining. Surprisingly, polarization of CD4+ T cells under $T_H17$ conditions (TGF-β plus IL-6) resulted in the presence of the largest population of T cells that produced IL-10 when compared to all other conditions. However, when IL-27 was added there was no further increase in IL-10 (FIG. 16 Panel B). Together, these data indicate that the ability of IL-27 to promote IL-10 production is most prominent under $T_H1$ and $T_H2$ but not $T_H17$ conditions.

Effects of IL-27 on Dual Cytokine Producers

Although IL-27 can promote IL-10 production under $T_H1$ and $T_H2$ conditions, and there was a significant proportion of IL-10+ CD4+ T cells following $T_H17$ polarization, it was unclear whether these IL-10+ cells also produce signature cytokines associated with these $T_H$ subsets. Therefore, CD4+ T cells were stimulated under $T_H1$, $T_H2$ and $T_H17$ conditions and intracellular staining for IL-10 was combined with IFN-γ, IL-13 or IL-17 respectively. When stimulated under $T_H1$ conditions, the majority of IL-10 producing T cells also stained positive for IFN-γ, but this population of double producers were still a minority compared to the cells producing just IFN-γ (FIG. 17 Panel A). Addition of IL-27 did not reduce the number of IFN-γ+ cells instead it resulted in an increase in the percentage of IFN-γ+IL-10+CD4+ T cells. Under $T_H2$ conditions approximately 50% of the IL-10+ cells were also making IL-13 (FIG. 17 Panel A). Addition of IL-27 increased the percentage of IL-10+ cells and caused a concurrent reduction in the number of IL-13+ IL-10+ cells and the IL-13 single producers.

Unexpectedly, analysis of T cells cultured with IL-6 plus TGF-β ($T_H17$) for the production of IL-17 and IL-10 revealed the presence of a three distinct populations of T cells: single producers of IL-17 or IL-10, and a population of IL-17+IL-10+ cells (FIG. 17 Panel A). Similar to previous reports[38] the addition of IL-27 inhibited expression of IL-17, but did not increase the percentage of cells expressing IL-10. Rather, there was an increase in the expansion of the IL-10+IL-17-T cells. Given the presence of accessory cells in these cultures it is was possible that the ability of IL-27 to inhibit the production of IL-17 is the result of its ability to induce IL-10 secretion. However, when CD4+ T cells from IL-10-/- mice were used, IL-27 was still able to inhibit IL-17 production (FIG. 17 Panel B).

TGF-β Enhances the Ability of IL-27 to Drive a Population of IL-10+CD4+ T Cells

The finding that $T_H17$ cells produced significant levels of IL-10 combined with the inability of IL-27 to enhance IL-10 under these conditions suggested that TGF-β or IL-6 may also be involved in the regulation of these events. Examination of the effects of TGF-β on CD4+ T cells revealed that unlike IL-27, TGF-β alone resulted in a modest increase in IL-10, but when combined with IL-27 it had an additive effect leading to an increase in the percentage of IL-10+ cells as well as an increase in the MFI (FIG. 18 Panels A and B). In addition, while exogenous TGF-β did increase IL-10 production, neutralization of endogenous TGF-β did not eliminate the ability of IL-27 to promote IL-10 production, but it did lead to a modest reduction in the percentage of IL-10+ cells (data not shown).

Since TGF-β can convert CD4+ CD25- T cells into CD4+ CD25+ induced Treg cells that express Foxp3[46, 47], it was possible that the inclusion of TGF-β would favor Treg expansion and that IL-27 promotes Treg secretion of IL-10. Therefore, CD4+ T cells from Foxp3GFP chimeric mice[48] were activated with α-CD3 and α-CD28 under non-polarizing conditions in the presence of TGF-β, IL-27 or the combination of both cytokines. After 72 hours of incubation under non-polarizing conditions few Foxp3GFP+ cells were present in the cultures without TGF-β; however, addition of TGF-β resulted in the generation of a large population of Foxp3GFP+ CD4+ T cells with fewer than 10% making IL-10 (FIG. 18 Panel C). When CD4+ T cells were cultured in the presence of IL-27 there was no expansion of Foxp3GFP+ cells, but 50% of the Foxp3GFP+ cells were making IL-10. However, the majority of the IL-10 producing T cells that were generated in response to IL-27 were Foxp3GFP—(20% versus 1.4%). Lastly, when TGF-β was combined with IL-27 there was an almost 70% decrease in the number of Foxp3GFP+ cells compared to the cultures containing TGF-β alone. As seen with IL-27 alone, close to 50% of the Foxp3GFP+ cells made IL-10, but the majority of the IL-10 producing CD4+ T cells remained Foxp3GFP—, indicating that the effects of IL-27 on IL-10 production are not specific to Foxp3+ T regs. Together, these data indicate that TGF-β has a synergistic effect on IL-10 production by CD4+ T cells when combined with IL-27, and this result is not due to increased numbers of Foxp3+ Treg cells in these cultures.

A Role for IL-6 in Promoting IL-10 Production

While TGF-β could enhance the ability of IL-27 to stimulate IL-10 production alone it could not account for the high percentage of IL-10+ T cells present under $T_H17$ conditions. Therefore, to determine if IL-6, a type I cytokine that shares structural homology and a receptor subunit with IL-27, can also promote IL-10 production, CD4+ T cells were incubated with IL-6 under non-polarizing conditions. In these experiments, as seen with TGF-β, the addition of IL-6 resulted in only a modest increase in IL-10 (FIG. 19 Panels A and B). Yet, when combined with TGF-β IL-6 synergized to promote the emergence of a large population of IL-10+ CD4+ T cells. Since the ability of IL-27 to positively regulate IL-10 was most apparent under $T_H1$ polarizing conditions, the effect of IL-6 on IL-10 production under $T_H1$ and $T_H2$ conditions was examined. Unlike IL-27, IL-6 was not able to enhance IL-10 under following $T_H1$ polarization (FIG. 21). In contrast, under $T_H2$ differentiation conditions the addition of IL-6 had an additive effect on the level of IL-10 that was made (FIG. 21).

A Role for Stat1 and Stat3 for the Generation of IL-10 Producing CD4+ T Cells

Activation of specific STAT proteins in CD4+ T cells is one of the contributing factors associated with the differentiation of T cells into distinct $T_H$ cell lineages, and IL-27 has been shown to activate a number of STAT proteins including STAT1 (and as a consequence T-bet), STAT3 and to a lesser extent STAT4[49, 50] while IL-6 primarily activates STAT3 and to a lesser extent STAT1[51, 52]. In order to determine the kinetics with which IL-27 and IL-6 activate STAT1 and STAT3, purified CD4+ T cells were stimulated with each cytokine over a period of three hours and phosphorylation of these transcription factors was monitored. These studies revealed that the CD4+ T cells were able to phosphorylate STAT1 and STAT3 in response to IL-6 and IL-27, however IL-6 was able to do this at a faster rate than IL-27 (FIG. 19 Panels C and D). Although the highest number of P-STAT1+ cells was not seen until 30 minutes after stimulation with IL-27, there was no difference in the percentage of P-STAT1+ cells between the peak of the IL-6 and IL-27 response. On the other hand, IL-6 was such a strong inducer of STAT3 phosphorylation that after 5 minutes of stimulation approximately 90% of the T cells were P-STAT3+, and a high level of P-STAT3 was maintained over a 3 hour time period. In contrast, a much smaller percentage of CD4+ T cells stained positive for P-STAT3 in response to IL-27 and this population of P-STAT3+ cells were not maintained at 3 hours post-stimulation.

To further investigate the role of the JAK-STAT signaling pathway in the induction of IL-10 by IL-27, mice deficient for individual STAT proteins were used. The ability of IL-27 to inhibit IL-17 has been previously attributed to its ability to activate STAT1[38], while a role for IL-27R signaling in the promotion of $T_H1$ differentiation has largely been attributed to activation of T-bet through STAT1 dependent as well as independent mechanisms[53]. Therefore, to determine if the ability of IL-27 to promote IL-10 involved these proteins CD4+ T cells obtained from Stat1-/- and Tbx21-/- (T-bet-deficient) mice were stimulated under non-polarizing conditions in the presence or absence of IL-27. CD4+ T cells from STAT1−/− mice were unable to produce IL-10 in response to IL-27 (FIG. 20 Panel A), while the absence of T-bet did not affect the ability of IL-27 to promote IL-10 (FIG. 20 Panel B).

To assess the role of STAT3, CD4+ T cells derived from mice with a floxed STAT3 allele that also express a CD4-Cre transgene (Stat3CD4−/−)[54] were stimulated as before in the presence or absence of IL-27. Removal of the STAT3 allele from the CD4+ T cells reduced their ability to make IL-10 in response to IL-27 compared to their Stat3fl/fl CD4-Cre-negative wild-type littermate controls (FIG. 20 Panel C). These data indicate that STAT1 and STAT3 are involved in the ability of IL-27 to promote IL-10 production.

In addition, while IL-27 has also been linked to STAT4, when CD4+ T cells derived from Stat-4−/− mice were cultured under non-polarizing conditions in the presence of IL-27 the absence of STAT4 did not hinder the ability of IL-27 to promote IL-10 (FIG. 20 Panel D), indicating that this is a STAT4 independent event. However, it is important to note that when STAT4−/− T cells were cultured under $T_H1$ conditions they produced less IL-10 compared to wild-type cells in response to IL-12 even when IL-27 was added (FIG. 22).

Lastly, CD4+ T cells from Stat1−/− and Stat3CD4−/− mice were assessed for their ability to produce IL-10 when stimulated with IL-6 alone or in combination with TGF-β. The CD4+ T cells from Stat1−/− and Stat3CD4−/− mice displayed a reduced capacity to make IL-10 in response to IL-6 (FIG. 20 Panels E and F). In contrast, CD4+ T cells from the Stat1−/− mice made equivalent amounts of IL-10 when incubated with IL-6 plus TGF-β compared to the wild-type controls while T cells from the Stat3CD4−/− mice were deficient in their ability to produce IL-10 under these same conditions. These findings indicate that STAT3, but not STAT1, signaling is required by IL-6 in order to initiate IL-10 production under $T_H17$ conditions.

Discussion

Since IL-10's original description as a cytokine associated with $T_H2$ cells, it is now recognized that there are multiple innate and adaptive sources of IL-10 that in turn acts as a global inhibitor of many classes ($T_H1$, $T_H2$, $T_H17$) of immune responses. Nevertheless, despite the early appreciation that T cells were major sources of IL-10, there remain many questions about the factors that govern its expression in these lymphocytes. Initial work by Trinchieri and colleagues implicated IL-12 in driving the development of IFN-γ/IL-10 double producers[23, 26], observations recapitulated here by data showing that under $T_H1$ conditions STAT4 is involved in these events. Moreover, chronic stimulation of human and mouse T cells in the presence of IL-10 led to the emergence of a population of T helper cells (Tr1) that secreted high levels of IL-10 and which could ameliorate colitis[17]. Similarly, repeated stimulation of naïve human and murine CD4+ T cells in vitro with dexamethasone plus vitamin D3 has been shown to promote IL-10 production by a population of Treg cells[55]. In contrast, the studies presented here reveal that, even after short-term stimulation, IL-27 and IL-6 were able to induce T cell production of IL-10 under a variety of polarizing conditions. This observation identifies a new pathway that promotes the production of IL-10 and reinforces the complex relationship between the pro- and anti-inflammatory properties of the IL-6/IL-12 family members.

Although IL-27 was first described based on its ability to promote $T_H1$ responses, it is now recognized that this type I cytokine has a role as a negative regulator of the intensity and duration of T cell responses[32-34]. The broad anti-inflammatory effects of IL-27 have been attributed to its ability to antagonize T helper cell functions through inhibition of the production of IFN-γ, IL-2, IL-4 and IL-17[50, 56]. However, in a number of experimental settings the phenotype of Il-27ra−/− mice has been remarkably similar to that of the IL-10−/− mice[33, 38, 39]. For instance, both L-10−/− and Il-27ra−/− mice infected with *T. gondii* develop a lethal CD4+ T cell mediated inflammation that is associated with dysregulated $T_H1$ responses acutely[14, 15, 33], but altered $T_H17$ responses in chronic disease[38, 42]. Related to these latter reports, Sher and colleagues established that CD4+ CD25-Foxp3-IL-10+ T cells are required to prevent *toxoplasma*-induced pathology[29]. The data presented here, together with these findings, suggest a model in which one of the functions of IL-27 is to promote T cell production of IL-10 that helps to limit T cell mediated pathology during infection. Presumably, this regulatory pathway would not be restricted to toxoplasmosis but the enhanced inflammation observed in Il-27ra−/− mice in a variety of infectious and inflammatory settings[50, 56] may, at least in part, be attributed to defective IL-10 responses.

While there are multiple cellular sources of IL-10, there are a limited number of studies that have defined the lineage specific requirements for IL-10 transcription. In macrophages, microbial products and immune complexes can induce IL-10 and MAPK, NF-KB and Sp1 are implicated in the transcriptional regulation of this gene[57-59]. In T cells, much less is known about the molecular events that control IL-10 synthesis although in $T_H2$ cells the JUN proteins have been implicated in these events and GATA3 is associated with remodeling and stability of the IL-10 locus required for transcription of this gene[60]. Since IL-27 antagonizes GATA3 expression[61], it seems unlikely that this particular transcription factor accounts for the ability of IL-27 and IL-6 to promote IL-10 transcription under $T_H1$ and $T_H17$ polarizing conditions. Rather, the data presented here link STAT3 predominantly, as well as STAT1 and STAT4, to the cytokine mediated induction of IL-10. This observation is consistent with the presence of STAT binding sites in the IL-10 promoter and a previous report that IFN-α can induce the recruitment of STAT1 and STAT3 to trans-activate an IL-10 reporter[62].

It is notable that while IL-6 and IL-27 both signal through gp130, activate STAT1 and STAT3 and can promote IL-10, only IL-27 can down regulate IL-2 and IL-17 whereas IL-6 promotes $T_H17$ activity. These observations are part of a literature which has highlighted some of the seemingly contradictory effects of STAT molecules in $T_H$ cell differentiation and function. Since the mid-1990s STAT4 and STAT6 were recognized as being key transcription factors that promoted $T_H1$ and $T_H2$ development[63, 64] while more recent studies have linked STAT3 to $T_H17$ cells[65-67]. It is now becoming apparent which STAT proteins mediate the effects of IL-27 in T cells. Thus, the ability of IL-27 to induce STAT1 can antagonize $T_H17$ development whereas STAT1 and STAT3 are required for IL-27 to induce IL-10. In contrast, the ability of IL-6 to promote $T_H17$ activity and IL-10 is STAT3 dependent. A likely explanation for these distinct effects is that although the receptors for IL-6 and IL-27 both contain gp130 there are unique IL-6Ra and IL-27Ra chains. Whether this indicates that a STAT1/STAT3 hetero-dimer mediates the IL-27 effects whereas IL-6 (when combined with TGF) only requires STAT3 homo-dimers remains to be formally tested. Alternatively, the difference in the magnitude of STAT3 phosphorylation between IL-6 and IL-27 suggest that the high levels of STAT3 actively induced by IL-6 may be sufficient to promote IL-10 whereas IL-27 requires the combination of STAT1 and STAT3.

While the focus of this work described in this example has been on the ability of IL-6 and IL-27 to promote IL-10, perhaps equally as important is the observation that TGF-β also influences this pathway. Based, in part, on the presence of T cell mediated inflammation in the TGF-β−/− mice[68], and the ability of TGF-β to directly inhibit innate and adaptive production of IFN-γ[1, 69, 70] it was assumed that TGF-β was an anti-inflammatory cytokine. With the realization that TGF-β has a prominent role in the development of Treg and $T_H17$ cells and now the production of IL-10 by non-Treg cells, it remains unclear whether it directs T cell differentiation or is a shared central regulator of T cell activity that is modulated by cytokines (IL-12, IL-6, IL-27) present in the environment that determine cell fate.

Although the studies presented here identify IL-27 and IL-6 as factors that promote T cell production of IL-10, one of the larger issues relates to whether this observation indicates the development of distinct T cell subsets. When Mossman and Coffman first described $T_H1$ and $T_H2$ cells they questioned the total diversity of T cell phenotypes and whether other T cell types exist in vivo[71]. Without limitation to any particular mechanism, one possible interpretation of the data presented here is that T helper subsets can be defined by their ability to produce IFN-γ, IL-4 and IL-17 alone or in combination with IL-10. To date, initial attempts using IL-27 to generate stable populations of IL-10 producing T cells in vitro have been unsuccessful. While there are several ways of interpreting these preliminary data, one possibility is that the ability to secrete IL-10 is not a hallmark of distinct T cell subsets but rather that cytokines like IL-27 and IL-6 represent modifiers for the main T cell subsets that allows them to make IL-10 in the context of chronic inflammation. Again, without limitation, this may be one mechanism that allows the establishment of an appropriate T helper subset required to deal with different classes of pathogens, but provides each of these distinct effector subsets with a mechanism to police their own inflammatory activities. Regardless, with the identification of IL-10 as a potent anti-inflammatory cytokine there were hopes that it could be used to treat a variety of autoimmune conditions. However, for reasons that are unclear, the clinical trials with IL-10 have been disappointing. Use of cytokines like IL-27 that can inhibit T cell effector functions combined with their ability to promote the production of IL-10 are expected to prove more useful for the management of inflammatory conditions.

In the context of the present invention, the experiments described in this example identify induction of IL-10 expression as another pathway (in addition to direct action on T cells) by which the complexes and fusion proteins described hereinabove can suppress the inflammatory response. In addition, the results described in this example indicate that coadministration of transforming growth factor beta can potentiate the effects of the complexes and fusion proteins.

Methods

Mice and Parasites

C57BL/6, Balb/c, Stat4−/− and Tbx21−/− mice were obtained from Jackson laboratories. WSX-1−/− (Il27ra−/−) mice were provided by Dr. Christiaan Saris (Amgen Inc.). Stat1−/− mice were provided by Dr Phillip Scott (University of Pennsylvania, Philadelphia, Pa.). Mice with a GFP reporter knocked in at the site of translation for Foxp3 have been described before[72], and were provided by Dr. Laurence Turka (University of Pennsylvania). Mice were housed and bred in specific pathogen-free facilities in the Department of Pathobiology at the University of Pennsylvania in accordance to institutional guidelines.

The ME49 strain of *T. gondii* was prepared from chronically infected CBA/ca mice and experimental animals were infected intraperitoneally with 20 cysts. Il27ra−/− and wild-type C57BL/6 control mice were treated on day 5 post-infection with 200 mg/L of sulfadiazine (Sigma) in their drinking water for two weeks in order to allow the Il-27ra−/− to progress to a chronic stage of infection. Soluble toxoplasma antigen (STAg) was prepared from tachyzoites of the RH strain as described previously[73]. BMNCs from chronically infected mice were isolated in accordance with a published protocol[42, 74].

Generation of IL-10 Producing T cells

CD4+ and CD8+ T cells were isolated from splenocytes and lymph nodes that were depleted of CD8+ and NK1.1+ cells to enrich for CD4+ T cells or were depleted of CD4+ and NK1.1+ cells to enrich for CD8+ T cells by magnetic bead separation (Polysciences). Cells were plated in 96 well round-bottom plates (Costar) at a density of 5×106 cells/ml. The cells were stimulated with anti-TCR antibody (α-CD3; 1 µg/ml; eBioscience) and anti-CD28 antibody (1 µg/ml; eBioscience). For production of IL-10 T cell cultures were supplemented with either recombinant mouse IL-27 (100 ng/ml; Amgen) or human TGF-β (1 ng/ml; R & D) alone or in combination with IL-27. Additionally IFN-γ and IL-4 were neutralized in the non-polarized cultures using anti-IFN-γ (10 µg/ml; clone XMG1.2) and anti-IL-4 (10 µg/ml; clone 11B11). In some cases the T cells were cultured under $T_H1$ (10 ng/ml recombinant IL-12; eBioscience plus 10 µg/ml α-IL-4), $T_H2$ (8 ng/ml recombinant IL-4; eBioscience plus 10 µg/ml α-IFN-γ) or $T_H17$ (1 ng/ml TGF-β; R & D, 10 ng/ml IL-6; eBioscience, plus 10 µg/ml α-IFN-γ and α-IL-4) conditions. The CD8+ T cells were harvested on day 3, while the CD4+ T cells were supplemented with fresh medium and reagents on day 3 and harvested on day 4. T cells were then restimulated with PMA and ionomycin plus brefeldin A (Sigma). Flow cytometric analysis was performed on a FACSCaliber (BD Biosciences) or BDFACS CantoII (BD Biosciences) instrument and analyzed using FlowJo software (Tree Star Inc.). All antibodies were purchased from BD Pharmingen or eBioscience. For intracellular staining of GFP cells were first stained with a mouse anti-GFP antibody (eBioscience) followed by a second stain with a rabbit anti-mouse-FITC antibody (Jackson Immunoresearch).

Intracellular Staining for P-STAT1 and P-STAT3

CD4+ T cells were purified from C57BL/6 mice using a CD4+ isolation kit (Milltenyi). 1×106 purified CD4+ T cells were incubated with IL-6 or IL-27 for 5, 30, 60 or 180 minutes. The cells were then fixed for 10 minutes with 2% paraformaldehyde at 37° C. After fixation the cells were then permeabilized with 90% methanol for 30 minutes on ice followed by staining for CD4, P-STAT1 and P-STAT3. Antibodies against phosphorylated tyrosine residues of STAT1 and STAT3 were purchased from BD Pharmingen.

Statistics

Paired Student t test were used to determine significant differences were stated and a P value <0.05 was considered significant.

REFERENCES FOR EXAMPLE 3

1. Fiorentino, D. F., Bond, M. W. & Mosmann, T. R. Two types of mouse T helper cell. IV. Th2 clones secrete a factor that inhibits cytokine production by Th1 clones. J Exp Med 170, 2081-95 (1989).

2. Moore, K. W. et al. Homology of Cytokine synthesis inhibitory factor (IL-10) to the Epstein-Barr virus gene BCRFI. Science 248, 1230-4 (1990).
3. de Waal Malefyt, R. et al. Interleukin 10 (IL-10) and viral IL-10 strongly reduce antigen-specific human T cell proliferation by diminishing the antigen-presenting capacity of monocytes via downregulation of class II major histocompatibility complex expression. J Exp Med 174, 915-24 (1991).
4. Ding, L. & Shevach, E. M. IL-10 inhibits mitogen-induced T cell proliferation by selectively inhibiting macrophage costimulatory function. J Immunol 148, 3133-9 (1992).
5. Hsu, D. H., Moore, K. W. & Spits, H. Differential effects of IL-4 and IL-10 on IL-2-induced IFN-gamma synthesis and lymphokine-activated killer activity. Int Immunol 4, 563-9 (1992).
6. Bogdan, C., Vodovotz, Y. & Nathan, C. Macrophage deactivation by interleukin 10. J Exp Med 174, 1549-55 (1991).
7. de Waal Malefyt, R., Abrams, J., Bennett, B., Figdor, C. G. & de Vries, J. E. Interleukin 10(IL-10) inhibits cytokine synthesis by human monocytes: an autoregulatory role of IL-10 produced by monocytes. J Exp Med 174, 1209-20 (1991).
8. Ding, L., Linsley, P. S., Huang, L. Y., Germain, R. N. & Shevach, E. M. IL-10 inhibits macrophage costimulatory activity by selectively inhibiting the up-regulation of B7 expression. J Immunol 151, 1224-34 (1993).
9. Murphy, E. E. et al. B7 and interleukin 12 cooperate for proliferation and interferon gamma production by mouse T helper clones that are unresponsive to B7 costimulation. J Exp Med 180, 223-31 (1994).
10. Kuhn, R., Lohler, J., Rennick, D., Rajewsky, K. & Muller, W. Interleukin-10-deficient mice develop chronic enterocolitis. Cell 75, 263-74 (1993).
11. Yen, D. et al. IL-23 is essential for T cell-mediated colitis and promotes inflammation via IL-17 and IL-6. J Clin Invest 116, 1310-6 (2006).
12. Moore, K. W., de Waal Malefyt, R., Coffman, R. L. & O'Garra, A. Interleukin-10 and the interleukin-10 receptor. Annu Rev Immunol 19, 683-765 (2001).
13. Grunig, G. et al. Interleukin-10 is a natural suppressor of cytokine production and inflammation in a murine model of allergic bronchopulmonary aspergillosis. J Exp Med 185, 1089-99 (1997).
14. Gazzinelli, R. T. et al. In the absence of endogenous IL-10, mice acutely infected with *Toxoplasma gondii* succumb to a lethal immune response dependent on CD4+ T cells and accompanied by overproduction of IL-12, IFN-gamma and TNF-alpha. J Immunol 157, 798-805 (1996).
15. Neyer, L. E. et al. Role of interleukin-10 in regulation of T-cell-dependent and T-cell-independent mechanisms of resistance to *Toxoplasma gondii*. Infect Immun 65, 1675-82 (1997).
16. Hunter, C. A. et al. IL-10 is required to prevent immune hyperactivity during infection with *Trypanosoma cruzi*. J Immunol 158, 3311-6 (1997).
17. Groux, H. et al. A CD4+ T-cell subset inhibits antigen-specific T-cell responses and prevents colitis. Nature 389, 737-42 (1997).
18. Suffia, I. J., Reckling, S. K., Piccirillo, C. A., Goldszmid, R. S. & Belkaid, Y. Infected site-restricted Foxp3+ natural regulatory T cells are specific for microbial antigens. J Exp Med 203, 777-88 (2006).
19. Zhang, X. et al. IL-10 is involved in the suppression of experimental autoimmune encephalomyelitis by CD25+ CD4+ regulatory T cells. Int Immunol 16, 249-56 (2004).
20. Jonuleit, H., Schmitt, E., Schuler, G., Knop, J. & Enk, A. H. Induction of interleukin 10-producing, nonproliferating CD4(+) T cells with regulatory properties by repetitive stimulation with allogeneic immature human dendritic cells. J Exp Med 192, 1213-22 (2000).
21. Vieira, P. L. et al. IL-10-secreting regulatory T cells do not express Foxp3 but have comparable regulatory function to naturally occurring CD4+ CD25+ regulatory T cells. J Immunol 172, 5986-93 (2004).
22. Del Prete, G. et al. Human IL-10 is produced by both type 1 helper (Th1) and type 2 helper (Th2) T cell clones and inhibits their antigen-specific proliferation and cytokine production. J Immunol 150, 353-60 (1993).
23. Gerosa, F. et al. Interleukin-12 primes human CD4 and CD8 T cell clones for high production of both interferon-gamma and interleukin-10. J Exp Med 183, 2559-69 (1996).
24. O'Garra, A. & Vieira, P. T(H)1 cells control themselves by producing interleukin-10. Nat Rev Immunol 7, 425-8 (2007).
25. Trinchieri, G. Interleukin-10 production by effector T cells: Th1 cells show self control. J Exp Med 204, 239-43 (2007).
26. Gerosa, F. et al. CD4(+) T cell clones producing both interferon-gamma and interleukin-10 predominate in bronchoalveolar lavages of active pulmonary tuberculosis patients. Clin Immunol 92, 224-34 (1999).
27. Pohl-Koppe, A., Balashov, K. E., Steere, A. C., Logigian, E. L. & Hafler, D. A. Identification of a T cell subset capable of both IFN-gamma and IL-10 secretion in patients with chronic *Borrelia burgdorferi* infection. J Immunol 160, 1804-10 (1998).
28. Anderson, C. F., Oukka, M., Kuchroo, V. J. & Sacks, D. CD4+ CD25-Foxp3- Th1 cells are the source of IL-10-mediated immune suppression in chronic cutaneous leishmaniasis. J Exp Med 204, 285-97 (2007).
29. Jankovic, D. et al. Conventional T-bet+Foxp3- Th1 cells are the major source of host-protective regulatory IL-10 during intracellular protozoan infection. J Exp Med 204, 273-83 (2007).
30. Pflanz, S. et al. IL-27, a heterodimeric cytokine composed of EBI3 and p28 protein, induces proliferation of naive CD4(+) T cells. Immunity 16, 779-90 (2002).
31. Chen, Q. et al. Development of Th1-type immune responses requires the type I cytokine receptor TCCR. Nature 407, 916-920 (2000).
32. Yoshida, H. et al. WSX-1 is required for the initiation of Th1 responses and resistance to *L. major* infection. Immunity 15, 569-78 (2001).
33. Villarino, A. et al. The IL-27R (WSX-1) is required to suppress T cell hyperactivity during infection. Immunity 19, 645-55 (2003).
34. Hamano, S. et al. WSX-1 is required for resistance to *Trypanosoma cruzi* infection by regulation of proinflammatory cytokine production. Immunity 19, 657-67 (2003).
35. Artis, D. et al. Cutting edge: early IL-4 production governs the requirement for IL-27-WSX-1 signaling in the development of protective Th1 cytokine responses following *Leishmania major* infection. J Immunol 172, 4672-5 (2004).
36. Yamanaka, A. et al. Hyperproduction of proinflammatory cytokines by WSX-1-deficient NKT cells in concanavalin A-induced hepatitis. J Immunol 172, 3590-6 (2004).

37. Holscher, C. et al. The IL-27 receptor chain WSX-1 differentially regulates antibacterial immunity and survival during experimental tuberculosis. J Immunol 174, 3534-44 (2005).
38. Stumhofer, J. S. et al. Interleukin 27 negatively regulates the development of interleukin 17-producing T helper cells during chronic inflammation of the central nervous system. Nat Immunol 7, 937-45 (2006).
39. Batten, M. et al. Interleukin 27 limits autoimmune encephalomyelitis by suppressing the development of interleukin 17-producing T cells. Nat Immunol 7, 929-36 (2006).
40. Amadi-Obi, A. et al. T(H)$_{1-7}$ cells contribute to uveitis and scleritis and are expanded by IL-2 and inhibited by IL-27/STAT1. Nat Med (2007).
41. Wille, U., Villegas, E. N., Striepen, B., Roos, D. S. & Hunter, C. A. Interleukin-10 does not contribute to the pathogenesis of a virulent strain of *Toxoplasma gondii*. Parasite Immunol 23, 291-6 (2001).
42. Wilson, E. H., Wille-Reece, U., Dzierszinski, F. & Hunter, C. A. A critical role for IL-10 in limiting inflammation during toxoplasmic encephalitis. J Neuroimmunol 165, 63-74 (2005).
43. Villarino, A. V. et al. IL-27 limits IL-2 production during Th1 differentiation. J Immunol 176, 237-47 (2006).
44. Bird, J. J. et al. Helper T cell differentiation is controlled by the cell cycle. Immunity 9, 229-37 (1998).
45. Villarino, A. V. et al. Positive and negative regulation of the IL-27 receptor during lymphoid cell activation. J Immunol 174, 7684-91 (2005).
46. Chen, W. et al. Conversion of peripheral CD4+ CD25- naive T cells to CD4+ CD25+ regulatory T cells by TGF-beta induction of transcription factor Foxp3. J Exp Med 198, 1875-86 (2003).
47. Rich, S., Seelig, M., Lee, H. M. & Lin, J. Transforming growth factor beta 1 costimulated growth and regulatory function of staphylococcal enterotoxin B-responsive CD8+ T cells. J Immunol 155, 609-18 (1995).
48. Fontenot, J. D. et al. Regulatory T cell lineage specification by the forkhead transcription factor foxp3. Immunity 22, 329-41 (2005).
49. Villarino, A. V. & Hunter, C. A. Biology of recently discovered cytokines: discerning the pro- and anti-inflammatory properties of interleukin-27. Arthritis Res Ther 6, 225-33 (2004).
50. Hunter, C. A. New IL-12-family members: IL-23 and IL-27, cytokines with divergent functions. Nat Rev Immunol 5, 521-31 (2005).
51. Lutticken, C. et al. Association of transcription factor APRF and protein kinase Jak1 with the interleukin-6 signal transducer gp130, Science 263, 89-92 (1994).
52. Zhong, Z., Wen, Z. & Darnell, J. E., Jr. Stat3: a STAT family member activated by tyrosine phosphorylation in response to epidermal growth factor and interleukin-6. Science 264, 95-8 (1994).
53. Villarino, A. V., Huang, E. & Hunter, C. A. Understanding the pro- and anti-inflammatory properties of IL-27. J Immunol 173, 715-20 (2004).
54. Chiarle, R. et al. Stat3 is required for ALK-mediated lymphomagenesis and provides a possible therapeutic target. Nat Med 11, 623-9 (2005).
55. Barrat, F. J. et al. In vitro generation of interleukin 10-producing regulatory CD4(+) T cells is induced by immunosuppressive drugs and inhibited by T helper type 1 (Th1)- and Th2-inducing cytokines. J Exp Med 195, 603-16 (2002).
56. Kastelein, R. A., Hunter, C. A. & Cua, D. J. Discovery and biology of IL-23 and IL-27: related but functionally distinct regulators of inflammation. Annu Rev Immunol 25, 221-42 (2007).
57. Brightbill, H. D., Plevy, S. E., Modlin, R. L. & Smale, S. T. A prominent role for Sp1 during lipopolysaccharide-mediated induction of the IL-10 promoter in macrophages. J Immunol 164, 1940-51 (2000).
58. Liu, Y. W., Chen, C. C., Tseng, H. P. & Chang, W. C. Lipopolysaccharide-induced transcriptional activation of interleukin-10 is mediated by MAPK- and NF-kappaB-induced CCAAT/enhancer-binding protein delta in mouse macrophages. Cell Signal 18, 1492-500 (2006).
59. Lucas, M., Zhang, X., Prasanna, V. & Mosser, D. M. ERK activation following macrophage FcgammaR ligation leads to chromatin modifications at the IL-10 locus. J Immunol 175, 469-77 (2005).
60. Shoemaker, J., Saraiva, M. & O'Garra, A. GATA-3 directly remodels the IL-10 locus independently of IL-4 in CD4+ T cells. J Immunol 176, 3470-9 (2006).
61. Lucas, S., Ghilardi, N., Li, J. & de Sauvage, F. J. IL-27 regulates IL-12 responsiveness of naive CD4+ T cells through Stat1-dependent and -independent mechanisms. Proc Natl Acad Sci USA 100, 15047-52 (2003).
62. Ziegler-Heitbrock, L. et al. IFN-alpha induces the human IL-10 gene by recruiting both IFN regulatory factor 1 and Stat3. J Immunol 171, 285-90 (2003).
63. Hou, J. et al. An interleukin-4-induced transcription factor: IL-4 Stat. Science 265, 1701-6 (1994).
64. Jacobson, N. G. et al. Interleukin 12 signaling in T helper type 1 (Th1) cells involves tyrosine phosphorylation of signal transducer and activator of transcription (Stat)3 and Stat4. J Exp Med 181, 1755-62 (1995).
65. Chen, Z. et al. Selective regulatory function of Socs3 in the formation of IL-17-secreting T cells. Proc Natl Acad Sci USA 103, 8137-42 (2006).
66. Cho, M. L. et al. STAT3 and NF-kappaB signal pathway is required for IL-23-mediated IL-17 production in spontaneous arthritis animal model IL-1 receptor antagonist-deficient mice. J Immunol 176, 5652-61 (2006).
67. Mathur, A. N. et al. Stat3 and Stat4 direct development of IL-17-secreting Th cells. J Immunol 178, 4901-7 (2007).
68. Shull, M. M. et al. Targeted disruption of the mouse transforming growth factor-beta 1 gene results in multifocal inflammatory disease. Nature 359, 693-9 (1992).
69. Espevik, T. et al. Inhibition of cytokine production by cyclosporin A and transforming growth factor beta. J Exp Med 166, 571-6 (1987).
70. Silva, J. S., Twardzik, D. R. & Reed, S. G. Regulation of *Trypanosoma cruzi* infections in vitro and in vivo by transforming growth factor beta (TGF-beta). J Exp Med 174, 539-45 (1991).
71. Mosmann, T. R. & Coffman, R. L. TH1 and T$_H$2 cells: different patterns of lymphokine secretion lead to different functional properties. Annu Rev Immunol 7, 145-73 (1989).
72. Bettelli, E. et al. Reciprocal developmental pathways for the generation of pathogenic effector TH17 and regulatory T cells. Nature 441, 235-8 (2006).
73. Sharma, S. D., Mullenax, J., Araujo, F. G., Erlich, H. A. & Remington, J. S. Western blot analysis of the antigens of *Toxoplasma gondii* recognized by human IgM and IgG antibodies. J. Immunol. 131, 977-983 (1983).
74. Villegas, E. N. et al. Blockade of costimulation prevents infection-induced immunopathology in interleukin-10-deficient mice. Infect. Immun. 68, 2837-2844 (2000).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of increasing the production of IL10 in a mammalian subject with an inflammatory condition, the method comprising administering to the mammal at least one soluble recombinant complex selected from the group consisting of WSX-1 extracellular domain/IL-27 polypeptide and WSX-1 extracellular domain/p28 subunit, wherein the recombinant soluble complex signals through a gp130 receptor and wherein the production of IL10 is increased in the mammal by a fold selected from the group consisting of at least 10, at least 100, and at least 1000 fold.

2. The method of claim 1, wherein the at least one soluble recombinant complex is combined with a transforming growth factor beta (TGF-beta) and wherein this combination has an additive effect and increases further the production of IL10 in the mammal.

3. The method of claim 1, wherein the inflammatory condition in the mammal is ameliorated or suppressed.

4. The method of claim 1, wherein the subject is a human.

5. The method of claim 1, wherein the inflammatory condition is an immune disorder.

6. The method of claim 1, wherein the method comprises diagnosing the subject with the inflammatory condition prior to said administering.

* * * * *

UNITED STATES PATENT AND TRADEMARK OFFICE
CERTIFICATE OF CORRECTION

| | | |
|---|---|---|
| PATENT NO. | : 9,683,026 B2 | Page 1 of 1 |
| APPLICATION NO. | : 11/880121 | |
| DATED | : June 20, 2017 | |
| INVENTOR(S) | : Christopher A. Hunter and Jason Scott Stumhofer | |

It is certified that error appears in the above-identified patent and that said Letters Patent is hereby corrected as shown below:

In the Specification

In Column 1, after the title STATEMENT AS TO RIGHTS TO INVENTIONS MADE UNDER FEDERALLY SPONSORED RESEARCH AND DEVELOPMENT, please replace the paragraph at Lines 23-26 with the following paragraph:

--This invention was made with government support under grant number AI041158, AI042334 and AI055428 awarded by the National Institutes of Health. The government has certain rights in the invention.--

Signed and Sealed this
Second Day of January, 2018

Joseph Matal
*Performing the Functions and Duties of the
Under Secretary of Commerce for Intellectual Property and
Director of the United States Patent and Trademark Office*